(12) United States Patent
Wang et al.

(10) Patent No.: US 11,530,270 B2
(45) Date of Patent: Dec. 20, 2022

(54) ANTIBODY TARGETING IL-13RA2 AND USE THEREOF

(71) Applicant: CRAGE medical Co., Limited, Mongkok Kowloon (HK)

(72) Inventors: Peng Wang, Shanghai (CN); Huamao Wang, Shanghai (CN)

(73) Assignee: CRAGE medical Co., Limited, Mongkok Kowloon (HK)

(*) Notice: Subject to any disclaimer, the term of this patent is extended or adjusted under 35 U.S.C. 154(b) by 503 days.

(21) Appl. No.: 16/486,481

(22) PCT Filed: Feb. 8, 2018

(86) PCT No.: PCT/CN2018/075859
§ 371 (c)(1),
(2) Date: Oct. 22, 2019

(87) PCT Pub. No.: WO2018/149358
PCT Pub. Date: Aug. 23, 2018

(65) Prior Publication Data
US 2019/0359723 A1 Nov. 28, 2019

(30) Foreign Application Priority Data

Feb. 17, 2017 (CN) .......................... 201710087299.2
Jan. 26, 2018 (CN) .......................... 201810079015.X

(51) Int. Cl.
| | |
|---|---|
| *C07K 16/28* | (2006.01) |
| *C07K 16/46* | (2006.01) |
| *A61P 35/00* | (2006.01) |
| *A61K 35/17* | (2015.01) |
| *C07K 14/725* | (2006.01) |
| *C07K 14/705* | (2006.01) |
| *C07K 14/715* | (2006.01) |
| *C12N 5/0783* | (2010.01) |
| *C12N 15/113* | (2010.01) |
| *A61K 38/00* | (2006.01) |

(52) U.S. Cl.
CPC .......... *C07K 16/2866* (2013.01); *A61K 35/17* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 14/7158* (2013.01); *C07K 16/2809* (2013.01); *C07K 16/468* (2013.01); *C12N 5/0646* (2013.01); *C12N 15/1138* (2013.01); *A61K 38/00* (2013.01); *C07K 2317/565* (2013.01); *C07K 2317/622* (2013.01); *C07K 2317/73* (2013.01); *C07K 2317/76* (2013.01); *C07K 2317/92* (2013.01); *C07K 2319/02* (2013.01); *C07K 2319/03* (2013.01); *C07K 2319/30* (2013.01); *C07K 2319/33* (2013.01); *C12N 2310/14* (2013.01); *C12N 2320/31* (2013.01); *C12N 2510/00* (2013.01)

(58) Field of Classification Search
None
See application file for complete search history.

(56) References Cited

U.S. PATENT DOCUMENTS

| | | |
|---|---|---|
| 2013/0129753 A1 | 5/2013 | Doroski et al. |
| 2016/0039938 A1 | 2/2016 | Debinski |

FOREIGN PATENT DOCUMENTS

| | | |
|---|---|---|
| CN | 101440130 A | 5/2009 |
| JP | 2010190572 A | 9/2010 |
| WO | 2014072888 A1 | 5/2014 |
| WO | WO2014152361 A1 | 9/2014 |
| WO | 2016123143 A1 | 8/2016 |

OTHER PUBLICATIONS

Casset et al; Biochemical and Biophysical Research Communications, 2003; 307:198-205.*
Paul, Fundamental Immunology, 3rd Edition, 1993, pp. 292-295.*
Kobayashi et al. Protein Engineering; 1999; vol. 12, pp. 879-844.*
Brummell et al, Biochemistry; 1993; vol. 32, pp. 1180-1187.*
Coleman Research in Immunol; 1994; vol. 145; pp. 33-36.*
Rudikoff, et al. (Proc. Natl. Acad. Sci. USA, 79(6):1979-1983, 1982).*
Brorson et al. J. Immunol; 1999; vol. 163, pp. 6694-6701.*
Balyasnikova I. V., et. al. "Characterization and Immunotherapeutic Implications for a Novel Antibody Targeting Interleukin (IL)-13 Receptor 2," The Journal of Biological Chemistry, vol. 287(36): 30215-30227 (2012).
Kim JW et. al., "A novel single-chain antibody redirects adenovirus to IL13Ralpha2-expressing brain tumors," Scientific Reports, vol. 5 (18133): 1-12 (2015).
Krenciute G et. al., "Characterization and Functional Analysis of scFv-based Chimeric Antigen Receptors to Redirect T Cells to IL13Ralpha2-positive Glioma," Molecular Therapy, vol. 24(2): 354-363 (2016).
Dongelinger M. et al ., "Understanding the Significance and Implications of Antibody Numbering and Antigen-Binding Surface/Residue Definition," Frontiers in Immunology, vol. 9 (Article 2278): 15 pages (2018).
Jespers, L.S. et al., "Guiding the Selection of Human Antibodies from Phage Display Repertoires to a Single Epitope of an Antigen," Nature Biotechnology, vol. 12: 899-903 (1994).

(Continued)

*Primary Examiner* — Bridget E Bunner
*Assistant Examiner* — Fozia M Hamud
(74) *Attorney, Agent, or Firm* — Nelson Mullins Riley & Scarborough LLP; Jill Gorny Sloper, Esq.

(57) ABSTRACT

Provided is an antibody that specifically recognizes IL-13RA2, which can be used in the manufacture of a targeting anti-tumor medicament as well as a medicament for diagnosing a tumor.

13 Claims, 10 Drawing Sheets
Specification includes a Sequence Listing.

(56) References Cited

OTHER PUBLICATIONS

Debinski, W. (Oct. 16, 2013). "New Agents for Targeting of IL-13RA2 Expressed in Primary Human and Canine Brain Tumors," PLoSone 8(10):e77719, 15 pages.

International Search Report, dated Mar. 27, 2018, for PCT Application No. PCT/CN2018/075859, 6 pages.

Krenciute, G. et al. (Nov. 4, 2015). "Charachterization and Functional Analysis of scFv-Based CARs to Redirect T Ceils to IL13Rα2-Positive Glioma," Journal for Immunotherapy of Cancer 3(Supp. 2):p. 116, 2 pages.

Taiwanese Search Report, dated Jan. 5, 2019 for Taiwanese PCT Application No. TW107105721, filed Feb. 17, 2017, 1 page.

Del Bang, J. et al., "Taking up Cancer Immunotherapy Challenges: Bispecific Antibodies, the Path Forward?", Antibodies, vol. 5(1): 24 pages (2015).

Extended European Search Report, European Patent Application No. 18753921, dated Nov. 30, 2020, 14 pages.

Mitomu, K. et al., "Targeting IL-13Ralpha2-positive cancer with a novel recombinant immunotoxin composed of a single-chain antibody and mutated Pseudomonas exotoxin," Molecular Cancer Therapeutics, American Association for Cancer Research, vol. 7(6):1579-1587 (2008).

* cited by examiner

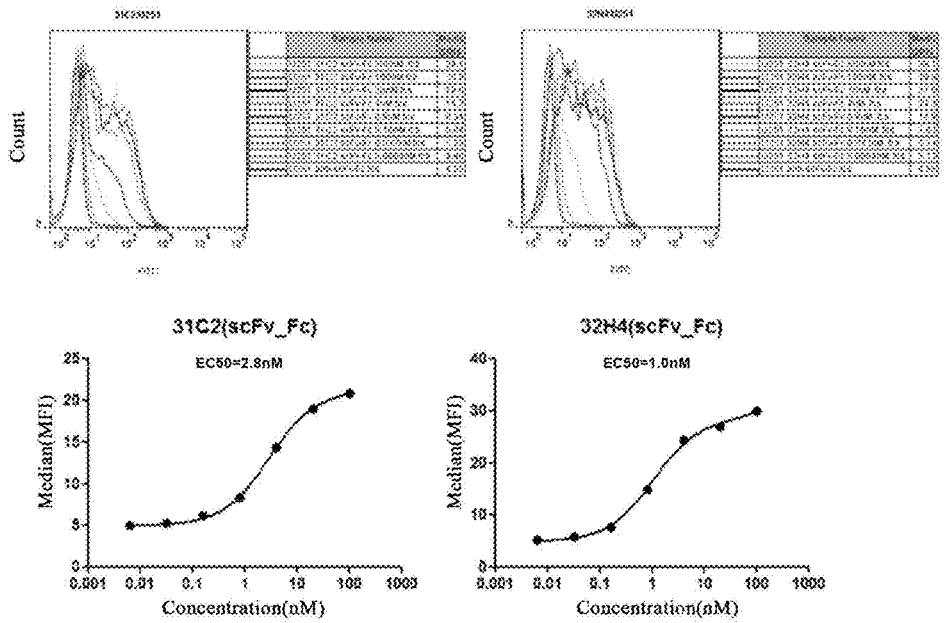

Figure 6

| Number | Name | Sequence | |
|---|---|---|---|
| 1 | LMF | CAGGAAACAGCTATGACCATGATTAC | SEQ ID NO:77 |
| 2 | BH1R | TGAGACCCACTCCAGCCCCTTCCCTGGAGCCTGGCGGACCCAMNNMNNMNNMNNMNNMNNA | SEQ ID NO:78 |
| 3 | BH2F | GGCTGGAGTGGGTCTCANNKATTNNKNNKNNKGGTNNKACANNKTACGCAGACTCCGTGAA | SEQ ID NO:79 |
| 4 | FdR | GACGTTAGTAAATGAATTTTCTGTATGAGG | SEQ ID NO:80 |
| 5 | IL1R | CCCTGGTTTCTGCTGATACCAMNNCAAMNNMNNMNNMNNMNNCTGACTGGCACGGCAAGTGA | SEQ ID NO:81 |
| 6 | IL2F | GGTATCAGCAGAAACCAGGGAAAGCCCCTAAGCTCCTGATCNNKNNKNNKNNKNNKTTGGAAA | SEQ ID NO:82 |

Figure 7

| Name | Dissociation constant Kd(S⁻¹) |
|---|---|
| 2C7 | 5.01E-04 |
| 2D3 | 5.43E-04 |
| 1D11 | 6.77E-04 |
| 1B11 | 7.36E-04 |
| 2A5 | 7.88E-04 |
| 2D4 | 8.37E-04 |
| 1H7 | 8.88E-04 |
| 1D8 | 9.40E-04 |
| 31C2 (Parent clone) | 1.23E-02 |

| Name | Dissociation constant Kd(S⁻¹) |
|---|---|
| 5G3 | 9.41E-04 |
| 5D7 | 1.54E-03 |
| 32H4 (Parent clone) | 8.97E-02 |

Figure 8

```
31C2 H  EVQLLESGGGLVQPGGSLRLSCAASGFTF SSYAMS WVRQAPGKGLEWVS AISGSGGSTYYADSVKG RFTI
2C7     EVQLLESGGGLVQPGGSLRLSCAASGFTF KLPAMS WVRQAPGKGLEWVS AITGSGGSTYYADSVKG RFTI
2D3     EVQLLESGGGLVQPGGSLRLSCAASGFTF RRPAMT WVRQAPGKGLEWVS AITGSGGSTYYADSVKG RFTI
1D11    EVQLLESGGGLVQPGGSLRLSCAASGFTF GTIPMS WVRQAPGKGLEWVS SISGSAGSTYYADSVKG RFTI
1B11    EVQLLESGGGLVQPGGSLRLSCAASGFTF SRDALN WVRQAPGKGLEWVS AISGSGGSTFYADSVKG RFTI
2A5     EVQLLESGGGLVQPGGSLRLSCAASGFTF SRYAMN WVRQAPGKGLEWVS AISASGGGTYYADSVKG RFTI
2D4     EVQLLESGGGLVQPGGSLRLSCAASGFTF RKYAMG WVRQAPGKGLEWVS GISGSVGSTYYADSVKG RFTI
1H7     EVQLLESGGGLVQPGGSLRLSCAASGFTF RRYAMS WVRQAPGKGLEWVS GISGSGGGTYYADSVKG RFTI
1D8     EVQLLESGGGLVQPGGSLRLSCAASGFTF SRYAMN WVRQAPGKGLEWVS AINASGGSTYYADSVKG RFTI

31C2 H  SRDNSKNTLYLQMNSLRAEDTAVYYCAK VRYGWGAGAFDY WGQGTLVTVSS SEQ ID NO:2
2C7     SRDNSKNTLYLQMNSLRAEDTAVYYCAK VRYGWGAGAFDY WGQGTLVTVSS SEQ ID NO:29
2D3     SRDNSKNTLYLQMNSLRAEDTAVYYCAK VRYGWGAGAFDY WGQGTLVTVSS SEQ ID NO:31
1D11    SRDNSKNTLYLQMNSLRAEDTAVYYCAK VRYGWGAGAFDY WGQGTLVTVSS SEQ ID NO:33
1B11    SRDNSKNTLYLQMNSLRAEDTAVYYCAK VRYGWGAGAFDY WGQGTLVTVSS SEQ ID NO:35
2A5     SRDNSKNTLYLQMNSLRAEDTAVYYCAK VRYGWGAGAFDY WGQGTLVTVSS SEQ ID NO:37
2D4     SRDNSKNTLYLQMNSLRAEDTAVYYCAK VRYGWGAGAFDY WGQGTLVTVSS SEQ ID NO:39
1H7     SRDNSKNTLYLQMNSLRAEDTAVYYCAK VRYGWGAGAFDY WGQGTLVTVSS SEQ ID NO:41
1D8     SRDNSKNTLYLQMNSLRAEDTAVYYCAK VRYGWGAGAFDY WGQGTLVTVSS SEQ ID NO:43
```

Figure 9A

| Clone | HCDR1 | Sequence | HCDR2 | Sequence |
|---|---|---|---|---|
| 31C2 | SSYAMS | SEQ ID NO:9 | AISGSGGSTYYADSVKG | SEQ ID NO:10 |
| 2C7 | KLPAMS | SEQ ID NO:45 | AITGSGGSTYYADSVKG | SEQ ID NO:52 |
| 2D3 | RRPAMT | SEQ ID NO:46 | AITGSGGSTYYADSVKG | SEQ ID NO:52 |
| 1D11 | GTIPMS | SEQ ID NO:47 | SISGSAGSTYYADSVKG | SEQ ID NO:53 |
| 1B11 | SRDALN | SEQ ID NO:48 | AISGSGGSTFYADSVKG | SEQ ID NO:54 |
| 2A5 | SRYAMN | SEQ ID NO:49 | AISASGGGTYYADSVKG | SEQ ID NO:55 |
| 2D4 | RKYAMG | SEQ ID NO:50 | GISGSVGSTYYADSVKG | SEQ ID NO:56 |
| 1H7 | RRYAMS | SEQ ID NO:51 | GISGSGGGTYYADSVKG | SEQ ID NO:57 |
| 1D8 | SRYAMN | SEQ ID NO:49 | AINASGGSTYYADSVKG | SEQ ID NO:58 |

Figure 9B

```
32H4 VH  EVQLLESGGGLVQPGGSLRLSCAASGFTF SSYAMS WVRQAPGKGLEWVS AISGSGGSTYYADSVKG RFTI
5G3      EVQLLESGGGLVQPGGSLRLSCAASGFTF SSYVLS WVRQAPGKGLEWVS AIRGSAGNTYYADSVKG RFTI
5D7      EVQLLESGGGLVQPGGSLRLSCAASGFTF SNYAMS WVRQAPGKGLEWVS GIRSSGGRTFYADSVKG RFTI

32H4 VH  SRDNSKNTLYLQMNSLRAEDTAVYYCAR VAFSGSFDY WGQGTLVTVSS SEQ ID NO:6
5G3      SRDNSKNTLYLQMNSLRAEDTAVYYCAR VAFSGSFDY WGQGTLVTVSS SEQ ID NO:59
5D7      SRDNSKNTLYLQMNSLRAEDTAVYYCAR VAFSGSFDY WGQGTLVTVSS SEQ ID NO:61
```

Figure 9C

| Clone | HCDR1 | Sequence | HCDR2 | Sequence |
|---|---|---|---|---|
| 32H4 VH | SSYAMS | SEQ ID NO:9 | AISGSGGSTYYADSVKG | SEQ ID NO:10 |
| 5G3 | SSYVLS | SEQ ID NO:63 | AIRGSAGNTYYADSVKG | SEQ ID NO:65 |
| 5D7 | SNYAMS | SEQ ID NO:64 | GIRSSGGRTFYADSVKG | SEQ ID NO:66 |

Figure 9D

| Clone | ka (1/Ms) | kd (1/s) | KD (M) | Notes |
|---|---|---|---|---|
| 5D7 | 8.22E+04 | 4.43E-04 | 5.40E-09 | Parent clone 32H4 |
| 2C7 | 7.57E+04 | 4.10E-04 | 5.42E-09 | Parent clone 31C2 |
| 5G3 | 7.03E+04 | 5.86E-04 | 8.34E-09 | Parent clone 32H4 |
| 2D4 | 8.35E+04 | 7.45E-04 | 8.92E-09 | Parent clone 31C2 |
| 1D11 | 3.90E+04 | 3.86E-04 | 9.89E-09 | Parent clone 31C2 |
| 2D3 | 4.47E+04 | 4.55E-04 | 1.02E-08 | Parent clone 31C2 |
| 1H7 | 6.32E+04 | 7.65E-04 | 1.21E-08 | Parent clone 31C2 |
| 1D8 | 6.60E+04 | 9.11E-04 | 1.38E-08 | Parent clone 31C2 |
| 2A5 | 4.24E+04 | 6.56E-04 | 1.55E-08 | Parent clone 31C2 |
| 1B11 | 4.60E+04 | 8.03E-04 | 1.75E-08 | Parent clone 31C2 |
| 32H4 | 1.40E+05 | 0.00897 | 6.43E-08 | |
| 31C2 | 1.50E+05 | 0.01194 | 7.96E-08 | |

Figure 10A

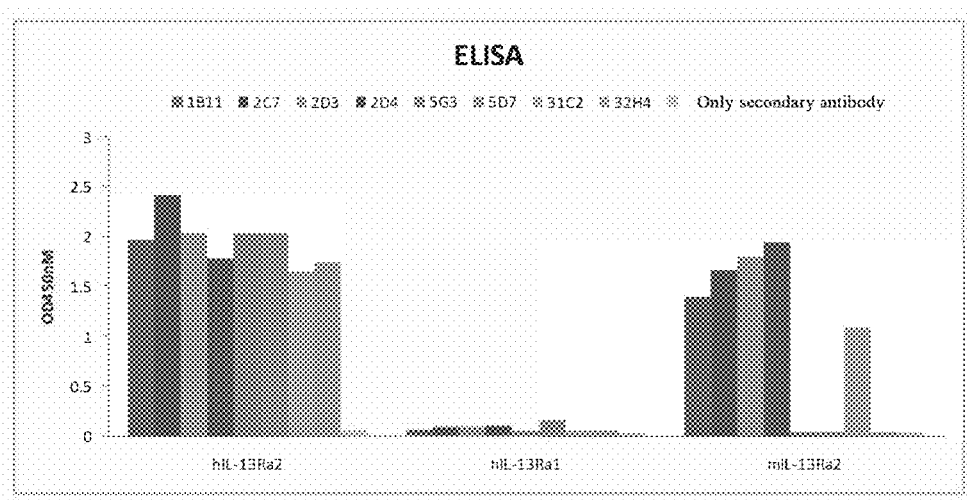
Fig. 10B
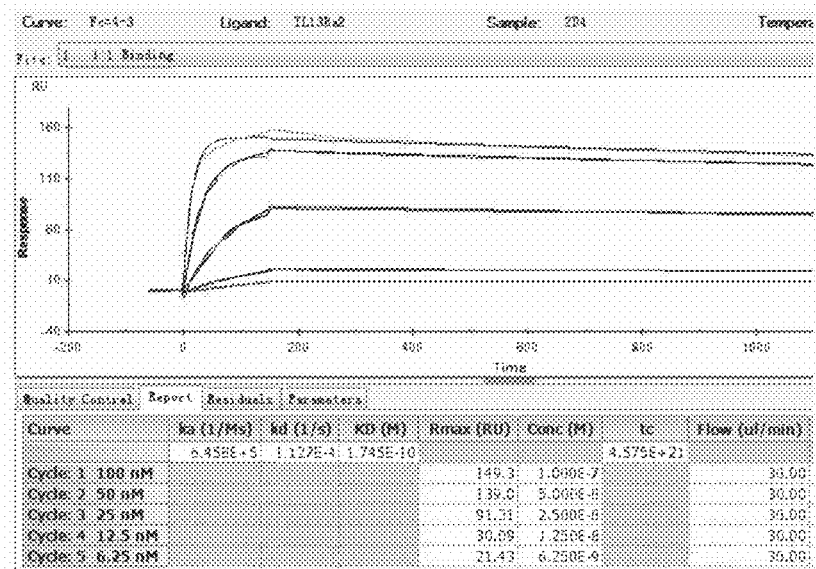
Fig. 11A
Fig. 11B

| Clone | ka (1/Ms) | kd (1/s) | KD (M) |
|---|---|---|---|
| 31C2 | 2.49E+05 | 4.45E-04 | 1.78E-09 |
| 2D4 | 6.46E+05 | 1.13E-04 | 1.74E-10 |
| 2C7 | 3.68E+05 | 9.15E-05 | 2.48E-10 |
| 2D3 | 5.63E+05 | 1.96E-04 | 3.48E-10 |
| 1B11 | 2.53E+05 | 2.63E-04 | 1.04E-09 |
|  |  |  |  |
| 32H4 | 2.32E+05 | 8.70E-04 | 3.76E-09 |
| 5G3 | 6.90E+05 | 1.34E-04 | 1.94E-10 |
| 5D7 | 7.37E+05 | 2.47E-04 | 3.35E-10 |

ANTIBODY TARGETING IL-13RA2 AND USE THEREOF

CROSS REFERENCE TO RELATED APPLICATIONS

This application is a National Phase application under 35 U.S.C. § 371 of International Application No. PCT/CN2018/075859, filed Feb. 8, 2018, which claims priority to Chinese Application No. 201710087299.2, filed Feb. 17, 2017, and Chinese Application No. 201810079015.X, filed Jan. 26, 2018, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 30, 2022, is named BCLS-009US-_SL.txt and is 75,617 bytes in size.

FIELD OF THE INVENTION

The invention relates to the field of tumor immunotherapy or diagnosis, and more particularly to an antibody that specifically recognizes IL-13RA2 and the use thereof.

BACKGROUND OF THE INVENTION

There are 20,000 new cases of malignant gliomas (MG), comprising pleomorphic glioblastoma and glioblastoma, each year in the United States. According to statistical data of the American Brain Oncology Association, as of 2010, 140,000 people in the United States have malignant brain tumors. Although MG is a rare disease, its malignancy and mortality are very high. The current standard treatment means have very limited effects, and the five-year survival rate after surgery and radiotherapy is also very low. For patients who have relapsed after surgery, there are very few new treatment options. Therefore, the development of new targets and new treatment means are urgent needs of the majority of patients.

Interleukin-13 receptor subunit alpha 2 (IL-13RA2) is a tumor-specific marker that is specifically highly expressed on the surface of a malignant tumor cell such as human glioma (Dehinski et al., (1995) Clin. Cancer Res. 1, 1253-1258) or the like. Human IL-13RA2 as a treatment target for human gliomas, has attracted the attention of the US FDA since 1988, and the organization has prepared the drug IL-13-PE38 for human IL-13RA2 as a treatment target and a single-chain antibody scFv-PE fusion molecule for human IL-13RA2 successively. Although IL-13-PE38 has achieved efficacy in the treatment of malignant tumors such as glioma, head and neck tumor, ovarian cancer and kidney cancer, and has been approved by the US FDA for clinical treatment; however, in the treatment process, IL-13-PE38 not only binds to human IL-13RA2 specifically expressed on the tumor cell surface, but also binds to IL13-RA1 expressed on the normal tissue cell surface, damaging normal tissues and cells. Further application of IL-13-PE38 is limited due to the lack of strict targeting.

The invention aims to find an antibody specific for IL-13RA2 and develop an immune effector cell targeting IL-13RA2.

SUMMARY OF THE INVENTION

It is an object of the invention to provide an antibody against IL-13RA2 and the use thereof.

In a first aspect, the invention provides an antibody that specifically recognizes IL-13RA2, wherein the relative binding affinity EC50 of the antibody to U251 cells endogenously expressing IL-13RA2 is not higher than 100 nM, preferably not higher than 10 nM, more preferably 0.01-10 nM.

In a preferred example, GraphPad Prism 5 software (GraphPad Software, Inc) is used in the processing of the relative affinity data.

In a specific embodiment, the antibody is selected from any of:

(1) an antibody comprising a heavy chain variable region comprising HCDR1 shown in SEQ ID NOs: 9, 45, 46, 47, 48, 49, 50, 51, 63, or 64, and/or HCDR2 shown in SEQ ID NOs: 10, 52, 53, 54, 55, 56, 57, 58, 65, or 66, and/or HCDR3 shown in any of SEQ ID NOs: 11 or 12;

(2) an antibody comprising a light chain variable region comprising LCDR1 shown in SEQ ID NO: 13, and/or LCDR2 shown in SEQ ID NO: 14, and/or LCDR3 shown in any of SEQ ID NOs: 15 or 16;

(3) an antibody comprising a heavy chain variable region of the antibody of (1) and a light chain variable region of the antibody of (2); and (4) an antibody which is a variant of the antibody according to any of (1) to (3), and has identical or similar activity to the antibody according to any of (1) to (3).

In a specific embodiment, the antibody is selected from any of:

(1) an antibody comprising a light chain variable region comprising an amino acid sequence shown in SEQ ID NO: 4, an amino acid sequence shown in SEQ ID NO: 8, or a sequence of a variant of SEQ ID NO: 4 and SEQ ID NO: 8;

(2) an antibody comprising a heavy chain variable region having a sequence shown in SEQ ID NOs: 2, 6, 29, 31, 33, 35, 37, 39, 41, 43, 59 or 61, or a variant of the sequence;

(3) an antibody comprising a heavy chain variable region of the antibody of (1) and a light chain variable region of the antibody of (2).

In a specific embodiment, the light chain variable region of the antibody comprises LCDR1 shown in SEQ ID NO: 13, LCDR2 shown in SEQ ID NO: 14, and LCDR3 shown in SEQ ID NO: 15 or SEQ ID NO: 16.

In a specific embodiment, the light chain variable region of the antibody has a sequence shown in SEQ ID NO: 4 or 8, or has a sequence with at least 80%, for example, 85%, 90%, 91%, 92%, 93%, 94%, 95%, 96%, 97%, 98%, and 99% similarity to any of the above sequences.

In a specific embodiment, the heavy chain variable region of the antibody comprises HCDR1 shown in SEQ ID NOs: 9, 45, 46, 47, 48, 49, 50, 51, 63 or 64, HCDR2 shown in SEQ ID NOs: 10, 52, 53, 54, 55, 56, 57, 58, 65 or 66, and HCDR3 shown in SEQ ID NO: 11 or SEQ ID NO: 12.

In a specific embodiment, the heavy chain variable region of the antibody has a sequence shown in SEQ ID NOs: 2, 6, 29, 31, 33, 35, 37, 39, 41, 43, 59 or 61, or has a sequence with at least 80%, more preferably 85%, 90%, 91%, 92%, 93%, 94%, 95%, 96%, 97%, 98%, and 99% similarity to any of the above sequences.

In a specific embodiment, the CDR regions of the light chain variable region and the CDR regions of the heavy chain variable region have the following optional sequences or variants thereof:

(1) LCDR1 shown in SEQ ID NO: 13, LCDR2 shown in SEQ ID NO: 14, and LCDR3 shown in SEQ ID NO: 15; HCDR1 shown in SEQ ID NO: 9, HCDR2 shown in SEQ ID NO: 10, and HCDR3 shown in SEQ ID NO: 11;

(2) LCDR1 shown in SEQ ID NO: 13, LCDR2 shown in SEQ ID NO: 14, and LCDR3 shown in SEQ ID NO: 16; HCDR1 shown in SEQ ID NO: 9, HCDR2 shown in SEQ ID NO: 10, and HCDR3 shown in SEQ ID NO: 12;

(3) LCDR1 shown in SEQ ID NO: 13, LCDR2 shown in SEQ ID NO: 14, and LCDR3 shown in SEQ ID NO: 16; HCDR1 shown in SEQ ID NO: 64, HCDR2 shown in SEQ ID NO: 66, and HCDR3 shown in SEQ ID NO: 12;

(4) LCDR1 shown in SEQ ID NO: 13, LCDR2 shown in SEQ ID NO: 14, and LCDR3 shown in SEQ ID NO: 15; HCDR1 shown in SEQ ID NO: 45, HCDR2 shown in SEQ ID NO: 52, and HCDR3 shown in SEQ ID NO: 11;

(5) LCDR1 shown in SEQ ID NO: 13, LCDR2 shown in SEQ ID NO: 14, and LCDR3 shown in SEQ ID NO: 16; HCDR1 shown in SEQ ID NO: 63, HCDR2 shown in SEQ ID NO: 65, and HCDR3 shown in SEQ ID NO: 12;

(6) LCDR1 shown in SEQ ID NO: 13, LCDR2 shown in SEQ ID NO: 14, and LCDR3 shown in SEQ ID NO: 15; HCDR1 shown in SEQ ID NO: 50, HCDR2 shown in SEQ ID NO: 56, and HCDR3 shown in SEQ ID NO: 11;

(7) LCDR1 shown in SEQ ID NO: 13, LCDR2 shown in SEQ ID NO: 14, and LCDR3 shown in SEQ ID NO: 15; HCDR1 shown in SEQ ID NO: 46, HCDR2 shown in SEQ ID NO: 52, and HCDR3 shown in SEQ ID NO: 11;

(8) LCDR1 shown in SEQ ID NO: 13, LCDR2 shown in SEQ ID NO: 14, and LCDR3 shown in SEQ ID NO: 15; HCDR1 shown in SEQ ID NO: 48, HCDR2 shown in SEQ ID NO: 54, and HCDR3 shown in SEQ ID NO: 11;

(9) LCDR1 shown in SEQ ID NO: 13, LCDR2 shown in SEQ ID NO: 14, and LCDR3 shown in SEQ ID NO: 15; HCDR1 shown in SEQ ID NO: 47, HCDR2 shown in SEQ ID NO: 53, and HCDR3 shown in SEQ ID NO: 11;

(10) LCDR1 shown in SEQ ID NO: 13, LCDR2 shown in SEQ ID NO: 14, and LCDR3 shown in SEQ ID NO: 15; HCDR1 shown in SEQ ID NO: 49, HCDR2 shown in SEQ ID NO: 55, and HCDR3 shown in SEQ ID NO: 11;

(11) LCDR1 shown in SEQ ID NO: 13, LCDR2 shown in SEQ ID NO: 14, and LCDR3 shown in SEQ ID NO: 15; HCDR1 shown in SEQ ID NO: 51, HCDR2 shown in SEQ ID NO: 57, and HCDR3 shown in SEQ ID NO: 11; or

(12) LCDR1 shown in SEQ ID NO: 13, LCDR2 shown in SEQ ID NO: 14, and LCDR3 shown in SEQ ID NO: 15; HCDR1 shown in SEQ ID NO: 49, HCDR2 shown in SEQ ID NO: 58, and HCDR3 shown in SEQ ID NO:11.

In a specific embodiment, (1) the light chain variable region has a sequence shown in SEQ ID NO: 4 or a sequence of a variant thereof, and the heavy chain variable region has a sequence shown in SEQ ID NO: 2 or a sequence of a variant thereof;

(2) the light chain variable region has a sequence shown in SEQ ID NO: 8 or a sequence of a variant thereof, and the heavy chain variable region has a sequence shown in SEQ ID NO: 6 or a sequence of a variant thereof;

(3) the light chain variable region has a sequence shown in SEQ ID NO: 8 or a sequence of a variant thereof, and the heavy chain variable region has a sequence shown in SEQ ID NO: 61 or a sequence of a variant thereof;

(4) the light chain variable region has a sequence shown in SEQ ID NO: 4 or a sequence of a variant thereof, and the heavy chain variable region has a sequence shown in SEQ ID NO: 29 or a sequence of a variant thereof;

(5) the light chain variable region has a sequence shown in SEQ ID NO: 8 or a sequence of a variant thereof, and the heavy chain variable region has a sequence shown in SEQ ID NO: 59 or a sequence of a variant thereof;

(6) the light chain variable region has a sequence shown in SEQ ID NO: 4 or a sequence of a variant thereof, and the heavy chain variable region has a sequence shown in SEQ ID NO: 39 or a sequence of a variant thereof;

(7) the light chain variable region has a sequence shown in SEQ ID NO: 4 or a sequence of a variant thereof, and the heavy chain variable region has a sequence shown in SEQ ID NO: 31 or a sequence of a variant thereof;

(8) the light chain variable region has a sequence shown in SEQ ID NO: 4 or a sequence of a variant thereof, and the heavy chain variable region has a sequence shown in SEQ ID NO: 35 or a sequence of a variant thereof;

(9) the light chain variable region has a sequence shown in SEQ ID NO: 4 or a sequence of a variant thereof, and the heavy chain variable region has a sequence shown in SEQ ID NO: 33 or a sequence of a variant thereof;

(10) the light chain variable region has a sequence shown in SEQ ID NO: 4 or a sequence of a variant thereof, and the heavy chain variable region has a sequence shown in SEQ ID NO: 37 or a sequence of a variant thereof;

(11) the light chain variable region has a sequence shown in SEQ ID NO: 4 or a sequence of a variant thereof, and the heavy chain variable region has a sequence shown in SEQ ID NO: 41 or a sequence of a variant thereof; or

(12) the light chain variable region has a sequence shown in SEQ ID NO: 4 or a sequence of a variant thereof, and the heavy chain variable region has a sequence shown in SEQ ID NO: 43 or a sequence of a variant thereof.

In a second aspect, the invention provides an antibody that specifically recognizes IL-13RA2, wherein the antibody recognizes the same antigenic determinant as the antibody of the first aspect.

In a third aspect, the invention provides an antibody that specifically recognizes IL-13RA2, wherein the antibody competitively binds to IL-13RA2 with the antibody of the first aspect.

In a fourth aspect, the invention provides a nucleic acid encoding the antibody of the first to third aspects.

In a fifth aspect, the invention provides an expression vector comprising the nucleic acid of the fourth aspect.

In a sixth aspect, the invention provides a host cell comprising the expression vector of the fifth aspect or having the nucleic acid of the fourth aspect integrated in the genome.

In a seventh aspect, the invention provides a multifunctional immunoconjugate comprising:

the antibody of the first to third aspects; and a functional molecule linked thereto; the functional molecule being selected from a molecule that targets a tumor surface marker, a molecule that inhibits a tumor, a molecule that targets an immune cell surface marker, or a detectable label.

In a specific embodiment, the molecule that targets a tumor surface marker is an antibody or ligand that binds to a tumor surface marker other than IL-13RA2; or the molecule that inhibits a tumor is an anti-tumor cytokine or an anti-tumor toxin; preferably, the cytokine is selected from IL-12, IL-15, type I interferon, and TNF-alpha.

In a specific embodiment, the molecule that targets an immune cell surface marker is an antibody that binds to an immune cell surface marker, preferably, the bound immune cell surface marker is selected from CD3, CD16 and CD28, and more preferably, the antibody that binds to the immune cell surface marker is an anti-CD3 antibody.

In a specific embodiment, the molecule that targets the immune cell surface marker is an antibody that binds to a T cell surface marker, and forms a bifunctional antibody with the antibody of any of the first to third aspects in which T cells are involved, In a specific embodiment, the multifunctional immunoconjugate is a fusion polypeptide further comprising a linker peptide between the antibody of any of the first to third aspects, and the functional molecule linked thereto.

In an eighth aspect, the invention provides a nucleic acid encoding the multifunctional immunoconjugate of the seventh aspect.

In a ninth aspect, the invention provides the chimeric antigen receptor of the antibody of the first to third aspects, wherein the chimeric antigen receptor comprises the antibody of the first to third aspects, a transmembrane region, and an intracellular signaling region connected sequentially.

In a specific embodiment, the intracellular signaling region is selected from functional signaling domains of proteins CD3ζ, CD3γ, CD3δ, CD3ε, FcRγ (FCER1G), FcRβ (FcεR1b), CD79a, CD79b, FcγRIIa, DAP10 and DAP12, or a combination thereof.

In a specific embodiment, the intracellular signaling region further has a costimulatory signaling domain, and the costimulatory signaling domain comprises a functional signaling domain of a protein selected from: CD27, CD28, 4-1BB(CD137), OX40, CD30, CD40, PD-1, ICOS, lymphocyte function associated antigen-1 (LFA-1), CD2, CD7, LIGHT, NKG2C, B7-H3, a ligand specifically binding to CD83, CDS, ICAM-1, GITR, BAFFR, HVEM (LIGHTR), SLAMF7, NKp80 (KLRF1), CD160, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244,2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46 and NKG2D, or a combination thereof.

In a specific embodiment, the chimeric antigen receptor comprises an antibody, a transmembrane region and an intracellular signaling region connected sequentially as follows:

the antibody of the first to third aspects, CD8 and CD3ζ;

the antibody of the first to third aspects, CD8, CD137 and CD3ζ; or the antibody of the first to third aspects, the transmembrane region of CD28 molecule, the intracellular signaling region of CD28 molecule, and CD3ζ; or the antibody of the first to third aspects, the transmembrane region of CD28 molecule, the intracellular signaling region of CD28 molecule, CD137 and CD3ζ.

In a tenth aspect, the invention provides a nucleic acid encoding the chimeric antigen receptor of the ninth aspect.

In an eleventh aspect, the invention provides an expression vector comprising the nucleic acid of the tenth aspect.

In a twelfth aspect, the invention provides a virus comprising the vector of the eleventh aspect.

In a thirteenth aspect, the invention provides a chimeric antigen receptor-modified immune cell, wherein the immune cell is transduced with the nucleic acid of the tenth aspect, or the expression vector of the eleventh aspect or the virus of the twelfth aspect; or expresses the chimeric antigen receptor of the ninth aspect on the surface;

preferably, the immune cell is: a T lymphocyte, an NK cell or an NKT lymphocyte.

In a specific embodiment, the immune cell further carries a coding sequence of an exogenous cytokine; or the immune cell further expresses another chimeric antigen receptor that does not contain CD3ζ; or the immune cell further expresses a chemokine receptor; preferably, the chemokine receptor comprises CCR; or the immune cell further expresses an siRNA that reduces expression of PD-1 or a protein that blocks PD-L1; or endogenous PD-1 in the immune cell is knocked out by the gene editing technology; or the immune cell further expresses a safety switch.

In a fourteenth aspect, the invention provides a pharmaceutical composition, comprising:

the antibody of the first to third aspects or a nucleic acid encoding the antibody; or the immunoconjugate of the seven aspect or a nucleic acid encoding the immunoconjugate; or the chimeric antigen receptor of the ninth aspect or a nucleic acid encoding the chimeric antigen receptor; or the chimeric antigen receptor-modified immune cell of the thirteenth aspect;

and a pharmaceutically acceptable carrier or excipient.

In a fifteenth aspect, the invention provides a kit, comprising:

a container, and the pharmaceutical composition of the fourteenth aspect in the container; or a container, and the antibody of the first to third aspects or a nucleic acid encoding the antibody in the container; or the immunoconjugate of the seventh aspect or a nucleic acid encoding the immunoconjugate; or the chimeric antigen receptor of the ninth aspect or a nucleic acid encoding the chimeric antigen receptor; or the chimeric antigen receptor-modified immune cell of the thirteenth aspect.

In a sixteenth aspect, the invention provides the use of the antibody of the first to third aspects or a nucleic acid encoding the antibody; or the immunoconjugate of the seventh aspect or a nucleic acid encoding the immunoconjugate; or the chimeric antigen receptor of the ninth aspect or a nucleic acid encoding the chimeric antigen receptor; or the use of the chimeric antigen receptor-modified immune cell of the thirteenth aspect for treating a tumor expressing IL-13RA2, preferably, the tumor expressing IL-13RA2 is brain cancer, pancreatic cancer, ovarian cancer, kidney cancer, bladder cancer, pancreatic cancer, gastric cancer, intestinal cancer, head and neck cancer, thyroid cancer, prostate cancer, and Kaposi's sarcoma. More preferably, the brain cancer is selected from astrocytoma, meningioma, oligodendroglioma, and glioma.

It should be understood that all of the various technical features described above and specifically described hereinafter (such as examples) can be combined with one another within the scope of the invention, so as to form new or preferred technical solutions. Due to space limitations, these are no longer tired out one by one.

DESCRIPTION OF FIGURES

FIG. 6 shows detection of EC50 of binding of antibodies 31C2 and 32H4 to U215 cells by FACs;

FIG. 7 shows primer information for affinity maturation;

FIG. 8 shows the dissociation constant Kd of 10 clones screened after affinity maturation;

FIG. 9A shows the heavy chain sequence alignment of the affinity matured clones of 31C2, FIG. 9B shows sequences of HCDR1 and HCDR2 of the affinity matured clones of 31C2, FIG. 9C shows the heavy chain sequence alignment of affinity matured clones of 32H4, and FIG. 9D shows sequences of HCDR1 and HCDR2 of affinity matured clones of 32H4;

FIG. 10A shows the association and dissociation constants of affinity matured antibodies; and FIG. 10B shows the specific identification results of antibodies 5D7, 2C7, 5G3, 2D4, 2D3, and 1B11;

FIG. 11A shows the results of yields of scFv_Fc forms of the antibodies in 30 ml expression systems and the aggregation degree assay of purified products after affinity maturation;

FIGS. 11B-G show the affinity of scFv_Fc forms of the antibodies; and FIG. 11H shows the results of the association and dissociation constants of the antibodies;

DETAILED DESCRIPTION OF THE INVENTION

Figure 1:
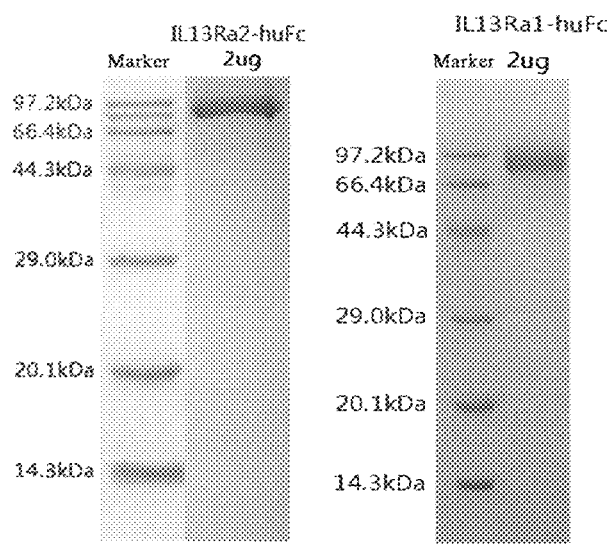
FIG. 1 shows an SDS electropherogram (reduction conditions) of IL-13RA2 huFc, and IL13RA1_huFc.

The inventors obtain antibodies that specifically recognize IL-13RA2, comprising single-chain antibodies and humanized antibodies, by intensive research and screening. The antibody of the invention can be used in the manufacture of various targeting anti-tumor medicaments as well as medicaments for diagnosing a tumor.

In order to make the invention easier to be understood, some terms are first defined.

The term "IL-13RA2", also referred to herein as CD213A2, is a subunit of the interleukin-13 receptor complex. It is a transmembrane protein consisting of 380 amino acid residues (NCBI Reference Sequence: NP_000631.1). It is similar to IL-13RA1 (NCBI Reference Sequence: NP_001551.1) and binds strongly to IL-13 but has no intracellular signaling domain.

The term "antibody" herein refers to an antigen binding protein of an immune system; and comprises an intact full length antibody having an antigen binding region, and also a fragment having an "antigen binding portion" or an "antigen binding region", or a single chain thereof such as a single chain variable fragment (scFv), as well as a variant of the antibody provided herein. The antibody fragment includes, but is not limited to: (i) an Fab fragment which consists of VL, VH, CL and CH1 domains and includes Fab' and Fab'-SH, (ii) an Fd fragment consisting of VH and CH1 domains, (iii) an Fv fragment consisting of VL and VH domains of a single antibody; (iv) a dAb fragment consisting of a single variable region (Ward et al., 1989, Nature 341: 544-546); (v) an F(ab')2 fragment which is a bivalent fragment comprising two linked Fab fragments; (vi) a single-chain Fv molecule antigen-binding site; (vii) a bispecific single-chain Fv dimer (PCT/US 92/09965); (viii) "diabody" or "triabody", a multivalent or multispecific fragment constructed by genetic fusion; and (ix) an scFv genetically fused to the same or a different antibody.

The term "Fc" or "Fc region" herein comprises a polypeptide comprising an antibody constant region other than the first constant region immunoglobulin domain. Thus, Fc refers to the last two constant region immunoglobulin domains of IgA, IgD and IgG, the last three constant region immunoglobulin domains of IgE and IgM, and flexible hinges at the N-termini of these domains. For IgA and IgM, Fc can comprise J chain. For IgG, Fc comprises immunoglobulin domains Cγ2 and Cγ3, and a hinge between Cγ1 and Cγ2. Although the boundaries of the Fc region may vary, the human IgG heavy chain Fc region is generally defined as comprising residue C226 or P230 at its carboxy terminus, wherein the numbering is based on the EU index of Kabat. For human IgG1, Fc is defined herein to comprise residue P232 to its carboxy terminus, wherein the numbering is based on the EU index of Kabat. Fc may refer to an isolated region, or a region in an Fc polypeptide (such as an antibody) environment. The above-mentioned "hinge" comprises a flexible polypeptide containing amino acids between the first and second constant domains of the antibody. Structurally, the IgG CH1 domain ends at position EU220, and the IgG CH2 domain begins at residue EU237. Thus, for IgG, the antibody hinge herein is defined to comprise positions 221 (D221 of IgG1) to 231 (A231 of IgG1), wherein the numbering is based on the EU index of Kabat.

The term "variant" refers to one or more active polypeptides which have substantially the same amino acid sequence, or are coded by substantially the same nucleotide sequence, as the sequence of the antibody provided in the present application. The variant has the same or similar activity as the antibody provided in the examples of the present application.

A variant has at least one amino acid modification as compared with a parent antibody. In a specific embodiment, the variant sequence herein preferably has at least about 80%, most preferably at least about 90%, more preferably at least about 95%, more preferably at least about 98%, and most preferably at least about 99% amino acid sequence identity with the parent antibody sequence. The variant may refer to the antibody itself, and may also refer to a composition comprising a parent antibody. The term "amino acid modification" comprises amino acid substitutions, additions and/or deletions, an "amino acid substitution" means a replacement of an amino acid at a specific position in a parent polypeptide sequence with another amino acid, an "amino acid insertion" means an addition of an amino acid at a specific position in a parent polypeptide sequence, and an "amino acid deletion" or "deletion" means removal of an amino acid at a specific position in the parent polypeptide sequence.

An "amino acid modification" can be introduced into the antibody of the invention by standard techniques known in the art, such as site-directed mutagenesis and PCR-mediated mutagenesis. A conservative amino acid substitution is a substitution in which an amino acid residue is replaced with an amino acid residue which has a similar side chain. Families of amino acid residues having similar side chains have been defined in the art. These families comprise amino acids with basic side chains (e.g. lysine, arginine, and histidine), with acidic side chains (e.g. aspartic acid and glutamic acid), with uncharged polar side chains (e.g. glycine, asparagine, serine, threonine, tyrosine, cysteine, and tryptophan), with non-polar side chains (e.g. alanine, valine, leucine, isoleucine, proline, phenylalanine, and methionine), with (3-branched side chains (e.g. threonine, valine, and isoleucine), and with aromatic side chains (e.g. tyrosine, phenylalanine, tryptophan, and histidine). Thus, one or more amino acid residues in CDR regions or in framework regions of the antibody of the invention can be replaced with other amino acid residues belonging to the same side chain families, and the function retained by the altered antibody (variant antibody) can be tested.

The term "parent antibody" as mentioned above refers to an antibody provided by the present application or an antibody obtained by mutation, affinity maturation or other processing means based on the antibody provided by the present application, and preferably refers to the antibodies shown in the examples. The parent antibody can be a naturally occurring antibody, or a variant or modified version of a naturally occurring antibody. A parent antibody can refer to the antibody itself, a composition comprising the parent antibody, or the coding amino acid sequence of the parent antibody.

The term "antigenic determinant" as used herein, is also referred to as an antigenic epitope, may be composed of a contiguous sequence of the IL-13RA2 protein sequence or may be composed of a non-contiguous three-dimensional structure of the IL-13RA2 protein sequence.

Anti-IL-13RA2 Antibody

In the present disclosure, an antigen binding protein, including an antibody, having an antigen binding region based on scFv, is described. The scFv was selected from the human scFv phage display library using recombinant IL-13RA2. These molecules display fine specificity. For example, the antibody only recognizes IL-13RA2 and does not recognize IL-13RA1. In the invention, IL-13RA2 refers to human IL-13RA2, unless otherwise specified.

In some embodiments, the invention encompasses an antibody having a scFv sequence fused to one or more heavy chain constant regions to form an antibody having a human immunoglobulin Fc region to produce a bivalent protein, thereby increasing the overall affinity and stability of the antibody. In addition, the Fc portion allows for direct conjugation of other molecules (including, but not limited to, fluorescent dyes, cytotoxins, radioisotopes, etc.) to, for example, antibodies used in the antigen quantification study, in order to immobilize the antibodies for affinity measurement, for targeted delivery of a therapeutic agent, for detection of Fc-mediated cytotoxicity using immune effector cells, and many other applications.

The results presented herein highlight the specificity, sensitivity, and utility of the antibody of the invention in targeting IL-13RA2.

The molecule of the invention is based on a single-chain variable fragment (scFv) identified and selected using phage display, the amino acid sequence of the single-chain variable fragment confers specificity to the molecule against IL-13RA2 and forms the basis of all antigen binding proteins of the present disclosure. Thus, the scFv can be used to design a series of different "antibody" molecules including, for example, full length antibodies, fragments thereof such as Fab and F(ab')2, fusion proteins (including scFv_Fc), and multivalent antibodies, i.e., antibodies having more than one specificities for the same antigen or different antigens, for example, bispecific T-cell engager (BiTE), triabodies, and the like (see Cuesta et al. Multivalent antibodies: when design surpasses evolution, Trends in Biotechnology 28: 355-362, 2010).

In one embodiment where the antigen binding protein is a full length antibody, the heavy and light chains of the antibody of the invention may be full length (e.g. the antibody may comprise at least one, preferably two, intact heavy chains, and at least one, preferably two, intact light chains); or an antigen binding moiety (Fab, F(ab')2, Fv or scFv) may be encompassed. In other embodiments, the antibody heavy chain constant region is selected from, for example, IgG1, IgG2, IgG3, IgG4, IgM, IgA1, IgA2, IgD, and IgE. The choice of antibody type will depend on the immune effector function that the designed antibody is intended to elicit. Suitable amino acid sequences for the constant regions of various immunoglobulin isotypes and methods for producing a wide variety of antibodies in the construction of recombinant immunoglobulins are known to those skilled in the art.

In a first aspect, the invention provides an antibody that specifically recognizes IL-13RA2, which has a relative binding affinity EC50 of less than 100 nM, preferably less than 10 nM, more preferably 0.1-1 nM, and most preferably 0.3-0.6 nM, for U251 cells stably transfected with human IL-13RA2.

In a preferred embodiment, the antibody of IL-13RA2 provided by the invention comprises: a heavy chain CDR1 comprising an amino acid sequence of SEQ ID NO: 9, and/or a heavy chain CDR2 comprising an amino acid sequence of SEQ ID NO: 10, and/or a heavy chain CDR3 comprising an amino acid sequence of SEQ ID NO: 11 or 12. In another preferred embodiment, the antibody that binds to IL-13RA2 provided by the invention comprises: a light chain CDR1 comprising an amino acid sequence of SEQ ID NO: 13, and/or a light chain CDR2 comprising an amino acid sequence of SEQ ID NO: 14, and/or a light chain CDR3 comprising an amino acid sequence of SEQ ID NO: 15 or 16. In another preferred embodiment, the invention provides an antibody that binds to IL-13RA2, comprising: a heavy chain CDR1 comprising an amino acid sequence of SEQ ID NO: 9, and/or a heavy chain CDR2 comprising an amino acid sequence of SEQ ID NO: 10 and/or a heavy chain CDR3 comprising an amino acid sequence of SEQ ID NO: 11 or 12, and a light chain CDR1 comprising an amino acid sequence of SEQ ID NO: 13, and/or a light chain CDR2 comprising an amino acid sequence of SEQ ID NO: 14, and/or a light chain CDR3 comprising an amino acid sequence of SEQ ID NO: 15 or 16. Preferably, the antibody that binds to IL-13RA2 comprises: HCDR1 shown in SEQ ID NO: 9, HCDR2 shown in SEQ ID NO: 10, HCDR3 shown in SEQ ID NO: 11, LCDR1 shown in SEQ ID NO: 13, LCDR2 shown in SEQ ID NO: 14, and LCDR3 shown in SEQ ID NO: 15; or comprises HCDR1 shown in SEQ ID NO: 9, HCDR2 shown in SEQ ID NO: 10, HCDR3 shown in SEQ ID NO: 12, LCDR1 shown in SEQ ID NO: 13, LCDR2 shown in SEQ ID NO: 14, and LCDR3 shown in SEQ ID NO: 16.

More preferably, the antibody that binds to IL-13RA2 comprises HCDR1 shown in SEQ ID NO: 9, HCDR2 shown in SEQ ID NO: 10, HCDR3 shown in SEQ ID NO: 12, LCDR1 shown in SEQ ID NO: 13, LCDR2 shown in SEQ ID NO: 14, and LCDR3 shown in SEQ ID NO: 16.

In another aspect, the invention provides an antibody that binds to IL-13RA2, and the heavy chain variable region of the antibody is selected from a sequence of SEQ ID NO: 2 or SEQ ID NO: 6, or a sequence of a variant of either SEQ ID NO: 2 or SEQ ID NO: 6.

In another aspect, the invention provides an antibody or fragment thereof that binds to IL-13RA2, comprising a light chain variable region sequence selected from SEQ ID NO: 4 or SEQ ID NO: 8.

Given that these heavy and light chain variable region sequences can bind to IL-13RA2 individually, the heavy and light chain variable region sequences can be "mixed and matched" to produce the anti-IL-13RA2 binding molecule of the invention.

In another aspect, the invention provides a variant of an antibody or fragment thereof that binds to IL-13RA2. Thus, the invention provides an antibody or fragment thereof having a heavy chain and/or light chain variable region that is at least 80% identical to a heavy or light chain variable region sequence. Preferably, the amino acid sequence identity of the heavy and/or light chain variable region is at least 85%, more preferably at least 90%, most preferably at least 95%, particularly 96%, more particularly 97%, even more particularly 98%, the most particularly 99%, including, for example, 80%, 81%, 82%, 83%, 84%, 85%, 86%, 87%, 88%, 89%, 90%, 91%, 92%, 93%, 94%, 95%, 96%, 97%, 98%, 99% and 100%. The variant can be obtained by yeast library screening, phage library screening, point mutation and other means, using the antibody in the present application as a parent antibody.

In another aspect, the invention provides an antibody that recognizes the same antigenic determinant as the anti-IL-13RA2 antibody described above.

Properties of the Anti-IL-13RA2 Antibody

Standard assays for assessing the binding ability of an antibody, such as an antibody against IL-13RA2, are known in the art and comprise, for example, ELISA, biacore, Western blot, and flow cytometry analysis. Suitable assays are described in detail in examples.

Nucleic Acids, Vectors and Host Cells

The invention further provides a nucleic acid and a vector encoding an antibody and fragment thereof that binds to IL-13RA2; and a host cell comprising the nucleic acid or the vector. The nucleic acid can be located in an intact cell and in a cell lysate, or present in a partially purified or substantially purified form.

The nucleic acid of the invention can be obtained using standard molecular biology techniques, for example, by standard PCR amplification or cDNA cloning techniques to obtain cDNAs encoding the light and heavy chains or the VH and VL segments of antibody. For an antibody obtained from immunoglobulin gene libraries (e.g. using the phage display technology), one or more nucleic acids encoding the antibody can be recovered from the library. A method for introducing an exogenous nucleic acid into a host cell is well known in the art and can vary with the host cell used.

Preferred nucleic acid molecules of the invention are those encoding a light chain variable region selected from SEQ ID NO: 3 or SEQ ID NO: 7, and/or a heavy chain variable region selected from SEQ ID NO: 1 or SEQ ID NO: 5. More preferred is a nucleic acid molecule comprising a heavy chain sequence of SEQ ID NO: 1 and a light chain sequence of SEQ ID NO: 3, or a heavy chain sequence of SEQ ID NO: 5 and a light chain sequence of SEQ ID NO: 7.

For expression of a protein, a nucleic acid encoding the antibody of the invention can be integrated into an expression vector. A variety of expression vectors are available for protein expression. Expression vectors may comprise self-replicating extra-chromosomal vectors, or vectors integrated into the host genome. Expression vectors for use in the invention include, but are not limited to, those which enable expression of proteins in mammalian cells, bacteria, insect cells, yeast, and in vitro systems. As is known in the art, a variety of expression vectors are commercially available or obtained in other ways, and can be used in the invention to express antibodies.

Immunoconjugates

The invention further provides a multifunctional immunoconjugate comprising the antibody described herein and further comprising at least one other type of functional molecule. The functional molecule is selected from, but is not limited to, a molecule that targets a tumor surface marker, a molecule that inhibits a tumor, a molecule that targets an immune cell surface marker, or a detectable label. The antibody and the functional molecule may constitute a conjugate by covalent linkage, coupling, attachment, cross-linking, and the like.

In a preferred mode, the immunoconjugate may comprise: an antibody of the invention and at least one molecule that targets a tumor surface marker or a molecule that inhibits a tumor. The molecule that inhibits a tumor may be an anti-tumor cytokine or an anti-tumor toxin; preferably, the cytokine includes but is not limited to IL-2, IL-7, IL-12, IL-15, type I IFN, and TNF-alpha. In a specific embodiment, the molecule that targets a tumor surface marker is a molecule that targets a surface marker of the same tumor to which the antibody of the invention is targeted. For example, the molecule that targets a tumor surface marker can be an antibody or ligand that binds to a tumor surface marker, for example, such molecule can cooperate with the antibody of the invention to more precisely target tumor cells. Optionally, As a preferred embodiment, the immunoconjugate may comprise: an antibody of the invention and a detectable label. The detectable label includes, but is not limited to: a fluorescent labels, a chromogenic label; such as an enzyme, a prosthetic group, a fluorescent material, a luminescent material, a bioluminescent material, a radioactive material, a positron emitting metal, and a non-radioactive paramagnetic metal ion. More than one label may also be included. The label used to label the antibody for detection and/or analysis and/or diagnostic purposes depends on the particular detection/analysis/diagnostic techniques and/or methods used, such as immunohistochemical staining of (tissue) samples, flow cytometry, and the like. Suitable labels for detection/analysis/diagnostic techniques and/or methods known in the art are well known to those skilled in the art.

As a preferred mode, the immunoconjugate may comprise: an antibody of the invention and a molecule that targets an immune cell surface marker. The molecule that targets an immune cell surface marker may be an antibody or a ligand that binds to an immune cell surface marker, and such molecule is capable of recognizing the immune cell, thereby carrying the antibody of the invention to the immune cell, then the antibody of the invention can target the immune cell to tumor cells, thereby inducing the immune cell-specific killing of tumors. The immune cell surface marker may be selected from CD3, CD16 and CD28, and more preferably, an antibody that binds to the immune cell surface marker is an anti-CD3 antibody. The immune cell can be selected from a T cell, an NK cell, and an NKT cell.

By way of chemical production of an immunoconjugate by direct or indirect (e.g. via a linker) conjugation, the immunoconjugate can be produced as a fusion protein comprising an antibody of the invention and another suitable protein. The fusion protein can be produced by a method known in the art, for example produced recombinantly by constructing and subsequently expressing a nucleic acid molecule, which comprises a nucleotide sequence encoding the antibody in accordance with the reading frame and a nucleotide sequence encoding a suitable label.

Another aspect of the invention provides a nucleic acid molecule encoding at least one antibody, a functional variant or an immunoconjugate thereof of the invention. Once the relevant sequence is obtained, the recombination method can be used to obtain the relevant sequence in large quantities. This is usually done by cloning the sequence into a vector, transferring it to a cell, and then isolating the relevant sequence from the proliferated host cell by conventional methods.

In another aspect, the invention provides a chimeric antigen receptor comprising an extracellular binding domain, a transmembrane domain, and an intracellular domain. The term "Chimeric Antigen Receptor (CAR)" used herein refers to a tumor antigen binding domain fused to an intracellular signal transduction domain, which can activate T cells. Typically, the extracellular binding domain of CAR is derived from a mouse or humanized or human monoclonal antibody.

The extracellular binding domain is an antibody of the invention, and non-limiting examples comprise a single-chain variable fragment (scFv) derived from an antibody, an antigen binding fragment (Fab) selected from a library, a single domain fragment, or a natural ligand engaging with the homologous receptor. In some embodiments, the extracellular antigen binding region can comprise a scFv, Fab, or a natural ligand, as well as any derivative thereof. The extracellular antigen binding region can refer to a molecule other than an intact antibody, which can comprise a portion of the intact antibody and can bind to an antigen to which the intact antibody binds. Examples of antibody fragments can include, but are not limited to, Fv, Fab, Fab', Fab'-SH, F(ab')2; a bifunctional antibody, a linear antibody; a single-chain antibody molecule (e.g., scFv); and a multispecific antibody formed from antibody fragments.

The extracellular antigen binding region, such as scFv, Fab or a natural ligand, can be part of a CAR that determines antigen specificity. The extracellular antigen binding region can bind to any complementary target. The extracellular antigen binding region can be derived from an antibody of known variable region sequence. The extracellular antigen binding region can be obtained from an antibody sequence obtained from an available mouse hybridoma. Alternatively, the extracellular antigen binding region can be obtained from whole exterior cleavage sequencing for a tumor cell or a primary cell such as a tumor infiltrating lymphocyte (TIL).

In some embodiments, the binding specificity of the extracellular antigen binding region can be determined by a complementarity determining region or CDR, such as a light chain CDR or a heavy chain CDR. In many cases, binding specificity can be determined by the light chain CDR and the heavy chain CDR. A combination of a given heavy chain CDR and a light chain CDR can provide a given binding pocket that can confer greater affinity and/or specificity for an antigen than other reference antigens.

In certain aspects of any of the embodiments disclosed herein, the extracellular antigen binding region, e.g. the scFv, can comprise a light chain CDR specific for an antigen. The light chain CDR can be a complementarity determining region of an scFv light chain of an antibody, such as a CAR. The light chain CDR may comprise a contiguous sequence of amino acid residues, or two or more contiguous sequences of amino acid residues separated by a non-complementarity determining region (e.g. a framework region). In some embodiments, a light chain CDR can comprise two or more light chain CDRs, which can be referred to as light chain CDR-1, CDR-2, and the like. In some embodiments, the light chain CDR can comprise three light chain CDRs, which can be referred to as light chain CDR-1, light chain CDR-2 and light chain CDR-3, respectively. In some examples, a set of CDRs present on a common light chain can be collectively referred to as a light chain CDR.

In certain aspects of any of the embodiments disclosed herein, the extracellular antigen binding region, e.g. the scFv, can comprise a heavy chain CDR that is specific for an antigen. The heavy chain CDR can be a heavy chain complementarity determining region of an antibody, such as a scFv. The heavy chain CDR may comprise a contiguous sequence of amino acid residues, or two or more contiguous sequences of amino acid residues separated by a non-complementarity determining region (e.g. a framework region). In some embodiments, the heavy chain CDR can comprise two or more heavy chain CDRs, which can be referred to as heavy chain CDR-1, CDR-2, and the like. In some embodiments, the heavy chain CDR can comprise three heavy chain CDRs, which can be referred to as heavy chain CDR-1, heavy chain CDR-2 and heavy chain CDR-3, respectively. In some embodiments, a set of CDRs present on a common heavy chain can be collectively referred to as a heavy chain CDR.

The extracellular antigen binding region can be modified in various ways by genetic engineering. In some embodiments, the extracellular antigen binding region can be mutated, so that the extracellular antigen binding region can be selected to have a higher affinity for its target. In some embodiments, the affinity of the extracellular antigen binding region for its target can be optimized for the target that can be expressed at a low level in a normal tissue. This optimization can be performed to minimize potential toxicity. In other instances, clones of the extracellular antigen binding region with a higher affinity for a membrane-bound form of a target may be preferred over the counterpart of a soluble form of the target. This modification can be made because different levels of a soluble form of the target can also be detected and the targeting to such form can cause undesirable toxicity.

In some embodiments, the extracellular antigen binding region comprises a hinge or a spacer. The terms hinge and spacer are used interchangeably. The hinge can be considered as a part of CAR for conferring flexibility to the extracellular antigen binding region. In some embodiments, the hinge can be used to detect a CAR on the cell surface of a cell, particularly when an antibody for detecting the extracellular antigen binding region is ineffective or not available. For example, the length of the hinge derived from an immunoglobulin may need to be optimized, depending on the location of an epitope on a target that is targeted by the extracellular antigen binding region.

In some embodiments, the hinge may not belong to an immunoglobulin, but belong to another molecule, such as a native hinge of a CD8a molecule. The CD8a hinge may contain cysteine and proline residues known to play a role in the interaction of the CD8 co-receptor and the MHC molecule. The cysteine and proline residues can affect the performance of the CAR.

The CAR hinge can be adjustable in size. This morphology of an immunological synapse between an immune response cell and a target cell also defines a distance that cannot be functionally bridged by the CAR due to a distal membrane epitope on a cell surface target molecule, in which case even the use of a short hinge CAR does not enable the synaptic distance to reach an an approximate value at which the signaling can be performed. Likewise, for the membrane proximal CAR target antigenic epitope, signal output is observed only in the context of a long hinge CAR. The hinge can be adjusted depending on the extracellular antigen binding region used. The hinge can be of any length.

The transmembrane domain can anchor a CAR to the plasma membrane of the cell. The natural transmembrane portion of CD28 can be used for a CAR. In other cases, the natural transmembrane portion of CD8a can also be used in the CAR. "CD8" may be a protein having at least 85%, 90%, 95%, 96%, 97%, 98%, 99% or 100% identity to the NCBI reference number: NP_001759 or a fragment thereof having stimulatory activity. A "CD8 nucleic acid molecule" may be a polynucleotide encoding a CD8 polypeptide, and in certain cases, the transmembrane region may be a natural transmembrane portion of CD28, and "CD28" may refer to a protein having at least 85%, 90%, 95%, 96%, 97%, 98%, 99% or 100% identity to the NCBI reference number: NP_006130 or a fragment thereof having stimulatory activity. A "CD28 nucleic acid molecule" can be a polynucleotide encoding a CD28 polypeptide. In some embodiments, the transmembrane portion can comprise a CD8a region.

The intracellular signaling region of a CAR may be responsible for activating at least one of effector functions of the immune response cells into which the CAR has been placed. A CAR can induce effector functions of T cells, for example, the effector function is cytolytic activity or helper activity, including secretion of cytokines. Thus, the term intracellular signaling region refers to a portion of a protein that transduces an effector function signal and directs the cell to perform a specific function. Although generally the entire intracellular signaling region can be used, in many cases it is not necessary to use the entire chain of the signaling domain. In some embodiments, a truncated portion of an intracellular signaling region is used. In some embodiments, the term intracellular signaling region is thus intended to include any truncated portion of an intracellular signaling region sufficient to transduce an effector function signal.

Preferred examples of a signaling domain for use in a CAR may include a cytoplasmic sequence of a T cell receptor (TCR) and a co-receptor that act synergistically to initiate signal transduction after target-receptor binding, as well as any derivative or variant sequence of both, and any synthetic sequence of these sequences that have the same functionality.

In some embodiments, the intracellular signaling region can contain a known signal motif of an immunoreceptor tyrosine activation motif (ITAM). Examples of ITAMs containing cytoplasmic signaling sequences include those derived from TCRζ, FcRγ, FcRβ, CD3γ, CD3δ, CD3ε, CD5, CD22, CD79a, CD79b, and CD66d. However, in a preferred embodiment, the intracellular signaling domain is derived from a CD3ζ chain.

An example of a T cell signaling domain containing one or more ITAM motifs is the CD3 domain, also known as the T cell receptor T3ζ chain or CD247. This domain is a part of a T cell receptor-CD3 complex and plays an important role in combining antigen recognition of several intracellular signal transduction pathways with the main effector activation of T cells. As used herein, CD3ζ primarily refers to human CD3ζ and its isoforms, as known from the Swissprot entry P20963, including a protein having substantially the same sequence. As a part of the chimeric antigen receptor, it is reiterated that the full T cell receptor T3ζ chain is not required and that any derivative comprising the signaling domain of the T cell receptor T3ζ chain is suitable, including any functional equivalent thereof.

The intracellular signaling domain can be selected from any one of the domains of Table 1. In some embodiments, the domain can be modified so that the identity to the reference domain can range from about 50% to about 100%. Any one domain of Table 1 can be modified so that the modified form can comprise about 50%, 60%, 70%, 80%, 90%, 95%, 96%, 97%, 98%, 99% or up to about 100% identity.

An intracellular signaling region of a CAR may further comprise one or more costimulatory domains. The intracellular signaling region may comprise a single costimulatory domain, such as a chain (the first generation CAR) or plus CD28 or 4-1BB (the second generation CAR). In other examples, the intracellular signaling region can comprise two costimulatory domains, such as CD28/OX40 or CD28/4-1BB (the third generation).

Together with the intracellular signaling domains such as CD8, these costimulatory domains can generate downstream activation of the kinase pathways, thereby supporting gene transcription and functional cellular responses. The co-stimulatory domains of CARs can activate proximal signal proteins associated with activation of CD28 (phosphatidylinositol-4,5-diphosphate 3-kinase) or 4-1BB/OX40 (TNF-receptor-associated factor adaptor) pathway as well as MAPK and Akt.

In certain cases, signals generated by the CAR may be combined with auxiliary or costimulatory signals. For costimulatory signaling domains, chimeric antigen receptor-like complexes can be designed to contain several possible costimulatory signaling domains. As well known in the art, in naive T cells, the individual engagement of T cell receptors is not sufficient to induce complete activation of T cells into cytotoxic T cells. A second co-stimulatory signal is required for complete productive T cell activation. Several receptors have been reported to provide co-stimulation for T cell activation, including, but not limited to, CD28, OX40, CD27, CD2, CD5, ICAM-1, LFA-1 (CD11a/CD18), 4-1BBL, MyD88, and 4-1BB. The signaling pathways used by these costimulatory molecules can act synergistically with the main T cell receptor activation signal. The signals provided by these costimulatory signaling regions can act synergistically with the main effector activation signals derived from one or more ITAM motifs (e.g. the CD3zeta signal transduction domain) and can fulfill the requirements for T cell activation.

In some embodiments, the addition of a costimulatory domain to a chimeric antigen receptor-like complex can enhance the efficacy and durability of engineered cells. In some other embodiments, the T cell signaling domain and the costimulatory domain are fused to each other to form a signaling region.

TABLE 4

Costimulatory domains

| Gene marker | Abbreviation | Name |
| --- | --- | --- |
| CD27 | CD27, T14, S152, Tp55, TNFRSF7, S152. LPFS2 | CD27 molecule |
| CD28 | Tp44, CD28, CD28 antigen | CD28 molecule |
| TNFRSF9 | ILA, 4-1BB, CD137, CDw137 | Tumor necrosis factor receptor superfamily member 9 |
| TNFRSF4 | OX40, ACT35, CD134, IMD16, TXGP1L | Tumor necrosis factor receptor superfamily member 4 |
| TNFRSF8 | CD30, Ki-1, D1S166E | Tumor necrosis factor receptor superfamily member 8 |
| CD40LG | IGM, IMD3, TRAP, gp39, CD154, CD40L, HIGM1, T-BAM, TNFSF5, hCD40L | CD40 ligand |
| ICOS | AILIM, CD278, CVID1 | Inducible T cell costimulator |
| ITGB2 | LAD, CD18, MF17, MFI7, LCAMB, LFA-1, MAC-1 | Integrin 132 (complement component 3 receptor 3 and 4 subunits) |
| CD2 | T11, SRBC, LFA-2 | CD2 molecule |
| CD7 | GP40, TP41, Tp40, LEU-9 | CD7 molecule |
| KLRC2 | NKG2C, CD159c, NKG2-C | Killer cell lectin-like receptor subfamily C, member 2 |
| TNFRSF18 | AITR, GITR, CD357, GITR-D | Tumor necrosis factor receptor superfamily member 18 |
| TNFRSF14 | TR2, ATAR, HVEA, HVEM, CD270, LIGHTR | Tumor necrosis factor receptor superfamily member 14 |
| HAVCR1 | TIM, KIM1, TIM1, CD365, HAVCR, KIM-1, TIM-1, TIMD1, TIMD-1, HAVCR-1 | Hepatitis A virus cell receptor 1 |
| LGALS9 | HUAT, LGALS9A, Galectin-9 | Lectin, galactoside-binding, soluble, 9 |
| CD83 | BL11, HB15 | CD83 molecule |

A chimeric antigen receptor binds to a target antigen. When T cell activation is measured in vitro or ex vivo, the target antigen can be obtained or isolated from various sources. A target antigen as used herein is an antigen or an antigenic epitope on the antigen that is critical in mammals for immune recognition and ultimate elimination or control of pathogenic factors or disease states. The immune recognition can be cellular and/or humoral immune recognition. In the case of intracellular pathogens and cancer, the immune recognition can be, for example, a T lymphocyte reaction.

In some embodiments, a target antigen comprises an antigen associated with a pre-cancerous or proliferative state. A target antigen may also be associated with or caused by cancer. For example, in some embodiments, a chimeric antigen receptor of the invention recognizes and binds to a tumor antigen comprising IL-13RA2 as described hereinbefore.

In some embodiments, when a chimeric antigen receptor is present on the plasma membrane of a cell, binds to its target and is activated, the cell expressing the chimeric antigen receptor can bring about cytotoxicity to the cell carrying the target. For example, in some embodiments, when the chimeric antigen receptor is present on a cytotoxic cell, such as an NK cell or a cytotoxic T cell, and activated by the target, the toxicity of the cytotoxic cell to the target cell can be increased. In some embodiments, a chimeric antigen receptor herein can increase the effect of immunoreactive cells on cells expressing IL-13RA2, such as tumor cells. In some embodiments, a cell expressing the chimeric antigen receptor described herein increases the cytotoxic effect on cells expressing IL-13RA2 by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 1-fold, at least 1.5-fold, at least 2-fold, at least 2.5-fold, at least 3-fold, at least 3.5-fold, at least 4-fold, at least 4.5-fold, at least 5-fold, at least 6-fold, at least 7-fold, at least 8-fold, at least 9-fold, or at least 10-fold than a cell that does not express the chimeric antigen receptor herein.

A transgene encoding an antigen binding receptor of interest or a CAR can be incorporated into a cell. For example, the transgene can be incorporated into an immune response cell, such as a T cell. When inserted into a cell, the transgene can be a complementary DNA (cDNA) fragment that is a copy of a messenger RNA (mRNA); or the gene itself (with or without introns) located in the original region of its genomic DNA.

A nucleic acid encoding the transgene sequence, such as a DNA, can be randomly inserted into the chromosome of the cell. Random integration can be produced by any method that introduces a nucleic acid, such as a DNA, into a cell. For example, the method can include, but is not limited to, electroporation, ultrasound, use of a gene gun, lipofection, calcium phosphate transfection, use of dendrimers, microinjection, and use of viral vectors including adenovirus, AAV, and retroviral vectors, and/or type II ribozyme.

The DNA encoding the transgene can also be designed to comprise a reporter gene, so that the presence of the transgene or its expression product can be detected by activation of the reporter gene. Any reporter gene can be used, such as those described above. The cells containing the transgene can be selected by selecting cells in the cell culture in which the reporter gene has been activated.

Expression of a CAR can be verified by expression assays such as qPCR or by measuring the level of RNAs. The expression level can also indicate the number of copies. For example, if the expression level is very high, this may indicate that more than one copy of the CAR is integrated into the genome. Alternatively, high expression may indicate that the transgene is integrated in a high transcription region, such as near a high expression promoter. The expression can also be verified by measuring protein levels, for example by Western blotting.

In some embodiments, the immune response cell of the invention may comprise one or more transgenes. The one or more transgenes can express a CAR protein that recognizes and binds to at least one epitope on an antigen or binds to a mutant epitope on the antigen. The CAR can be a functional CAR. In some embodiments, the immune response cells of the invention may comprise one or more CARs, or they may comprise a single CAR and a secondary engineered receptor.

In some embodiments, the transgene can encode a suicide gene. As evidenced by many effective treatments for cancer patients, CAR immune response cells cause tumor regression but can be accompanied with toxicity. In some embodiments, when a target antigen exists in both normal tissues and tumor cells, the CAR immune response cells may not be able to distinguish between tumors and normal tissues ("on-target/off-target toxicity"). In some other cases, a systemic disturbance of the immune system, called cytokine release syndrome (CRS), can occurs.

The CRS may comprise a systemic inflammatory response syndrome or a cytokine storm, which may be a consequence of rapid expansion of the CAR immune response cells in vivo. CRS is a disorder characterized by fever and hypotension, which can lead to multiple organ failure in a serious case. In most cases, the toxicity is associated with in vivo expansion of infused CAR immune response cells, which can cause an overall disturbance of the immune system, as well as release of high levels of pro-inflammatory cytokines such as TNFα and IL-6. The suicide gene can induce the elimination of CAR immunoreactive cells. The suicide gene may be any gene that induces apoptosis in the CAR immunoreactive cells. The suicide gene can be encoded in the viral vector together with the antigen binding receptor. The coding of the suicide gene allows for the mitigation or thorough termination of the toxicity caused by in vivo expansion of the infused CAR immune response cells under specific conditions.

In some embodiments, CAR immunoreactive cells for antigens that are present in normal tissues can be produced so that they transiently express the CAR, e.g. after introducing the mRNA encoding the receptor by electroporating. In addition, a major effort to further strengthen CAR immunoreactive cells by including a safety switch can greatly eliminate CAR immunoreactive cells in the case of severe target toxicity.

In some embodiments, a vector encoding the CAR can be combined with, for example, an inducible caspase-9 gene (activated by a dimeric chemical inducer) or a truncated form of EGF receptor R (activated by the monoclonal antibody cetuximab) or RQR8 safety switch.

One or more of the transgenes used herein may be from different species. For example, one or more of the transgenes can comprise a human gene, a mouse gene, a rat gene, a porcine gene, a bovine gene, a dog gene, a cat gene, a monkey gene, a chimpanzee gene, or any combination thereof. For example, a transgene can be from a human having a human genetic sequence. One or more of the transgenes may comprise a human gene. In certain cases, one or more of the transgenes are not adenoviral genes.

As described above, the transgene can be inserted into the genome of the immunoreactive cell in a random or site-specific manner. For example, the transgene can be inserted into the genome of an immune cell at a random site. The transgene can be functional, for example, fully functional when inserted into any site of the genome. For example, a transgene can encode its own promoter or can be inserted at a position controlled by an endogenous promoter. Alternatively, the transgene can be inserted into a gene, such as at an intron or an exon, a promoter or a non-coding region of the gene. The transgene can be inserted to disrupt a gene, such as an endogenous immune checkpoint, by insertion.

In some embodiments, one or more copies of the transgene can be inserted into the genome at multiple random sites. For example, multiple copies can be inserted into the genome at random sites. This may result in an increase in overall expression as compared with one random insertion of the transgene. Alternatively, a copy of the transgene can be inserted into a gene and another copy of the transgene can be inserted into a different gene. The transgene can be targeted so that it can be inserted into the genome of the immunoreactive cell at a specific site.

In some embodiments, a polynucleic acid comprising a sequence encoding an antigen binding receptor can be in a form of a plasmid vector. The plasmid vector may comprise a promoter. In certain cases, the promoter can be constitutive. In some embodiments, the promoter is inducible. The promoter may be or may be derived from CMV, U6, MND or EF1a. In some embodiments, the promoter can be adjacent to the CAR sequence. In some embodiments, the plasmid vector further comprises a splice acceptor. In some embodiments, the splice acceptor can be adjacent to the CAR sequence. The promoter sequence can be a PKG or MND promoter. The MND promoter may be a synthetic promoter containing the U3 region of the MoMuLV LTR modified with myeloproliferative sarcoma virus enhancer.

In some embodiments, a polynucleic acid encoding a receptor of interest can be designed to be delivered to a cell by non-viral techniques. In certain cases, the polynucleic acid can be a Good Manufacturing Practice (GMP) compatible reagent.

The expression of a polynucleic acid encoding an antigen binding receptor of interest or a CAR can be controlled by one or more promoters. The promoters can be ubiquitous, constitutive (unrestricted promoters, allowing for continuous transcription of relevant genes), tissue-specific promoters or inducible promoters. The expression of a transgene inserted adjacent to or proximate to a promoter can be regulated. For example, a transgene can be inserted near or beside a ubiquitous promoter. Some ubiquitous promoters may be CAGGS promoter, hCMV promoter, PGK promoter, SV40 promoter or ROSA26 promoter.

Promoters can be endogenous or exogenous. For example, one or more of the transgenes can be inserted adjacent to or proximate to the endogenous or exogenous ROSA26 promoter. Furthermore, the promoter may be specific for immunoreactive cells. For example, one or more of the transgenes can be inserted adjacent to or proximate to the porcine ROSA26 promoter.

Tissue-specific promoters or cell-specific promoters can be used to control the location of expression. For example, one or more of the transgenes can be inserted adjacent to or proximate to a tissue-specific promoter. Tissue-specific promoters may be FABP promoter, Lck promoter, CamKII promoter, CD19 promoter, keratin promoter, albumin promoter, aP2 promoter, insulin promoter, MCK promoter, MyHC promoter, WAP Promoter, or Col2A promoter.

Inducible promoters can also be used. These inducible promoters can be turned on and off by adding or removing an inducer if necessary. The inducible promoter is expected to be, but not limited to, Lac, tac, trc, trp, araBAD, phoA, recA, proU, cst-1, tetA, cadA, nar, PL, cspA, T7, VHB, Mx, and/or Trex.

The term "inducible promoter" as used herein is a controlled promoter which does not drive expression or drives low expression of a gene operably linked thereto before the desired condition is reached, and drives expression or high expression of the gene operably linked thereto under the desired condition.

Furthermore, although not essential for expression, the transgenic sequences may also comprise transcriptional or translational regulatory sequences, such as promoters, enhancers, insulators, internal ribosome entry sites, and sequences encoding 2A peptides and/or polyadenylation signals.

In some embodiments, the transgene encodes an antigen binding receptor of interest or a CAR, wherein the transgene is inserted into a safe harbor so that the antigen binding receptor is expressed. In some embodiments, the transgene is inserted into the PD1 and/or CTLA-4 locus. In other cases, the transgene is delivered with a lentivirus to a cell for random insertion, while a PD1- or CTLA-4 specific nuclease can be provided as an mRNA. In some embodiments, the transgene is delivered by a viral vector system such as retrovirus, AAV or adenovirus, and an mRNA encoding a nuclease (e.g. AAVS1, CCR5, albumin, or HPRT) specific for a safe harbor. Cells can also be treated with an mRNA encoding a PD1 and/or CTLA-4 specific nuclease. In some embodiments, the polynucleotide encoding the CAR is provided together with an mRNA encoding a HPRT-specific nuclease and a PD1- or CTLA-4 specific nuclease by a viral delivery system. CARs that can be used with the methods and compositions disclosed herein can comprise all types of these chimeric proteins.

In some embodiments, a transgene can be introduced into an immunoreactive cell using a retroviral vector (γ-retroviral or lentiviral vector). For example, a transgene encoding a CAR or any antigen binding receptor, or a variant or fragment thereof can be cloned into a retroviral vector, and can be driven by an endogenous promoter, a retroviral long terminal repeat, or a target cell type-specific promoter. Non-viral vectors can also be used. Non-viral vector delivery systems can comprise DNA plasmids, naked nucleic acids, and nucleic acids complexed with delivery vectors such as liposomes or Poloxamers.

Many virus-based systems have been developed for the transfer of genes into mammalian cells. For example, retroviruses provide a convenient platform for gene delivery systems. The selected gene can be inserted into a vector and packaged in a retroviral particle using techniques known in the art. Vectors derived from retroviruses such as lentiviruses are suitable tools for achieving long-term gene transfer because they allow long-term stable integration of the transgene and its propagation in daughter cells. Lentiviral vectors have an additional advantage over vectors derived from retroviruses such as murine leukemia virus, in that they can transduce non-proliferating cells. They also have an additional advantage of low immunogenicity. An advantage of adenoviral vectors is that they are not fused into the genome of the target cell, thereby bypassing negative integration-related events.

The cells can be transfected with a transgene encoding the antigen binding receptor. The concentration of the transgene can range from about 100 picograms to about 50 micrograms. In some embodiments, the amount of a nucleic acid (eg, ssDNA, dsDNA, or RNA) introduced into a cell can be altered to optimize transfection efficiency and/or cell viability. For example, 1 microgram of dsDNA can be added to each cell sample for electroporation. In some embodiments, the amount of the nucleic acid (e.g. double stranded DNA) required for optimal transfection efficiency and/or cell viability varies depending on the cell type. In some embodiments, the amount of the nucleic acid (e.g. dsDNA) used for each sample can directly correspond to the transfection efficiency and/or cell viability. For example, a range of transfection concentrations are used. The transgene encoded by the vector can be integrated into the genome of the cell. In some embodiments, the transgene encoded by the vector is forward integrated. In other cases, the transgene encoded by the vector is reverse integrated.

Generally, the vector is delivered in vivo by administration to an individual patient via systemic administration (e.g. intravenous, intraperitoneal, intramuscular, subcutaneous, or intracranial infusion) or topical application, as described below. Alternatively, a vector can be delivered ex vivo to a cell, such as a cell removed from an individual patient (e.g. lymphocytes, T cells, bone marrow aspirates, tissue biopsies), and then typically re-implanted into a patient after selecting the cell into which the vector has been incorporated. The cells can be expanded before or after selection.

Suitable immunoreactive cells for expression of an antigen binding receptor may be cells that are autologous or non-autologous to an individual in need thereof.

A suitable source of immune response cells can be obtained from an individual. In certain cases, T cells can be obtained. The T cells can be obtained from a number of sources, including PBMCs, bone marrow, lymph node tissue, cord blood, thymus tissue, and tissues from infected sites, ascites, pleural effusion, spleen tissue, and tumor tissue. In certain cases, T cells can be obtained from blood collected from an individual using any number of techniques known to those skilled in the art, such as Ficoll™ separation. In some embodiments, cells from circulating blood of an individual are obtained by apheresis. Apheresis products typically contain lymphocytes, including T cells, monocytes, granulocytes, B cells, other nucleated white blood cells, red blood cells, and platelets. In some embodiments, cells collected by apheresis collection can be washed to remove plasma fractions and placed in a suitable buffer or medium for subsequent processing steps.

Alternatively, cells can be derived from a healthy donor, from a patient diagnosed with cancer, or a patient diagnosed with an infection. In some embodiments, the cells can be a part of a mixed cell population with different phenotypic characteristics. Cell lines can also be obtained from transformed T cells according to the methods previously described. Cells can also be obtained from a cell therapy library. Modified cells that are resistant to immunosuppressive therapy can be obtained by any of the methods described herein. It is also possible to select a suitable cell population prior to modification. The engineered cell population can also be selected after modification. Engineered cells can be used for autologous transplantation. Alternatively, the cells can be used for allogeneic transplantation. In some embodiments, the cells are administered to the same patient whose sample is used for identification of a cancer associated target sequence. In other instances, the cells are administered to a patient different from the patient whose sample is used for identification of the cancer associated target sequence.

In some embodiments, suitable primary cells comprise peripheral blood mononuclear cells (PBMCs), peripheral blood lymphocytes (PBLs), and other blood cell subpopulations such as, but not limited to, T cells, natural killer cells, monocytes, natural killer T cells, monocyte precursor cells, hematopoietic stem cells or non-pluripotent stem cells. In some embodiments, the cell can be any immune cell, including any T cell such as a tumor infiltrating cell (TIL), such as a CD3+ T cell, a CD4+ T cell, a CD8+ T cell, or any other type of T cell. T cells can also comprise memory T cells, memory stem T cells, or effector T cells. It is also possible to select T cells from a large population, for example to select T cells from whole blood. T cells can also be expanded from a large population. T cells may also preferentially be those of specific populations and phenotypes. For example, T cells may preferentially have a phenotype comprising CD45RO(−), CCR7(+), CD45RA(+), CD62L(+), CD27(+), CD28(+), and/or IL-7Rα(+). Suitable cells may have one or more markers selected from the list of CD45RO(−), CCR7 (+), CD45RA(+), CD62L(+), CD27(+), CD28(+) and/or IL-7Rα(+). Suitable cells also comprise stem cells such as embryonic stem cells, induced pluripotent stem cells, hematopoietic stem cells, neuronal stem cells, and mesenchymal stem cells. Suitable cells can comprise any number of primary cells, such as human cells, non-human cells, and/or mouse cells. Suitable cells can be progenitor cells. Suitable cells can be derived from a subject to be treated (e.g., a patient).

The therapeutically effective amount of the cells that is required in a patient can vary depending on the viability of the cells and the efficiency with which the cells are genetically modified (e.g. the efficiency with which the transgene is integrated into one or more cells or the expression level of the protein encoded by the transgene). In some embodiments, the result (e.g. multiplication) of the cell viability after genetic modification and the integration efficiency of the transgene can correspond to a therapeutic amount of cells available for administration to a subject. In some embodiments, an increase in cell viability after genetic modification may correspond to a reduction in the essential amount of administered cells effective to treat a patient. In some embodiments, an increase in the efficiency of integration of the transgene into one or more cells can correspond to a reduction in the essential amount of administered cells effective to treat a patient. In some embodiments, determining the therapeutically effective amount of the cells that is required can comprise determining a function associated with a change in the cells over time. In some embodiments, determining the therapeutically effective amount of cells that is required can comprise determining a function corresponding to a change in efficiency of integrating the transgene into one or more cells according to a time-dependent variable (e.g. cell culture time, electroporation time, cell stimulation time). In some embodiments, the therapeutically effective cell can be a population of cells comprising expression of about 30% to about 100% of antigen binding receptors on the cell surface. In some embodiments, the therapeutically effective cells can express about 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9% or more than about 99.9% of antigen binding receptors on the cell surface, as measured by flow cytometry According to one aspect of the invention, the invention also encompasses a nucleic acid encoding the antigen binding receptor. The invention also relates to a variant of the above-mentioned polynucleotide, which encodes a polypeptide having the same amino acid sequence as the invention, or a fragment, an analog and a derivative of the polypeptide.

The invention further provides a vector comprising the above-mentioned nucleic acid encoding the antigen binding receptor protein that is expressed on the surface of an immune response cell.

The invention further encompasses a virus comprising the above-mentioned vector. The virus of the invention comprises a packaged infectious virus, and also comprises a virus to be packaged containing components necessary for packaging as an infectious virus. Other viruses known in the art that can be used to transduce an exogenous gene into an immune response cell and their corresponding plasmid vectors can also be used in the invention.

In another aspect, provided herein is a host cell, comprising an antibody or chimeric antigen receptor as described herein, and optionally Type I interferon. In another aspect, provided herein is a host cell, comprising nucleic acids encoding an antibody or chimeric antigen receptor described herein, and optionally type I interferon.

In some embodiments, the host cell is an immune response cell. In some embodiments, the immune response cell is a T cell, a natural killer cell, a cytotoxic T lymphocyte, a natural killer T cell, a DNT cell, and/or a regulatory T cell. In some embodiments, the host cell is an NK92 cell.

The immune response cell of the invention may further carry a coding sequence of an exogenous cytokine; and the cytokine includes but not limited to: IL-12, IL-15 or IL-21, etc. These cytokines have the further immunomodulatory or anti-tumor activity, and can enhance the function of effector T cells and activated NK cells, or directly exert the anti-tumor effect. Thus, those skilled in the art will appreciate that the use of these cytokines will help the immune response cell function better.

The immune response cell of the invention may also express an antigen binding receptor other than the antigen binding receptor described above.

The immune response cell of the invention may also express a chemokine receptor; and the chemokine receptor includes, but is not limited to, CCR2. Those skilled in the art will appreciate that the CCR2 chemokine receptor may allow the CCR2 in vivo to bind to the chemokine competitively, which is advantageous for blocking tumor metastasis.

The immune response cell of the invention can also express an siRNA that reduces PD-1 expression or a protein that blocks PD-L1. Those skilled in the art will appreciate that competitively blocking the interaction of PD-L1 with its receptor PD-1 facilitates the recovery of anti-tumor T cell responses, thereby inhibiting tumor growth.

The immune response cell of the invention may also express a safety switch; preferably, the safety switch comprises: iCaspase-9, Truncated EGFR or RQR8.

In some embodiments, the immune response cell of the invention does not express a costimulatory ligand such as 4-1BBL.

Accordingly, in another aspect, provided herein is a method for generating an antibody or chimeric antigen receptor described herein or a composition comprising the same, comprising culturing a host cell described herein under suitable conditions. In some embodiments, the method comprises isolating and obtaining an expression product of the host cell.

In another aspect, provided herein is a composition, comprising an antibody, chimeric antigen receptor, or nucleic acid described herein. In some embodiments, the composition is a pharmaceutical composition comprising the antibody, chimeric antigen receptor or nucleic acid. In some embodiments, the pharmaceutical composition further comprises a pharmaceutically acceptable carrier.

In another aspect, provided herein is a pharmaceutical composition, comprising a host cell described herein and a pharmaceutically acceptable carrier.

The term "pharmaceutically acceptable" means that when a molecule itself and a composition are appropriately administered to an animal or a human, they do not produce an adverse, allergic or other adverse reaction.

In some embodiments, the composition comprises an additional therapeutic agent. In some embodiments, the additional therapeutic agent is a chemotherapeutic agent, such as those described in US 20140271820 and/or pharmaceutically acceptable salts or analogs thereof. In some embodiments, the therapeutic agent includes, but is not limited to, a mitotic inhibitor (vinca alkaloid), including vincristine, vinblastine, vindesine, and Navelbine™ (vinorelbine, 5'-dehydrohydrogen sulfide); a topoisomerase I inhibitor, such as camptothecin compounds, including Camptosar™ (irinotecan HCL), Hycamtin™ (topotecan HCL), and other compounds derived from camptothecin and analogs thereof; a podophyllotoxin derivative such as etoposide, teniposide and midoxizoz; an alkylating agent such as cisplatin, cyclophosphamide, nitrogen mustard, trimethylene thiophosphoramide, carmustine, busulfan, chlorambucil, briquinolizine, uracil mustard, cloprofen and dacarbazine; an antimetabolite, including cytarabine, 5-fluorouracil, methotrexate, mercaptopurine, azathioprine and procarbazine; an antibiotic, including but not limited to doxorubicin, bleomycin, dactinomycin, daunorubicin, mycinmycin, mitomycin, sarkomycin C and daunomycin; and other chemotherapeutic drugs, including but not limited to anti-tumor antibodies, dacarbazine, azacytidine, amsacon, melphalan, ifosfamide and mitoxantrone. In some embodiments, the additional therapeutic agent is selected from one or more of epirubicin, oxaliplatin, and 5-fluorouracil. In some embodiments, the additional therapeutic agent includes, but is not limited to, an anti-angiogenic agent, including anti-VEGF antibodies (including humanized and chimeric antibodies, anti-VEGF aptamers and antisense oligonucleotides), and other inhibitors of angiogenesis such as angiostatin, endostatin, interferon, interleukin 1 (including α and β), interleukin 12, retinoic acid, tissue inhibitors of metalloproteinases-1 and -2, and the like.

Specific examples of some substances which can be used as pharmaceutically acceptable carriers or components thereof are sugars such as lactose, glucose and sucrose; starches such as corn starch and potato starch; cellulose and derivatives thereof such as sodium carboxymethylcellulose, ethyl cellulose and methyl cellulose; tragacanth powder; malt; gelatin; talc; solid lubricants, such as stearic acid and magnesium stearate; calcium sulfate; vegetable oils, such as peanut oil, cottonseed oil, sesame oil, olive oil, corn oil and cocoa butter; polyols such as propylene glycol, glycerin, sorbitol, mannitol and polyethylene glycol; alginic acid; emulsifiers such as Tween; wetting agents such as sodium lauryl sulfate; coloring agents; flavoring agents; tableting agents, stabilizers; antioxidants; preservatives; pyrogen-free water; isotonic saline solutions; phosphate buffers and the like.

The pharmaceutical composition described herein may comprise one or more pharmaceutically acceptable salts. The "pharmaceutically acceptable salt" refers to a salt that retains the desired biological activity of a parent compound and does not produce any adverse toxicological effect (see, for example, Berge, S. M et al. 1977, J. Pharm. Sci. 66: 1-19). Examples of such salt comprise acid addition salts and base addition salts.

Acid addition salts comprise salts derived from non-toxic inorganic acids such as hydrochloric acid, nitric acid, phosphoric acid, sulfuric acid, hydrobromic acid, hydroiodic acid and phosphorous acid, etc.; and salts derived from non-toxic organic acids such as an aliphatic monocarboxylic acid and dicarboxylic acid, a phenyl-substituted alkanoic acid, a hydroxyalkanoic acid, an aromatic acid, and an aliphatic or aromatic sulfonic acid, etc. Base addition salts comprise salts derived from alkaline earth metals (such as sodium, potassium, magnesium and calcium), and salts derived from non-toxic organic amines such as N,N'-dibenzylethylenediamine, N-methylglucosamine, chloroprocaine, choline, diethanolamine, ethylenediamine and procaine, etc.

The pharmaceutical composition described herein may also comprise an antioxidant. Examples of the antioxidant include, but are not limited to: water soluble antioxidants such as ascorbic acid, cysteine hydrochloride, sodium hydrogen sulfate, sodium metabisulfite and sodium sulfite, etc.; oil soluble antioxidants such as ascorbyl palmitate, butylated hydroxyanisole (BHA), butylated hydroxytoluene (BHT), lecithin, propyl gallate, and α-tocopherol, etc.; and metal chelating agents such as citric acid, ethylenediaminetetraacetic acid (EDTA), sorbitol, tartaric acid, and phosphoric acid, etc.

The composition of the invention can be formulated into various dosage forms as needed, and can be administered after determining a dose beneficial for a patient by a physician in accordance with factors such as the patient type, age, body weight, and general disease condition, and mode of administration, etc. The mode of administration can be, for example, parenteral administration (e.g. injection) or other treatment manners.

"Parenteral" administration of an immunogenic composition comprises, for example, subcutaneous (s.c.), intravenous (i.v.), intramuscular (i.m.) or intrasternal injection or infusion techniques.

A formulation comprising an immunoreactive cell population administered to an individual comprise a plurality of immunoreactive cells effective to treat and/or prevent a particular indication or disease. Thus, a therapeutically effective population of immunoreactive cells can be administered to an individual. Typically, a formulation comprising from about $1\times10^4$ to about $1\times10^{10}$ immunoreactive cells is administered. In most cases, the formulation will comprise from about $1\times10^5$ to about $1\times10^9$ immunoreactive cells, from about $5\times10^5$ to about $5\times10^8$ immunoreactive cells, or from about $1\times10^6$ to about $1\times10^7$ immunoreactive cells. However, depending on the location, source, identity, extent and severity of the cancer, the age and physical condition of the individual to be treated, and the like, the number of CAR immunoreactive cells administered to the individual will vary within a wide range. The doctor will finally decide an appropriate dose to be used.

In some embodiments, a chimeric antigen receptor is used to stimulate an immune cell mediated immune response. For example, a T cell mediated immune response is an immune response involving T cell activation. Activated antigen-specific cytotoxic T cells are capable of inducing apoptosis in target cells that display exogenous antigenic epitopes on the surface, such as cancer cells that display tumor antigens. In some other embodiments, a chimeric antigen receptor is used to provide anti-tumor immunity in a mammal. A subject will develop anti-tumor immunity due to T cell-mediated immune responses.

In certain cases, a method of treating a subject with cancer can involve administering one or more immune response cells of the invention to the subject in need of treatment. The immune response cells can bind to tumor target molecules and induce cancer cell death. As described above, the invention further provides a method for treating a pathogen infection in an individual comprising administering to the individual a therapeutically effective amount of an immune response cell of the invention.

The frequency of administration of the immunoreactive cells of the invention will depend on factors including the disease being treated, the elements of the particular immunoreactive cells, and the mode of administration. For example, the immunoreactive cells can be dosed 4 times, 3 times, 2 times a day, once a day, every other day, every three days, every four days, every five days, every six days, once a week, once every eight days, once every nine days, once every ten days, once a week, or twice a month. As described herein, since the immune response cells of the present application have improved viability, they can be administered not only in a lower therapeutically effective amount, but also at a lower frequency, to obtain at least similar and preferably more pronounced efficacy, as compared with an immune response cell that is similar but does not express exogenous type I interferon.

In some embodiments, the compositions may be isotonic, i.e. they may have the same osmotic pressure as the blood and tears. The desired isotonicity of the composition of the invention can be achieved using sodium chloride, or other pharmaceutically acceptable agents such as glucose, boric acid, sodium tartrate, propylene glycol or other inorganic or organic solutes. If desired, the viscosity of the composition can be maintained at a selected level using a pharmaceutically acceptable thickener. Suitable thickeners comprise, for example, methyl cellulose, xanthan gum, carboxymethylcellulose, hydroxypropylcellulose, carbomer, and the like. The preferred concentration of a thickener will depend on the reagent selected. It will be apparent that the choice of a suitable carrier and other additives will depend on the exact route of administration and the nature of the particular dosage form, such as a liquid dosage form.

The invention further provides a kit comprising the antibody, chimeric antigen receptor, and nucleic acid or immune response cell described herein. In some embodiments, the kit can comprise a therapeutic or prophylactic composition comprising an effective amount of an antibody, chimeric antigen receptor, nucleic acid, or immune response cell described herein in one or more unit dosage forms. In some embodiments, the kit comprises a sterile container that can contain the therapeutic or prophylactic composition; such a container can be a cartridge, ampule, bottle, vial, tube, bag or blister pack, or other suitable container forms known in the art. Such containers may be made of plastic, glass, laminated paper, metal foil or other materials suitable for holding the drug. In some embodiments, the kit comprises the antibody, chimeric antigen receptor, nucleic acid or immune response cell described herein, and instructions indicating administration of the antibody, chimeric antigen receptor, nucleic acid or immune response cell described herein to an individual. The instructions usually comprise the use of the antibody, chimeric antigen receptor, nucleic acid or immune response cell described herein for treating or preventing cancer or tumors. In some embodiments, the kit comprises the host cell described herein and can comprise from about $1\times10^4$ cells to about $1\times10^6$ cells. In some embodiments, the kit can comprise at least about $1\times10^5$ cells, at least about $1\times10^6$ cells, at least about $1\times10^7$ cells, at least about $4\times10^7$ cells, at least about $5\times10^7$ cells, at least about $6\times10^7$ cells, at least about $6\times10^7$ cells, $8\times10^7$ cells, at least about $9\times10^7$ cells, at least about $1\times10^8$ cells, at least about $2\times10^8$ cells, at least about $3\times10^8$ cells, at least about $4\times10^8$ cells, at least about $5\times10^8$ cells, at least about $6\times10^8$ cells, at least about $6\times10^8$ cells, at least about $8\times10^8$ cells, at least about $9\times10^8$ cells, at least about $1\times10^9$ cells, at least about $2\times10^9$ cells, at least about $3\times10^9$ cells, at least about $4\times10^9$ cells, at least about $5\times10^9$ cells, at least about $6\times10^9$ cells, at least about $8\times10^9$ cells, at least about $9\times10^9$ cells, at least about $1\times10^{10}$ cells, at least about $2\times10^{10}$ cells, at least about $3\times10^{10}$ cells, at least about $4\times10^{10}$ cells, at least about $5\times10^{10}$ cells, at least about $6\times10^{10}$ cells, at least about $7\times10^{10}$ cells, at least about $8\times10^{10}$ cells, at least about $9\times10^{10}$ cells, at least about $1\times10^{11}$ cells, at least about $2\times10^{11}$ cells, at least about $3\times10^{11}$ cells, at least about $4\times10^{11}$ cells, at least about $5\times10^{11}$ cells, at least about $8\times10^{11}$ cells, at least about $9\times10^{11}$ cells, or at least about $1\times10^{12}$ cells. For example, approximately $5\times10^{10}$ cells can be comprised in the kit. In another example, the kit can comprise $3\times10^6$ cells; and the cells can be expanded to about $5\times10^{10}$ cells and administered to a subject.

In some embodiments, the kit can comprise allogeneic cells. In some embodiments, the kit can comprise cells that can contain genomic modifications. In some embodiments, the kit can comprise "ready-to-use" cells. In some embodiments, the kit can comprise cells that can be expanded for clinical use. In certain cases, the kit may comprise a content for research purposes.

In some embodiments, the instructions comprise at least one of: a description of a therapeutic agent; a dosage regimen and administration for treating or preventing a tumor or a symptom thereof; preventive measures, warnings, contraindications, excessive information, adverse reactions, animal pharmacology, clinical studies, and/or citations. The instructions can be printed directly on the container (if any), or as a label on the container, or as a separate paper, booklet, card or folder within the container or in the container. In some embodiments, the instructions provide a method for administering the immune response cell of the invention for treating or preventing a tumor. In certain cases, the instructions provide a method for administering the immunoreactive cell of the invention before, after or simultaneously with the administration of a chemotherapeutic agent.

In another aspect, provided herein is a method for inducing death of a cell comprising IL-13RA2, comprising contacting the cell with the antibody described herein, the chimeric antigen receptor described herein, the composition described herein, or the host cell described herein. In some embodiments, the contacting is contacting in vitro. In some embodiments, the contacting is contacting in vivo.

In some embodiments, the cell is a tumor cell. In some embodiments, the cell is a brain tumor, and more specifically, may be astrocytoma, meningioma, and glioma.

In another aspect, provided herein is a method for treating a tumor in an individual in need thereof, comprising administering to the individual an effective amount of the antibody, chimeric antigen receptor, composition, vector or host cell described herein.

In some embodiments, the immunoreactive cell can be administered to a subject, wherein the immunoreactive cell that can be administered can be from about 1 to about 35 days of age. For example, the cells administered may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 days or up to about 40 days of age. The age of the CAR immunoreactive cell can be calculated from the time of stimulation. The age of the immunoreactive cell can be calculated from the time of blood collection. The age of the immunoreactive cell can be calculated from the time of transduction. In some embodiments, the immunoreactive cells that can be administered to the subject are from about 10 to about 14 or about 20 days of age. In some embodiments, the "age" of an immunoreactive cell can be determined by the telomere length. For example, a "young" immune response cell can have a longer telomere length than a "depleted" or "old" immunoreactive cell. Without being bound by a particular theory, it is believed that the immunoreactive cell loses an estimated telomere length of about 0.8 kb per week in culture, and the young immunoreactive cell culture can have a telomere that is about 1.4 kb longer than the immunoreactive cell of about 44 days of age. Without being bound by a particular theory, it is believed that a longer telomere length can be associated with a positive objective clinical response in a patient and the persistence of cells in vivo.

Cells (e.g. engineered cells or engineered primary T cells) can be functional before, after, and/or during transplantation. For example, the transplanted cells can function at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90 or 100 days after transplantation. The transplanted cells can function at least about 1, 2, 3, 4, 5, 6, 7, 8, 9, 10, 11 or 12 months after transplantation. The transplanted cells can function at least about 1, 2, 3, 4, 5, 6, 7, 8, 9, 10, 15, 20, 25 or 30 years after transplantation. In some embodiments, the transplanted cells can function during the life of a recipient.

In addition, the transplanted cells can function at 100% of their normal expected function. The transplanted cells can also perform about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or up to about 100% of their normal expected function.

The transplanted cells can also perform more than 100% of their normal intended function. For example, the transplanted cells can perform approximately 110%, 120%, 130%, 140%, 150%, 160%, 170%, 180%, 190%, 200%, 250%, 300%, 400%, 500%, 600%, 700%, 800%, 900%, 1000% or up to about 5,000% of the normal expected function.

The transplantation can be done by any type of transplantation. Local transplantation may include, but is not limited to, subhepatic sac space, subsplenic sac space, subrenal sac space, omentum, gastric or intestinal submucosa, small intestinal vascular segment, venous sac, testis, brain, spleen, or cornea. For example, the transplantation can be subcapsular transplantation. The transplantation can also be intramuscular transplantation. The transplantation can be portal vein transplantation.

The transplant rejection can be improved after treatment with the immune response cell of the invention as compared with the cases that one or more wild type cells are transplanted to the recipient. For example, the transplant rejection can be a hyperacute rejection. The transplant rejection can also be an acute rejection. Other types of rejection may comprise chronic rejection. The transplant rejection can also be cell-mediated rejection or T cell-mediated rejection. The transplant rejection can also be natural killer cell-mediated rejection.

Improving transplantation may mean alleviating hyperacute rejection, which may comprise reducing, alleviating or reducing adverse effects or symptoms. The transplantation can refer to adoptive transplantation of cellular products.

Another indication of successful transplantation may be the number of days the recipient does not need immunosuppressive therapy. For example, after providing the immune response cell of the invention, the recipient may not require the immunosuppressive therapy for at least about 1, 2, 3, 4, 5, 6, 7, 8, 9, 10 or more days. This can indicate that the transplantation is successful. This can also indicate that the transplanted cells, tissues and/or organs are not rejected.

In some embodiments, the antibody, chimeric antigen receptor, composition, vector or host cell described herein can be administered in combination with another therapeutic agent. In some embodiments, the additional therapeutic agent is a chemotherapeutic agent, such as those described in US 20140271820. The chemotherapeutic drug which can be used in combination with the immune response cell of the invention includes, but is not limited to, a mitotic inhibitor (vinca alkaloid), including vincristine, vinblastine, vindesine, and Navelbine™ (vinorelbine, 5'-dehydrohydrogen sulfide); a topoisomerase I inhibitor, such as camptothecin compounds, including Camptosar™ (irinotecan HCL), Hycamtin™ (topotecan HCL), and other compounds derived from camptothecin and analogs thereof; a podophyllotoxin derivative such as etoposide, teniposide and midoxizoz; an alkylating agent such as cisplatin, cyclophosphamide, nitrogen mustard, trimethylene thiophosphoramide, carmustine, busulfan, chlorambucil, briquinolizine, uracil mustard, cloprofen and dacarbazine; an antimetabolite, including cytarabine, 5-fluorouracil, methotrexate, mercaptopurine, azathioprine and procarbazine; an antibiotic, including but not limited to doxorubicin, bleomycin, dactinomycin, daunorubicin, mycinmycin, mitomycin, sarkomycin C and daunomycin; and other chemotherapeutic drugs, including but not limited to anti-tumor antibodies, dacarbazine, azacytidine, amsacon, melphalan, ifosfamide and mitoxantrone. In some embodiments, the additional therapeutic agent is selected from one or more of epirubicin, oxaliplatin, and 5-fluorouracil.

In some embodiments, the chemotherapeutic drug that can be used in combination with the immune response cell of the invention includes, but is not limited to, an anti-angiogenic agent, including anti-VEGF antibodies (including humanized and chimeric antibodies, anti-VEGF aptamers and antisense oligonucleotides), and other inhibitors of angiogenesis such as angiostatin, endostatin, interferon, interleukin 1 (including α and β), interleukin 12, retinoic acid, and tissue inhibitors of metalloproteinases-1 and -2.

The invention further relates to a vector comprising the above-mentioned appropriate DNA sequence, as well as an appropriate promoter or a control sequence. The vector can be used to transform an appropriate host cell to enable it to express a protein. The host cell can be a prokaryotic cell, such as a bacterial cell; or a lower eukaryotic cell, such as a yeast cell; or a higher eukaryotic cell, such as a mammalian cell.

The invention is further illustrated in connection with particular examples as follows. It should be understood that these examples are merely illustrative of the invention and are not intended to limit the scope of the invention. The experimental methods in the following examples which do not specify the specific conditions are usually performed according to conventional conditions such as described by J. Sambrook et al. in Molecular Cloning: a Laboratory Manual, 3rd Edition, Science Press, 2002, or according to the the conditions recommended by the manufacturer.

Example 1. Preparation of Recombinant IL-13RA2 and IL-13RA1 Proteins a. Construction of IL-13RA2 huFc, and IL-13RA1_huFc Expression Plasmids The gene (SEQ ID NO: 17) of the extracellular segment Asp27-Arg343 (SEQ ID NO: 18) of human IL-13RA2 was synthesized in vitro; and the gene was inserted into an eukaryotic expression plasmid containing the Fc segment Asp104-Lys330 of the human IgG1 heavy chain constant region, connected via "GS" therebetween to form a fusion expression protein IL-13RA2 huFc (SEQ ID NO: 22), and the corresponding gene sequence of the fusion expression protein is shown as in SEQ ID NO: 11. Alternatively, the gene (SEQ ID NO: 19) of the IL-13RA1 extracellular segment was inserted into an eukaryotic expression plasmid containing the Fc segment Asp104-Lys330 of the human IgG1 heavy chain constant region, connected via "GS" therebetween to form a fusion expression protein IL-13RA1_huFc (SEQ ID NO: 24), and the corresponding gene sequence of the fusion expression protein is shown as in SEQ ID NO: 23.

b. Expression of IL-13RA2 huFc and IL-13RA1_huFc Through Transient Transfection

1) One day before transfection, $6-7 \times 10^5$/ml 293F cells were inoculated into a 125 ml culture flask.

2) On the day of transfection, $3 \times 10^7$ cells were adjusted in a 28 ml FreeStyle™ 293 expression medium.

3) The lipid-DNA complex was prepared by following the operation steps:

30 ug DNAs were diluted with Opti-MEM I to a final volume of 1 ml, and mixed thoroughly.

60 ul 293Fectin™ was diluted with Opti-MEM I to a final volume of 1 ml, and mixed thoroughly.

The mixture was incubated for 5 minutes at room temperature.

4) The diluted DNAs were mixed with 293Fectin™, and incubated for 20 minutes at room temperature.

5) 2 ml DNA-293fectin complex was added to 28 ml cells, cultured at 37° C., in 8% CO2, at 125 rpm for 3-4 days, and the supernatant was collected.

c. Purification of IL-13RA2 huFc and IL-13RA1_huFc

1) The supernatant was cultured under centrifugation at 13000 rpm for 15 min.

2) Affinity purification was carried out using protein A filler, and the specific operation steps were as follows:

Equilibration: the protein filler was equilibrated with 10 column volumes of an equilibration buffer.

Loading: all samples processed with 0.45 μm filter membrane were loaded.

Washing: impurities were washed with 20 column volumes of the equilibration buffer until breakthrough without outflow.

Elution: the protein of interest was eluted with 10 column volumes of an elution buffer (6% neutralization buffer was added to the collection tube beforehand).

Solution Formula

Equilibration buffer: PBS at pH 7.4

Elution buffer: 0.1 M glycine at pH 2.6

Neutralization buffer: 1 M Tris

3) The eluate was filtered through a 0.22 um membrane, concentrated using a millipore ultrafiltration tube with a cut-off amount of 10 KD to not more than a volume of 1 ml, desalted using a PD-Midi desalting column, and 1.5 ml of a sample was collected. The protein concentration was measured by OD280/1.47.

2 μg was taken to run SDS-PAGE, and the results are shown as in FIG. 1.

Figure 2:
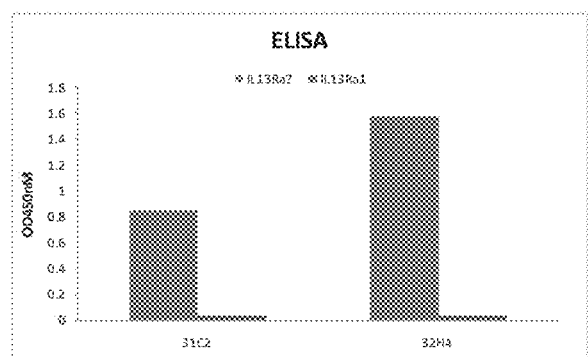
FIG. 2 shows detection of the binding of 31C2 and 32H4 to IL-13RA2 and IL13Ra1 by ELISA.

Example 2. Screening of scFv Specific for IL-13RA2 Using a Whole Human Phage Display Library The phage display library used in the invention is a whole human natural scFv phage library constructed by the company, and has a library capacity of 1E+11. An scFv fragment highly specific for IL-13RA2 was obtained using screening methods known to those skilled in the art. Briefly, 10 ug/ml of antigens IL-13RA2 huFc and IL-13RA1_huFc were coated in the immunotubes, respectively. To screen for antibodies that specifically bind to IL-13RA2, the phage library was added to the immunotube coated with IL-13RA1_huFc for binding for 1 hour. The supernatant was added to the immunotube coated with IL-13RA2 huFc for binding for 1.5 hours, then the non-specific phages were washed away, the bound phages were eluted and taken to infect *E. coli* TG1 at the logarithmic growth phase. The eluted phages were expansion cultured, and the expanded phage library was purified by using the PEG/NaCl precipitation method for the next round of screening. Panning was performed for 3-4 cycles to enrich for scFv phage clones that specifically bind to IL-13RA2. Positive clones were determined by standard ELISA methods for IL-13RA2 huFc. IL-13RA1_huFc was used in the ELISA as an unrelated antigen to verify the specificity of the antibody. A total of 3,420 clones were screened, of which 44 clones were detected by ELISA assay to specifically bind to IL-13RA2 huFc, and not bind to IL-13RA1_huFc. After sequencing, 5 single sequences were obtained. The 5 clones were expressed and purified, only 2 of them specifically bound U251 cells expressing IL13RA2 (purchased from the cell bank of Chinese Academy of Sciences) (FIGS. 2 and 4), and the names of the clones are 31C2 and 32H4.

The amino acid sequence of the heavy chain variable region of 31C2 is shown as in SEQ ID NO: 2, the amino acid sequence of the light chain variable region is shown as in SEQ ID NO: 4; the amino acid sequence of the heavy chain variable region of 32H4 is shown as in SEQ ID NO: 6, and the amino acid sequence of the light chain variable region is shown as in SEQ ID NO: 8. The amino acid sequence of HDCR1 of 31C2 is shown as in SEQ ID NO: 9, the amino acid sequence of HDCR2 is shown as in SEQ ID NO: 10, the amino acid sequence of HDCR3 is shown as in SEQ ID NO: 11, the amino acid sequence of LDCR1 is shown as in SEQ ID NO: 13, the amino acid sequence of LDCR2 is shown as in SEQ ID NO: 14, and the amino acid sequence of LDCR3 is shown as in SEQ ID NO: 15; the amino acid sequence of HDCR1 of 32H4 is shown as in SEQ ID NO: 9, the amino acid sequence of HDCR2 is shown as in SEQ ID NO: 10, the amino acid sequence of HDCR3 is shown as in SEQ ID NO: 12, the amino acid sequence of LDCR1 is shown as in SEQ ID NO: 13, the amino acid sequence of LDCR2 is shown as in SEQ ID NO: 14, and the amino acid sequence of LDCR3 is shown as in SEQ ID NO: 16.

Example 3. ELISA Binding Assay

Figure 3:
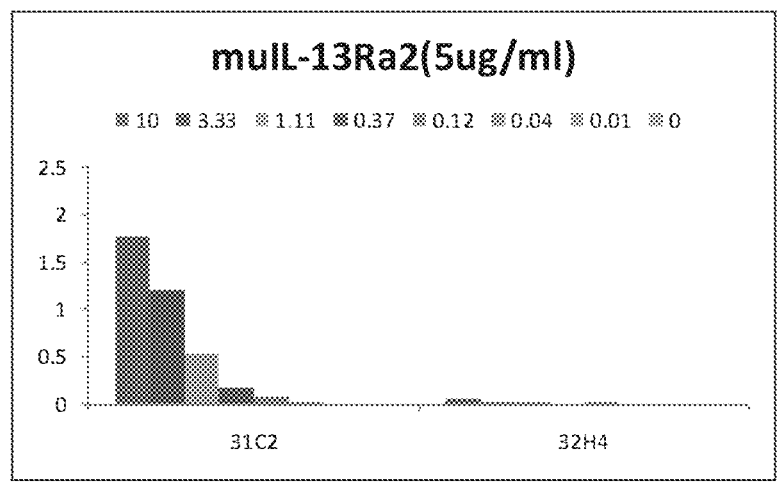
FIG. 3 shows detection of the binding of antibodies 31C2 and 32H4 to murine IL-13RA2 by ELISA.

The species specificity of antibodies 31C2 and 32H4 was determined by standard ELISA. Murine IL-13RA2 was purchased from Sino Biological Inc. The ELISA plate was coated with 100 ul of 5 ug/ml murine IL-13RA2 per well at 4° C. overnight. The coated ELISA plate was washed with PBS three times. 200 ul solution of 2% skim milk powder in PBS per well was added for blocking at room temperature for 1 hour. The plate was washed with PBS three times. The gradiently diluted antibodies with a starting concentration of 10 μg/ml, 3-fold serially diluted, were added and incubated at room temperature for 1 hr. The mixture was washed with PBST three times and washed with PBS three times. HRP-labeled goat anti-human Fc was added and incubated at room temperature for 1 hour. The mixture was washed with PBST three times and washed with PBS three times. After TMB was added for color development for 15 minutes, and the reaction was stopped by the addition of sulfuric acid, and read on a microplate reader. The result is shown in FIG. 3. Antibody 31C2 can bind to murine IL-13RA2, and antibody 32H4 does not bind to murine IL-13RA2.

Example 4. Construction of Anti-IL-13RA2 scFv_Fc Fusion Antibody, and its Transient Transfection, Expression, Purification and Activity Identification in an Eukaryotic Cell Primers were designed for the VH and VL fragments of 31C2 and 32H4, respectively, and a linker consisting of 15 flexible amino acids (GGGGSGGGGSGGGGS) [SEQ ID NO:76] was introduced to form a scFv; a suitable restriction site and a protective base were introduced upstream of the VH, and a suitable restriction site and a protective base were introduced downstream of the VL. The PCR product was analyzed by 1% agarose gel electrophoresis, purified and recovered. After enzymatic digestion, the product is ligated into a suitable eukaryotic expression vector. 293F cells at the logarithmic growth phase were transiently transfected with 293Fectin™ Transfection reagent (Invitrogen, 12347-019) or polyethyleneimine (PEI) (Sigma-Aldrich, 408727). The culture supernatant was collected 5-7 days after transfection, and subjected to affinity purification by Protein A.

Figure 4:
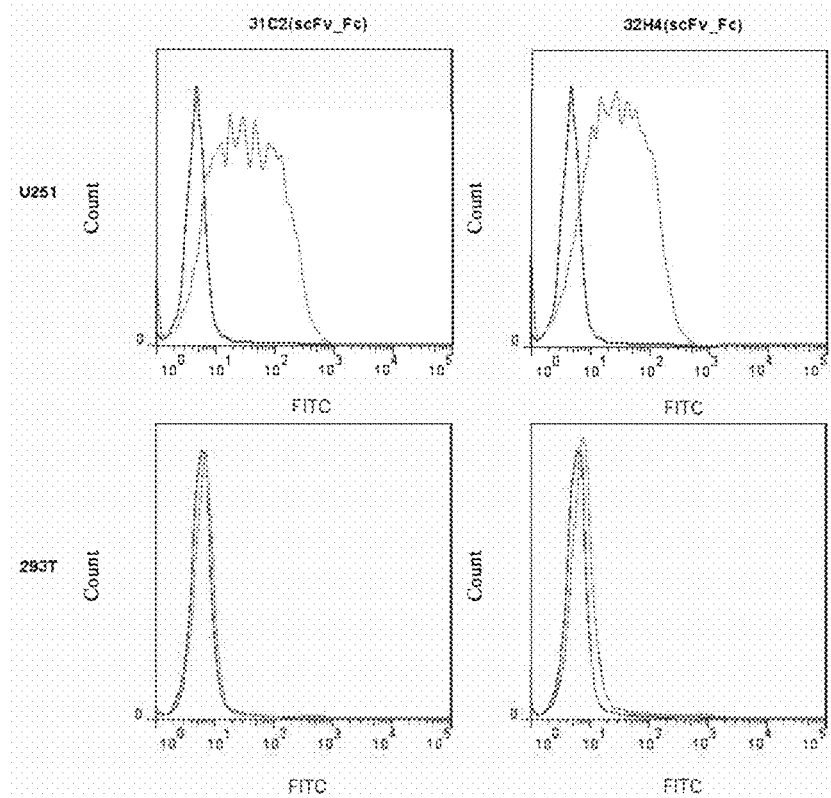
FIG. 4 shows detection of the binding of antibodies 31C2 and 32H4 to U251 (IL-13RA2-positive) and 293T (IL-13RA2-negative) cells by FACs.

The binding of the antibody to U251 cells endogenously expressing IL-13RA2 was tested by flow cytometry, with 293T cells as the negative cell control. The specific method of FACs assay was as follows: cells were harvested, washed once with a growth medium, and resuspended in PBS, and the cell concentration was adjusted to 4E+5 cells/ml. The diluted scFv_Fc fusion antibody was incubated with the cells for 30 minutes on ice, and the antibody concentration was 111 nM. Then the mixture was incubated with a FITC-labeled anti-human IgG secondary antibody. After two washing steps, detection was performed using a Guava easyCyte™ HT System instrument. FIG. 4 shows the binding state of scFv_Fc fusion forms of antibodies 31C2 and 32H4 to U251 and 293T cells. Both of the antibodies specifically bind to U251 cells endogenously expressing IL-13RA2, and do not bind to negative cell 293T.

Figure 5:
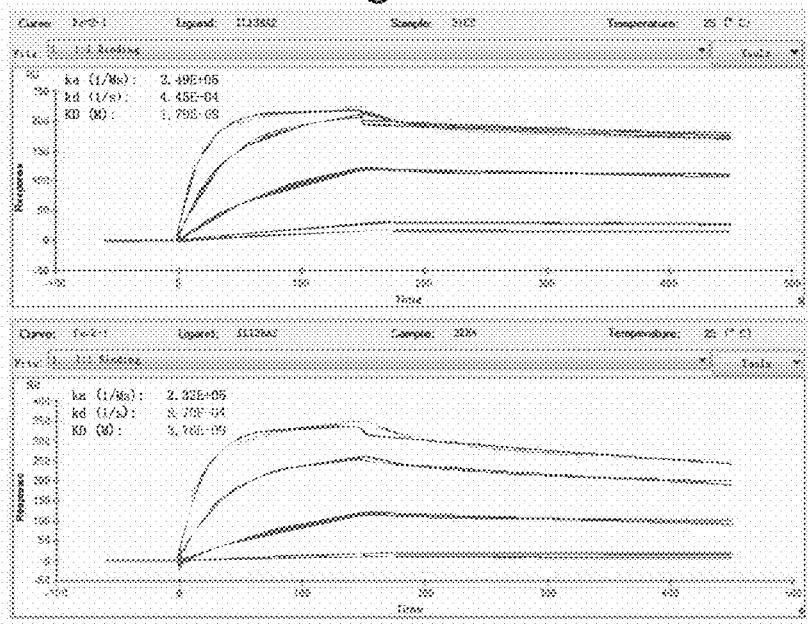
FIG. 5 shows detection of the affinity of antibodies 31C2 and 32H4 (scFv_Fc) by Biacore.
Figure 11C:
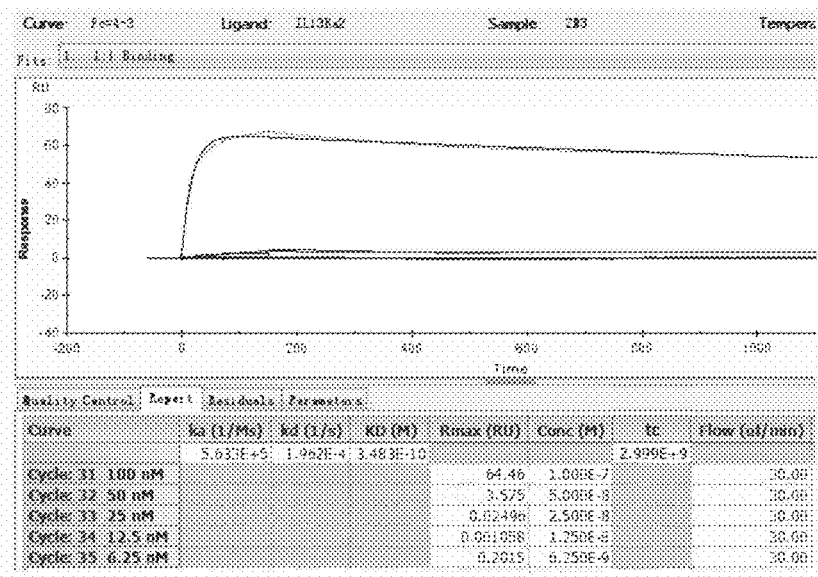
Figure 11D:
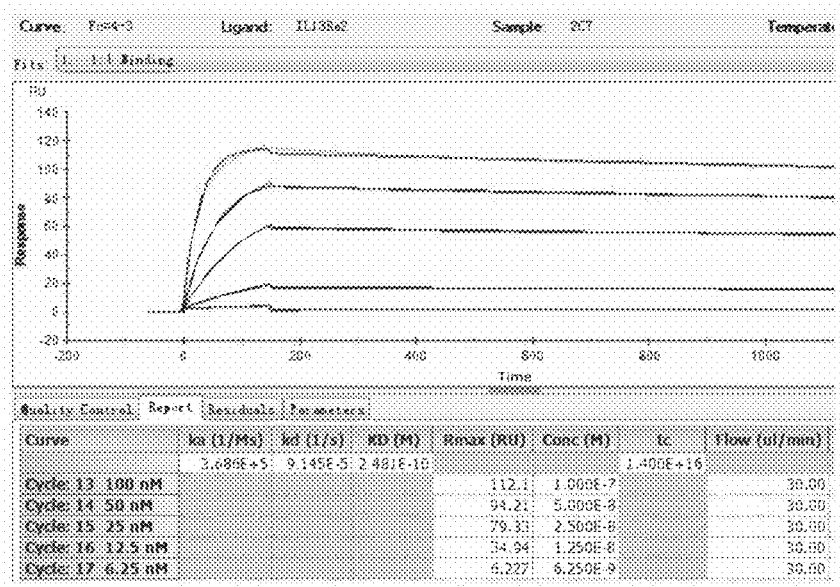
Figure 11E:
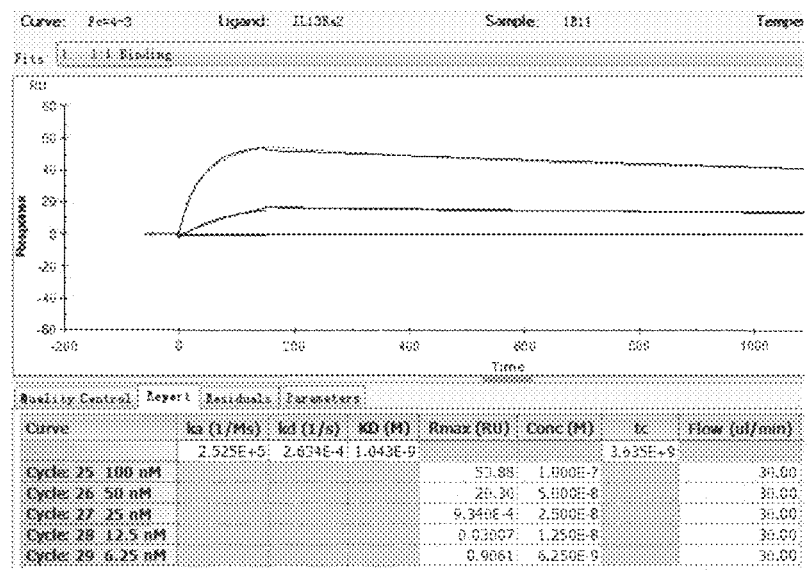
Figure 11F:
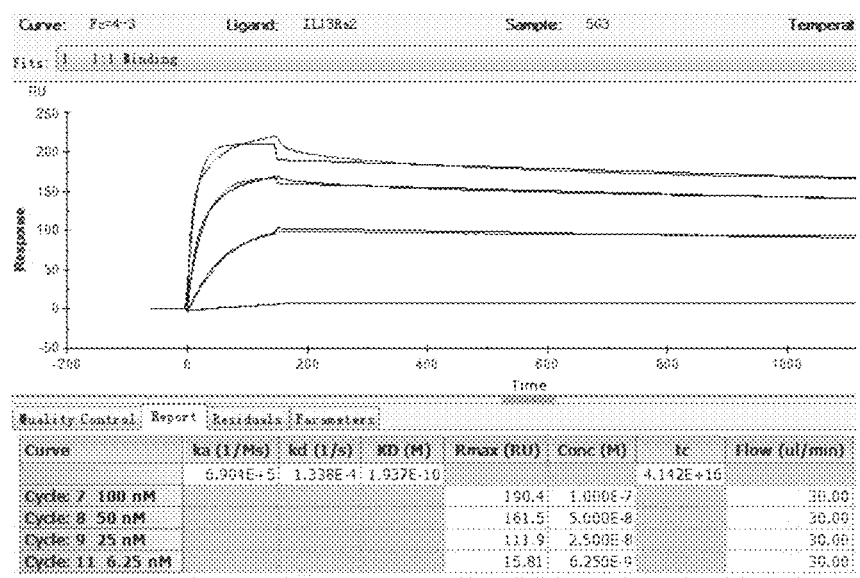
Figures 11G, 11H:
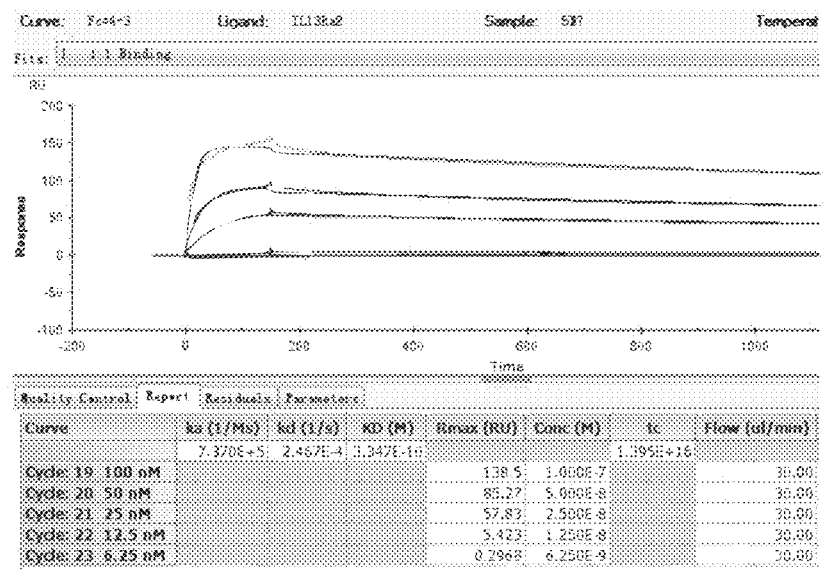

Example 5. Determination of Antibody Affinity Using the Surface Plasmon Resonance (SPR) Technology The affinity of different antibodies for IL-13RA2 was determined using biacore T200. The specific procedures were as follows:

IL-13RA2 huFc was coated on the CMS chip by amino coupling, coated to about 500 RU, and the gradiently diluted antibodies were passed through the antigen-coated channel at a flow rate of 30 ul/min as a mobile phase. The running buffer was HBS-N and the temperature was 25° C. The experimental data was analyzed by BIAevaluation 3.2 and the kinetic curves were fitted using a 1:1 langmuir model. The KD of 31C2 (scFv_Fc) was 1.79 nM, and the KD of 32H4 (scFv_Fc) was 3.76 nM (see FIG. 5).

Example 6. Determination of Binding EC50 of Antibodies to U251 Cells Using FACs

Cells were harvested, washed once with a growth medium, and resuspended in PBS, and the cell concentration was adjusted to 4E+5 cells/ml. The gradiently diluted scFv_Fc fusion antibody was incubated with the cells for 30 minutes on ice, and the antibody was 5-fold serially diluted with 500 nM as the initial concentration, into 8 gradients. Then the mixture was incubated with a FITC-labeled anti-human IgG secondary antibody. After two washing steps, detection was performed using a Guava easyCyte™ HT System instrument. The results are shown as in FIG. 6, in which both antibodies have a concentration gradient-dependent binding to U251 cells, 31C2 (ScFv_Fc) has an EC50 of 2.8 nM, and 32H4 (ScFv_Fc) has an EC50 of 1 nM.

Example 7. Affinity Maturation of Antibodies

Affinity maturation was performed using the phage display technology.

Using 31C2 and 32H4 as parent antibodies, two phage libraries were constructed respectively: one having randomized light chain CDR1 and CDR2, and the other having randomized heavy chain CDR1 and CDR2. The libraries were then panned for the antigen, and high affinity antibodies, i.e. variants of 31C2 and 32H4, were screened by the SPR technology and the like. The information of primers is shown in FIG. 7.

The template plasmid was first constructed based on the antibody 31C2 (scFv) (having an amino acid sequence of SEQ ID NO: 25, and a nucleic acid sequence of SEQ ID NO: 26). For phage libraries with randomized light chain CDR1 and CDR2, fragment 1 was amplified by PCR using primers LMF and IL1R; fragment 2 was amplified by PCR using primers IL2F and FdR; then fragment 1 and fragment 2 were ligated by bridging PCR to obtain the full-length scFv containing randomized sequences, then the full-length fragment was digested with NcoI and NotI, and ligated by T4 ligase into the template plasmid digested likewise, and the plasmid was electro-transformed into TG1 competent cells with a library capacity of 1.68E+9. For phage libraries with randomized heavy chain CDR1 and CDR2, fragment 3 was amplified by PCR using primers LMF and BH1R; fragment 4 was amplified by PCR using primers BH2F and FdR; then fragment 3 and fragment 4 were ligated by bridging PCR to obtain the full-length scFv containing randomized sequences, then the full-length fragment was digested with NcoI and NotI, and ligated by T4 ligase into the template plasmid digested likewise, and the plasmid was electro-transformed into TG1 competent cells with a library capacity of 1.75E+9.

The construction of affinity maturation library of antibody 32H4 was similar to that of 31C2, and the template plasmid was constructed based on the antibody 32H4 (scFv) (having an amino acid sequence of SEQ ID NO: 26, and a nucleic acid sequence of SEQ ID NO: 27). The light chain CDR1 and CDR2 were randomized using the same primers as those for 31C2, and the resulting phage library capacity was 2.1 E+9. Similarly, the heavy chain CDR1 and CDR2 were randomized using the same primers as those for 31C2, and the resulting phage library capacity were 1.5 E+9.

Example 8. Screening of Phage Libraries

Reference can be made to the method in Example 2 of the patent. The initial concentration of the antigen IL13RA2 huFc was 50 nM and a 2-fold gradient dilution was performed for the next round of screening. Panning was performed for 2-3 cycles to enrich for scFv phage clones that specifically bind to IL13RA2 huFc. Positive clones were determined by standard ELISA methods for IL13RA2 huFc. Human IL13RA1_huFc segment was used in the ELISA as an unrelated antigen to verify the specificity of the antibody. A total of 111 ELISA-positive clones were picked up; and the dissociation constant Kd of the induced supernatant was determined by biacore after re-induction. Among them, 10 clones had a dissociation constant Kd more than 10 times lower than that of the parent clone, as shown in FIG. 8.

By sequencing, the light chains of clones 2C7, 2D3, 1D11, 1B11, 2A5, 2D4, 1H7 and 1D8 were identical to the light chain of 31C2 (having an amino acid sequence of SEQ ID NO: 4, and a nucleic acid sequence of SEQ ID NO: 3). The heavy chain amino acid sequences of clones 2C7 (having an amino acid of SEQ ID NO: 29, and a nucleic acid sequence of SEQ ID NO: 30), 2D3 (having an amino acid of SEQ ID NO: 31, and a nucleic acid sequence of SEQ ID NO: 32), 1D11 (having an amino acid of SEQ ID NO: 33, and a nucleic acid sequence of SEQ ID NO: 34), 1B11 (having an amino acid of SEQ ID NO: 35, and a nucleic acid sequence of SEQ ID NO: 36), 2A5 (having an amino acid of SEQ ID NO: 37, and a nucleic acid sequence of SEQ ID NO: 38), 2D4 (having an amino acid of SEQ ID NO: 39, and a nucleic acid sequence of SEQ ID NO: 40), 1H7 (having an amino acid of SEQ ID NO: 41, and a nucleic acid sequence of SEQ ID NO: 42), 1D8 (having an amino acid of SEQ ID NO: 43, and a nucleic acid sequence of SEQ ID NO: 44) and 31C2 (having an amino acid of SEQ ID NO: 2, and a nucleic acid sequence of SEQ ID NO: 1) were compared in FIG. 9A.

In the affinity matured clones of 31C2, the sequences of HCDR1 are shown as in SEQ ID NOs: 45-51, respectively, and the sequences of HCDR2 are shown as in SEQ ID NOs: 52-58, respectively. See FIG. 9B for detail.

Compared with the VH of the parental antibody 31C2, 2C7 has mutations of 4 sites, with 96.7% similarity; 2D3 has mutations of 5 sites, with 95.8% similarity; 1D11 has mutations of 6 sites, with 95% similarity; 1B11 has mutations of 5 sites, with 95.8% similarity; 2A5 has mutations of 4 sites, with 96.7% similarity; 2D4 has mutations of 5 sites, with 95.8% similarity; 1H7 has mutations of 4 sites, with 96.7% similarity; and 1D8 has mutations of 4 sites, with 96.7% similarity.

By sequencing, the light chains of clones 5G3 and 5D7 were identical to the light chain of 32H4 (having an amino acid sequence of SEQ ID NO: 8, and a nucleic acid sequence of SEQ ID NO: 7). The heavy chain amino acid sequences of clones 5G3 (having an amino acid sequence of SEQ ID NO: 59, and a nucleic acid sequence of SEQ ID NO: 60), 5D7 (having an amino acid sequence of SEQ ID NO: 61, and a nucleic acid sequence of SEQ ID NO: 62), and 32H4 (having an amino acid sequence of SEQ ID NO: 6, and a nucleic acid sequence of SEQ ID NO: 5) were compared in FIG. 9C.

In the affinity matured clones of 32H4, the sequences of HCDR1 are shown as in SEQ ID NOs: 63 and 64, respectively, and the sequences of HCDR2 are shown as in SEQ ID NOs: 65 and 66, respectively. See FIG. 9D for detail.

Compared with the VH of the parental antibody 32H4, 5G3 has mutations of 5 sites, with 95.7% similarity; 2D3 has mutations of 5 sites, with 95.8% similarity; 5D7 has mutations of 8 sites, with 95% similarity; and 1B11 has mutations of 5 sites, with 93.2% similarity.

Example 9. Expression and Purification of scFv

The TG1 containing the antibody gene was streaked for culture, single clones were picked up and inoculated into 2×TY-Amp-5% Glucose medium, and cultured at 37° C., at 220 rpm to OD600 nM=0.8-0.9, and IPTG was added to a final concentration of 1 mM, followed by incubation at 220 rpm at 25° C. overnight to induce scFv expression.

The strains were collected by centrifugation, suspended in 30 mM Tris HCl, 20% sucrose, and 1 mM EDTA (pH 8.0) (80 ml per gram of strains), ice-bathed, and centrifuged at 4° C. at 8000 g. The supernatant A was taken, the precipitate was suspended with 8 ml of 5 mM MgSO4, ice-bathed, gently shaken for 10 minutes, and centrifuged at 4° C. at 8000 g, and the supernatant B was taken. Supernatant A and supernatant B were combined, centrifuged at 12,000 g for 15 minutes, and the supernatant was taken as the cold osmotic shock fluid.

Affinity purification was performed using a nickel column, affinity was measured using biacore T200, and the association and dissociation constants of the affinity matured antibodies are shown as in FIG. 10A.

The specificity of the antibodies 5D7, 2C7, 5G3, 2D4, 2D3 and 1B11 was determined by standard ELISA following the method of Example 3. The results were shown as in FIG. 10B. Clones 1B11, 2C7, 2D3 and 2D4 from the parent antibody 31C2 specifically bind to human IL13RA2, do not bind to human IL13RA1, and cross-react with murine IL13RA2. The clones 5D7 and 5G3 from the parental antibody 32H4 specifically bind to human IL13RA2, do not bind to human IL13RA1, and do not bind to murine IL13RA2.

Example 10. Expression and Affinity Determination of the scFv_Fc Forms of Antibodies The six antibodies 5D7, 2C7, 5G3, 2D4, 2D3 and 1B11 with higher affinity were picked up for construction of the scFv_Fc fusion form.

Referring to Example 4, a suitable restriction site and a protective base were introduced upstream of the VH, and a suitable restriction site and a protective base were introduced downstream of the VL. The PCR product was analyzed by 1% agarose gel electrophoresis, purified and recovered. After enzymatic digestion, the product was ligated into the eukaryotic expression vector V152 containing the human Fc segment (purchased from ShangHai Raygene Biotechnology Co., Ltd.). The vector was transiently transfected into 30 ml of 293F cells by 293Fectin and expressed. The culture supernatant was collected 5-7 days after transfection, and subjected to affinity purification by Protein A. The aggregation of the antibodies was analyzed by SEC. The result is shown as in FIG. 11.

Affinity was determined using the method of Example 5 using biacore T200, and the results are shown as in FIGS. 11B-11G. The affinity matured antibodies have the affinity 3 to 10 times higher than that of the parent antibody. The association and dissociation constants of the antibodies are shown as in FIG. 11F.

Figure 12:
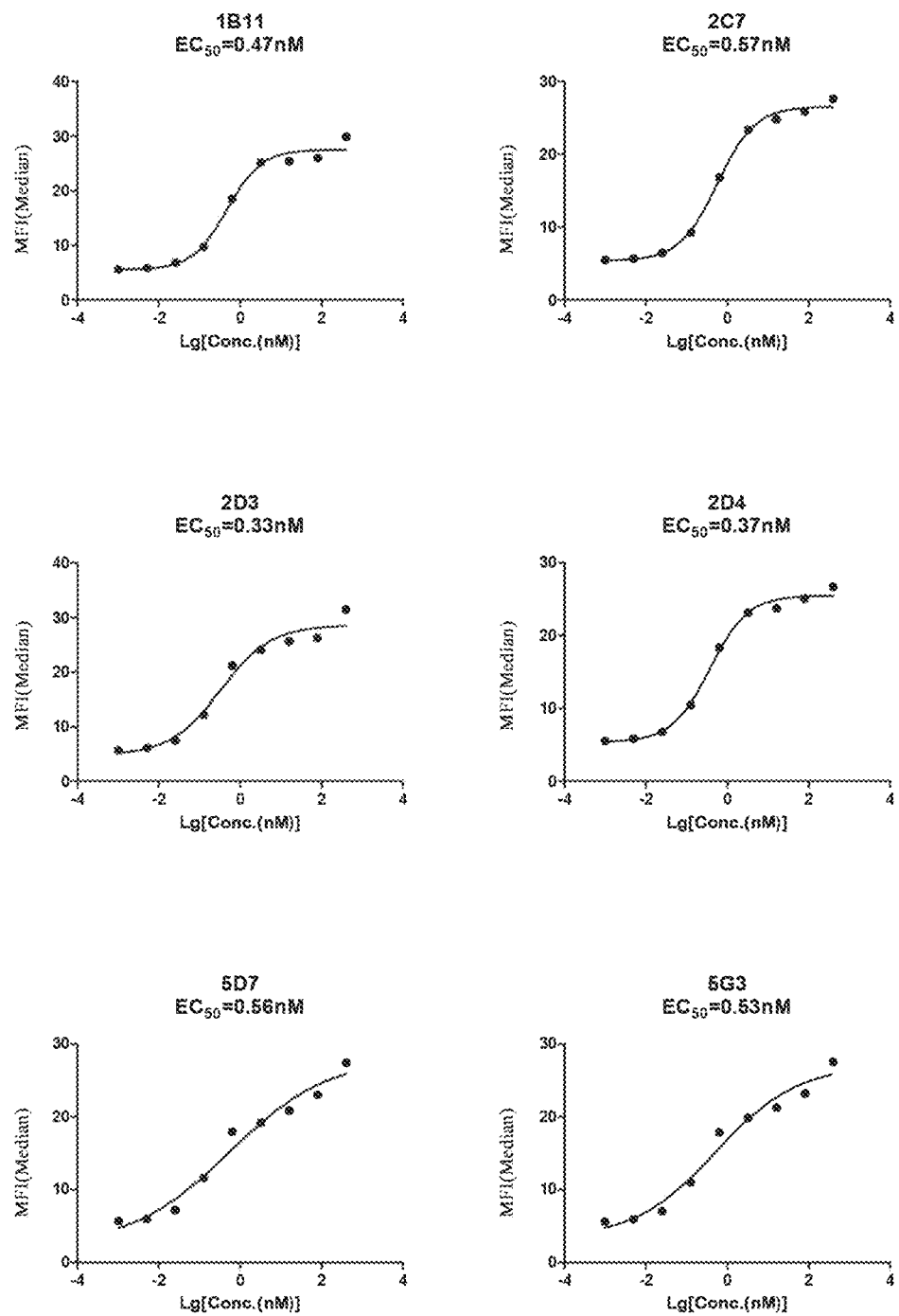
FIG. 12 shows EC50 of binding of scFv_Fc forms of antibodies 5D7, 2C7, 5G3, 2D4, 2D3, and 1B11 to U251 cells.

Example 11. Determination of EC50 of Binding of scFv_Fc Forms of Antibodies to U251 Cells Following the method of Example 6, cells were harvested, washed once with a growth medium, and resuspended in PBS, and the cell concentration was adjusted to 4E+5 cells/ml. The gradiently diluted scFv_Fc fusion antibody was incubated with the cells for 30 minutes on ice, and the antibody was 5-fold serially diluted with 2,000 nM as the initial concentration, into 11 gradients. Then the mixture was incubated with a FITC-labeled anti-human IgG secondary antibody. After two washing steps, detection was performed using a Guava easyCyte™ HT System instrument. The results are shown as in FIG. 12: the EC50s of binding of the scFv_Fc forms of antibodies 5D7, 2C7, 5G3, 2D4, 2D3 and 1B11 to U251 cells were 0.56 nM, 0.57 nM, 0.53 nM, 0.37 nM, 0.33 nM and 0.47 nM, respectively. There is also a 2-8 fold increase compared with the parent antibody.

Example 12. Preparation of CAR-T Cells

2D4 and 5G3 were selected for CAR-T cell preparation and anti-tumor activity studies.

1. Construction of Lentiviral Packaging Plasmid pRRL-hu8E3-28Z

Using PRRLSIN-cPPT.EF-1α as the vector, lentiviral plasmids expressing the chimeric antigen receptors of antibodies 2D4 and 5G3 were constructed, including PRRLSIN-cPPT.EF-1α-2D4-28Z, PRRLSIN-cPPT.EF-1α-2D4-BBZ, PRRLSIN-cPPT.EF-1α-2D4-28BBZ and PRRLSIN-cPPT.EF-1α-5G3-28Z, PRRLSIN-cPPT.EF-1α-5G3-BBZ, PRRLSIN-cPPT.EF-1α-5G3-28BBZ.

The 2D4-28Z sequence consists of CD8a signal peptide (SEQ ID NO: 68), 2D4scFv (SEQ ID NO: 67), CD8 hinge (SEQ ID NO: 69), CD28 transmembrane region (SEQ ID NO: 70) and intracellular signaling domain (SEQ ID NO: 71), and the intracellular segment CD3ζ (SEQ ID NO: 72) of CD3.

The 2D4-BBZ sequence consists of CD8a signal peptide (SEQ ID NO: 68), 2D4scFv (SEQ ID NO: 67), CD8 hinge (SEQ ID NO: 69), CD8 transmembrane region (SEQ ID NO: 73), CD137 intracellular signaling domain (SEQ ID NO: 74), and the intracellular segment CD3ζ (SEQ ID NO: 72) of CD3.

The 2D4-28BBZ sequence consists of CD8a signal peptide (SEQ ID NO: 68), 2D4scFv (SEQ ID NO: 67), CD8 hinge (SEQ ID NO: 69), CD28 transmembrane region (SEQ ID NO: 70) and intracellular signaling domain (SEQ ID NO: 71), the intracellular signaling domain of CD137 (SEQ ID NO: 74), and the intracellular segment CD3ζ (SEQ ID NO: 72) of CD3.

The 5G3-28Z sequence consists of CD8a signal peptide (SEQ ID NO: 68), 5G3scFv (SEQ ID NO: 75), CD8 hinge (SEQ ID NO: 69), CD28 transmembrane region (SEQ ID NO: 70) and intracellular signaling domain (SEQ ID NO: 71), and the intracellular segment CD3ζ (SEQ ID NO: 72) of CD3.

The 5G3-BBZ sequence consists of CD8a signal peptide (SEQ ID NO: 68), 5G3scFv (SEQ ID NO: 75), CD8 hinge (SEQ ID NO: 69), CD8 transmembrane region (SEQ ID NO: 73), CD137 intracellular signaling domain (SEQ ID NO: 74), and the intracellular segment CD3ζ (SEQ ID NO: 72) of CD3.

The 5G3-28BBZ sequence consists of CD8a signal peptide (SEQ ID NO: 68), 5G3scFv (SEQ ID NO: 75), CD8 hinge (SEQ ID NO: 69), CD28 transmembrane region (SEQ ID NO: 70) and intracellular signaling domain (SEQ ID NO: 71), the intracellular signaling domain of CD137 (SEQ ID NO: 74), and the intracellular segment CD3ζ(SEQ ID NO: 72) of CD3.

2. Lentiviral Packaging, Virus Concentration and Titer Determination of the CAR Lentiviral Vector Targeting IL13Ra2

293T cells were seeded at a density of $1.7 \times 10^7$ in a 15 cm culture dish, and the medium is DMEM containing 10% fetal bovine serum (BioWest). 13.73 μg of the target gene plasmids PRRLSIN-2D4-28Z, PRRLSIN-2D4-BBZ, PRRLSIN-2D4-28BBZ, PRRLSIN-5G3-28Z, PRRLSIN-5G3-BBZ and PRRLSIN-5G3-28BBZ and 16.4 μg of packaging plasmids pRsv-REV, 16.4 μg of RRE-PMDLg, and 6.4 μg of Vsvg were respectively dissolved in 2,048 μL of a blank DMEM culture liquid, and mixed well.

158.4 μg of PEI (1 μg/μl) was dissolved in 2,048 μl of serum-free DMEM culture liquid, mixed well and incubated at room temperature. The plasmid mixture was added to the PEI mixture and incubated at room temperature for 20 min. 4.096 ml of the transfection complex was added dropwise to a 15 cm culture dish containing 20 ml of DMEM medium. After 4-5 hours, the transfected 293T cells were exchanged with 10% FBS DMEM medium, and incubated at 37° C. for 72 h. The supernatant of the virus solution was collected and concentrated, and the virus titer was determined. The concentrated virus titers were:

2D4-28Z: $3.89E \times 10^8$ U/ml,
2D4-BBZ: $3.08E \times 10^8$ U/ml,
2D4-28BBZ: $2.72E \times 10^8$ U/ml,
5G3-28Z: $3.7E \times 10^8$ U/ml,
5G3-BBZ: $1.88E \times 10^8$ U/ml, and
5G3-28BBZ: $3.11E \times 10^8$ U/ml, respectively.

3. Lentiviral Transduction of T Lymphocytes—Preparation of CAR-Positive T Lymphocytes Activation of T lymphocytes: T lymphocytes were added to a lymphocyte culture medium liquid at a density of about $5 \times 10^5$/mL, and magnetic beads (Invitrogen) coated with an anti-CD3 antibody and an anti-CD28 antibody at the same time were added at a magnetic beads:cell ratio of 2:1, and recombinant human IL-2 (Shanghai Huaxin Biotechnology Co., Ltd.) with a final concentration of 500 U/mL was added for stimulation and cultured for 24-48 hours;

Coating of a 24-well plate with retronectin: 380 μl of 5 μg/ml retronectin solution (PBS) was added to each well and incubated at 4° C. overnight. The retronectin solution (PBS) in the 24-well plate was discarded, followed by washing with 1 ml PBS twice, washing with the medium once (wells being kept moist); the cells were inoculated in a 24-well plate coated with retronectin, with the number of cells per well being $5 \times 10^5$ and the volume of the culture solution being 500 μl; the concentrated lentivirus was added to the PBMC cells with MOI of 15, centrifuged at 32° C. at 1200 g for 60 min, transferred to a cell incubator, and after virus infection for 24 h, the culture liquid was centrifuged at a low speed (300 rpm, 10 min, large centrifuge) for changing the culture liquid. Magnetic beads can be removed 3 to 4 days after infection.

4. Expression of T Lymphocyte Chimeric Antigen Receptor

Lentivirus-infected T lymphocytes were cultured, and on day 7, $1 \times 10^6$ T cells were taken, aliquoted into two portions, centrifuged at 4° C. at 5000 rpm for 5 min, the supernatant was discarded, and the remainder was washed with PBS twice. Cells of the control group were incubated with 50 μl of PE-SA (1:200 dilution) antibody on ice for 45 min, washed with PBS (2% NBS) twice, and resuspended as a control. Cells of the test group were incubated with 50 μl of 1:50 diluted biotin-Goat Anti human IgG, F(ab')2 antibody on ice for 45 min, and washed with PBS (2% NBS) twice; 50 μl of PE-SA (1:200 dilution) antibody was added and incubated on ice for 45 min; 2 ml PBS (2% NBS) was added to resuspend the cells, and centrifuged at 4° C. at 5000 rpm/min for 5 minutes, the supernatant was discarded, and the process was repeated twice; the proportion of CAR-positive T cells was detected by a flow cytometer.

5. Cytotoxicity Assay of CART Cells Targeting IL13Ra2

When comparing the in vitro killing activity of UTD, 2D4-28Z, 2D4-BBZ, 2D4-28BBZ, 5G3-28Z, 5G3-BBZ, 5G3-28BBZ CAR T cells, the positive rates of infection for the six CAR T cells were 66.0%, 26.3%, 34.8%, 59.9%, 35.5% and 23.8%, respectively.

50 ul of RMPI+10% fetal bovine serum (Gibco)+double antibody was added to each of three E-Plate 16 respectively, and placed on a real-time monitor to adjust the baseline.

Target cells: 50 ul of 1×104/mL U251 cells were inoculated into an E-Plate 16 plate respectively, stood for 30-40 min, and placed on the real-time monitor to start monitoring; Effector cells: After 18 hours, UTD and CAR T cells expressing different chimeric antigen receptors were added at an effector:target ratio of 3:1, 1:1 or 1:3;

Two duplicate wells were provided in each group, and the average of two duplicate wells was taken. The detection time was at 38 h.

Each experimental group and each control group are as follows:

Each experimental group: each target cell+CAR T expressing different chimeric antigen receptors;
Control group 1: target cells
Control group 2: blank medium;

The calculation formula of cytotoxicity is: % cytotoxicity=[(experimental group−effector cell spontaneous group−target cell spontaneous group)/(target cell max−target cell spontaneous)]*100

Figure 13:
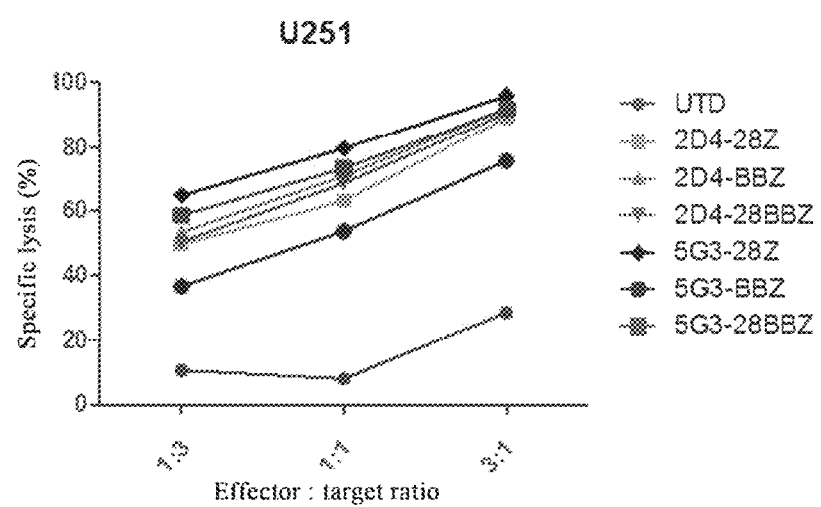
FIG. 13 shows the in vitro killing activity of different CAR-T cells.

The experimental results are shown as in FIG. 13. Each of the CAR T cells expressing different chimeric antigen receptors had significant in vitro killing activity against IL13Ra2-positive cells.

All the documents mentioned in the invention are recited as reference, as if each document is recited as reference individually. In addition, it should be understood that after reading the teachings of the invention described above, those skilled in the art can make various changes or modifications of the invention, and these equivalent forms shall also fall into the scope of the present application as defined by the appended claims.

---

What is claimed is:

1. An antibody that specifically binds interleukin-13 receptor subunit alpha 2 (IL-13RA2), wherein the antibody comprises a light chain variable region and a heavy chain variable region, and wherein the antibody comprises:
   (i) the LCDR1 amino acid sequence as shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 9, the HCDR2 amino acid sequence as shown in SEQ ID NO: 10, and the HCDR3 amino acid sequence as shown in SEQ ID NO: 11;
   (ii) the LCDR1 amino acid sequence as shown in SEQ ID NO: 13, the LCDR2 amino acid sequence as shown in SEQ ID NO: 14, the LCDR3 amino acid sequence as shown in SEQ ID NO:16; the HCDR1 amino acid sequence as shown in SEQ ID NO: 9, the HCDR2 amino acid sequence as shown in SEQ ID NO: 10, and the HCDR3 amino acid sequence as shown in SEQ ID NO: 12;
   (iii) the LCDR1 amino acid sequence as shown in SEQ ID NO: 13, the LCDR2 amino acid sequence as shown in SEQ ID NO: 14, the LCDR3 amino acid sequence as shown in SEQ ID NO:16; the HCDR1 amino acid sequence as shown in SEQ ID NO: 64, the HCDR2 amino acid sequence as shown in SEQ ID NO: 66, and the HCDR3 amino acid sequence as shown in SEQ ID NO: 12;
   (iv) the LCDR1 amino acid sequence as shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 45, the HCDR2 amino acid sequence as shown in SEQ ID NO: 52, and the HCDR3 amino acid sequence as shown in SEQ ID NO: 11;
   (v) the LCDR1 amino acid sequence as shown in SEQ ID NO: 13, the LCDR2 amino acid sequence as shown in SEQ ID NO: 14, the LCDR3 amino acid sequence as shown in SEQ ID NO:16; the HCDR1 amino acid sequence as shown in SEQ ID NO: 63, the HCDR2 amino acid sequence as shown in SEQ ID NO: 65, and the HCDR3 amino acid sequence as shown in SEQ ID NO: 12;
   (vi) the LCDR1 amino acid sequence shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 50, the HCDR2 amino acid sequence as shown in SEQ ID NO: 56, and the HCDR3 amino acid sequence as shown in SEQ ID NO: 11;
   (vii) the LCDR1 amino acid sequence as shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 46, the HCDR2 amino acid sequence as shown in SEQ ID NO: 52, and the HCDR3 amino acid sequence as shown in SEQ ID NO: 11;
   (viii) the LCDR1 amino acid sequence as shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 48, the HCDR2 amino acid sequence as shown in SEQ ID NO: 54, and the HCDR3 amino acid sequence as shown in SEQ ID NO: 11;
   (ix) the LCDR1 amino acid sequence as shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 47, the HCDR2 amino acid sequence as shown in SEQ ID NO: 53, and the HCDR3 amino acid sequence as shown in SEQ ID NO: 11;
   (x) the LCDR1 amino acid sequence as shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 49, the HCDR2 amino acid sequence as shown in SEQ ID NO: 55, and the HCDR3 amino acid sequence as shown in SEQ ID NO: 11;
   (xi) the LCDR1 amino acid sequence as shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 51, the HCDR2 amino acid sequence as shown in SEQ ID NO: 57, and the HCDR3 amino acid sequence as shown in SEQ ID NO: 11; or
   (xii) the LCDR1 amino acid sequence as shown in SEQ ID NO: 13, the LCDR2 amino acid sequence as shown in SEQ ID NO: 14, the LCDR3 amino acid sequence as shown in SEQ ID NO:15; the HCDR1 amino acid sequence as shown in SEQ ID NO: 49, the HCDR2 amino acid sequence as shown in SEQ ID NO: 58, and the HCDR3 amino acid sequence as shown in SEQ ID NO: 11.

2. The antibody of claim 1, wherein the antibody comprises
a light chain variable region comprising an amino acid sequence as shown in SEQ ID NO: 4 or an amino acid sequence at least 90% identical thereto.

3. The antibody of claim 1, wherein the heavy chain variable region comprises the amino acid sequence as shown in SEQ ID NO: 2 or an amino acid sequence at least 90% identical of SEQ ID NO:2.

4. The antibody of claim 3, wherein the heavy chain variable region of the antibody comprises the amino acid sequence as shown in SEQ ID NO: 2 or an amino acid sequence at least 96% identical thereto.

5. The antibody of claim 3, wherein the heavy chain variable region of the antibody comprises the amino acid sequence as shown in SEQ ID NO: 2 or an amino acid sequence at least 97% identical thereto.

6. The antibody of claim 3, wherein the heavy chain variable region of the antibody comprises the amino acid sequence as shown in SEQ ID NO: 2 or an amino acid sequence at least 98% identical thereto.

7. The antibody of claim 3, wherein the heavy chain variable region of the antibody comprises the amino acid sequence as shown in SEQ ID NO: 2 or an amino acid sequence at least 99% identical thereto.

8. The antibody of claim 1, wherein
(i) the light chain variable region comprises the amino acid sequence as shown in SEQ ID NO: 4 and the heavy chain variable region comprises the amino acid sequence as shown in SEQ ID NO: 2;
(ii) the light chain variable region comprises the amino acid sequence shown in SEQ ID NO: 8 and the heavy chain variable region comprises the amino acid sequence shown in SEQ ID NO: 6;
(iii) the light chain variable region comprises the amino acid sequence shown in SEQ ID NO: 8 and the heavy chain variable region comprises the amino acid sequence shown in SEQ ID NO: 61;
(iv) the light chain variable region comprises the amino acid sequence shown in SEQ ID NO: 4 and the heavy chain variable region comprises the amino acid sequence shown in SEQ ID NO: 29;
(v) the light chain variable region comprises the amino acid sequence shown in SEQ ID NO: 8 and the heavy chain variable region comprises the amino acid sequence shown in SEQ ID NO: 59;
(vi) the light chain variable region comprises the amino acid sequence shown in SEQ ID NO: 4 and the heavy chain variable region comprises the amino acid sequence shown in SEQ ID NO: 39;
(vii) the light chain variable region comprises the amino acid sequence shown in SEQ ID NO: 4 and the heavy chain variable region comprises the amino acid sequence shown in SEQ ID NO: 31;
(viii) the light chain variable region comprises the amino acid sequence shown in SEQ ID NO: 4 and the heavy chain variable region comprises the amino acid sequence shown in SEQ ID NO: 35;
(ix) the light chain variable region comprises the amino acid sequence shown in SEQ ID NO: 4 and the heavy chain variable region comprises the amino acid sequence shown in SEQ ID NO: 33;
(x) the light chain variable region comprises the amino acid sequence shown in SEQ ID NO: 4 and the heavy chain variable region comprises the amino acid sequence shown in SEQ ID NO: 37;
(xi) the light chain variable region comprises the amino acid sequence shown in SEQ ID NO: 4 and the heavy chain variable region comprises the amino acid sequence shown in SEQ ID NO: 41; or
(xii) the light chain variable region comprises the amino acid sequence shown in SEQ ID NO: 4 and the heavy chain variable region comprises the amino acid sequence shown in SEQ ID NO: 43.

9. A pharmaceutical composition, comprising:
the antibody of claim 1;
and a pharmaceutically acceptable carrier or excipient.

10. The antibody of claim 1, wherein the antibody comprises a heavy chain variable region comprising the amino acid sequence as shown in SEQ ID NO: 2, 29, 31, 33, 35, 37, 39, 41, or 43.

11. The antibody of claim 1, wherein the antibody comprises a light chain variable region comprising the amino acid sequence shown in SEQ ID NO: 4 and a heavy chain variable region comprising the amino acid sequence shown in SEQ ID NO: 2, 29, 31, 33, 35, 37, 39, 41, or 43.

12. An antibody that specifically binds interleukin-13 receptor subunit alpha 2 (IL-13RA2), wherein
(i) the light chain variable region comprises the amino acid sequence shown in SEQ ID NO: 4 and the heavy chain variable region comprises the amino acid sequence as shown in SEQ ID NO: 2;
(ii) the light chain variable region comprises the amino acid sequence shown in SEQ ID NO: 4 and the heavy chain variable region comprises the amino acid sequence shown in SEQ ID NO: 29;
(iii) the light chain variable region comprises the amino acid sequence shown in SEQ ID NO: 4 and the heavy chain variable region comprises the amino acid sequence shown in SEQ ID NO: 39;
(iv) the light chain variable region comprises the amino acid sequence shown in SEQ ID NO: 4 and the heavy chain variable region comprises the amino acid sequence shown in SEQ ID NO: 31;
(v) the light chain variable region comprises the amino acid sequence shown in SEQ ID NO: 4 and the heavy chain variable region comprises the amino acid sequence shown in SEQ ID NO: 35;
(vi) the light chain variable region comprises the amino acid sequence shown in SEQ ID NO: 4 and the heavy chain variable region comprises the amino acid sequence shown in SEQ ID NO: 33;
(vii) the light chain variable region comprises the amino acid sequence shown in SEQ ID NO: 4 and the heavy chain variable region comprises the amino acid sequence shown in SEQ ID NO: 37;
(viii) the light chain variable region comprises the amino acid sequence shown in SEQ ID NO: 4 and the heavy chain variable region comprises the amino acid sequence shown in SEQ ID NO: 41; or
(viv) the light chain variable region comprises the amino acid sequence shown in SEQ ID NO: 4 and the heavy chain variable region comprises the amino acid sequence shown in SEQ ID NO: 43.

13. An antibody that specifically binds interleukin-13 receptor subunit alpha 2 (IL-13RA2), wherein the heavy chain variable region comprises the amino acid sequence as shown in SEQ ID NO: 2 or an amino acid sequence at least 90% identical thereto, and the light chain variable region comprises the amino acid sequence shown in SEQ ID NO: 4.

* * * * *

SEQUENCE LISTING

```
<160> NUMBER OF SEQ ID NOS: 83

<210> SEQ ID NO 1
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 31C2 VH

<400> SEQUENCE: 1
gaggtgcaat tgctggagtc tgggggaggc ttggtacagc ctgggggtc cctgagactc        60 tcctgtgcag cctccggatt caccttagc agttatgcca tgagctgggt ccgccaggct       120
ccagggaagg ggctggagtg ggtctcagct attagtggta gtggtggtag cacatactac      180
gcagactccg tgaagggccg gttcaccatc tccagagaca attccaagaa cacgctgtat      240
ctgcagatga acagcctgag agccgaggac acggccgtat attactgtgc gaaagttcgt      300
tacggttggg gtgcaggtgc attcgactac tggggccaag gaaccctggt caccgtctcg      360
agt                                                                    363

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 31C2 VH

<400> SEQUENCE: 2

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30
```

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser
        115                 120
```

<210> SEQ ID NO 3
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 31C2 VL

<400> SEQUENCE: 3

```
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tacgatacct acccaccaat cacgtttggc   300
cagggcacca aagtcgagat caag                                          324
```

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 31C2VL

<400> SEQUENCE: 4

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Pro Pro
                85                  90                  95

Ile Thr Phe Gly Gln Gly Thr Lys Val Glu Ile Lys
            100                 105
```

<210> SEQ ID NO 5

<210> SEQ ID NO 5
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 32H4 VH

<400> SEQUENCE: 5

```
gaggtgcaat tgctggagtc tgggggaggc ttggtacagc ctgggggtc cctgagactc      60 tcctgtgcag cctccggatt cacctttagc agttatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcagatga acagcctgag agccgaggac acggccgtat attactgtgc gcgtgttgca     300
ttctctggtt ctttcgacta ctggggccaa ggaaccctgg tcaccgtctc gagt           354
```

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 32H4 VH

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Phe Ser Gly Ser Phe Asp Tyr Trp Gly Gln Gly Thr
            100                 105                 110

Leu Val Thr Val Ser Ser
        115
```

<210> SEQ ID NO 7
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 32H4 VL

<400> SEQUENCE: 7

```
gacatccaga tgacccagtc tccttccacc ctgtctgcat ctgtaggaga ccgtgtcacc      60
atcacttgcc gtgccagtca gagtattagt agctggttgg cctggtatca gcagaaacca    120
gggaaagccc ctaagctcct gatctatgat gcctccagtt tggaaagtgg ggtcccatca    180
```
cgtttcagcg gcagtggatc cgggacagaa ttcactctca ccatcagcag cttgcagcct    240
gatgattttg caacttatta ctgccaacag agaaacagat acccaccaac gtttggccag    300
ggcaccaaag tcgagatcaa g                                              321

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 32H4 VL

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Arg Asn Arg Tyr Pro Pro
                85                  90                  95

Thr Phe Gly Gln Gly Thr Lys Val Glu Ile Lys
            100                 105

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ser Tyr Ala Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 31C2&32H4 HCDR2

<400> SEQUENCE: 10

Ala Ile Ser Gly Ser Gly Gly Ser Thr Tyr Tyr Ala Asp Ser Val Lys
1               5                   10                  15

Gly

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: 31C2 HCDR3

<400> SEQUENCE: 11

Val Arg Tyr Gly Trp Gly Ala Gly Ala Phe Asp Tyr
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 32H4 HCDR3

<400> SEQUENCE: 12

Val Ala Phe Ser Gly Ser Phe Asp Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 31C2&32H4 LCDR1

<400> SEQUENCE: 13

Arg Ala Ser Gln Ser Ile Ser Ser Trp Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 31C2&32H4 LCDR2

<400> SEQUENCE: 14

Asp Ala Ser Ser Leu Glu Ser
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 31C2 LCDR3

<400> SEQUENCE: 15

Gln Gln Tyr Asp Thr Tyr Pro Pro Ile Thr
1               5                   10

<210> SEQ ID NO 16
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: 32H4 LCDR3

<400> SEQUENCE: 16

Gln Gln Arg Asn Arg Tyr Pro Pro Thr
1               5

<210> SEQ ID NO 17
<211> LENGTH: 951
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL13Ra2 ECD

<400> SEQUENCE: 17

```
gacaccgaga taaaagttaa ccctcctcag gattttgaga tagtggatcc cggatactta      60
ggttatctct atttgcaatg gcaaccccca ctgtctctgg atcattttaa ggaatgcaca     120
gtggaatatg aactaaaata ccgaaacatt ggtagtgaaa catggaagac catcattact     180
aagaatctac attacaaaga tgggtttgat cttaacaagg gcattgaagc gaagatacac     240
acgcttttac catggcaatg cacaaatgga tcagaagttc aaagttcctg ggcagaaact     300
acttattgga tatcaccaca aggaattcca gaaactaaag ttcaggatat ggattgcgta     360
tattacaatt ggcaatattt actctgttct tggaaacctg gcataggtgt acttcttgat     420
accaattaca acttgttta ctggtatgag ggcttggatc atgcattaca gtgtgttgat     480
tacatcaagg ctgatggaca aaatatagga tgcagatttc cctatttgga ggcatcagac     540
tataaagatt tctatatttg tgttaatgga tcatcagaga acaagcctat cagatccagt     600
tatttcactt ttcagcttca aaatatagtt aaacctttgc cgccagtcta tcttactttt     660
actcgggaga gttcatgtga aattaagctg aaatggagca taccctttggg acctattcca     720
gcaaggtgtt ttgattatga aattgagatc agagaagatg atactacctt ggtgactgct     780
acagttgaaa atgaaacata caccttgaaa acaacaaatg aaacccgaca attatgcttt     840
gtagtaagaa gcaaagtgaa tatttattgc tcagatgacg gaatttggag tgagtggagt     900
gataaacaat gctgggaagg tgaagaccta tcgaagaaaa ctttgctacg t            951
```

<210> SEQ ID NO 18
<211> LENGTH: 317
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL13Ra2 ECD

<400> SEQUENCE: 18

Asp Thr Glu Ile Lys Val Asn Pro Pro Gln Asp Phe Glu Ile Val Asp
1               5                   10                  15

Pro Gly Tyr Leu Gly Tyr Leu Tyr Leu Gln Trp Gln Pro Pro Leu Ser
            20                  25                  30

Leu Asp His Phe Lys Glu Cys Thr Val Glu Tyr Glu Leu Lys Tyr Arg
        35                  40                  45

Asn Ile Gly Ser Glu Thr Trp Lys Thr Ile Ile Thr Lys Asn Leu His
    50                  55                  60

Tyr Lys Asp Gly Phe Asp Leu Asn Lys Gly Ile Glu Ala Lys Ile His
65                  70                  75                  80

Thr Leu Leu Pro Trp Gln Cys Thr Asn Gly Ser Glu Val Gln Ser Ser
            85                  90                  95

Trp Ala Glu Thr Thr Tyr Trp Ile Ser Pro Gln Gly Ile Pro Glu Thr
        100                 105                 110

Lys Val Gln Asp Met Asp Cys Val Tyr Tyr Asn Trp Gln Tyr Leu Leu
        115                 120                 125

Cys Ser Trp Lys Pro Gly Ile Gly Val Leu Leu Asp Thr Asn Tyr Asn
130                 135                 140

Leu Phe Tyr Trp Tyr Glu Gly Leu Asp His Ala Leu Gln Cys Val Asp
145                 150                 155                 160

Tyr Ile Lys Ala Asp Gly Gln Asn Ile Gly Cys Arg Phe Pro Tyr Leu
                165                 170                 175

Glu Ala Ser Asp Tyr Lys Asp Phe Tyr Ile Cys Val Asn Gly Ser Ser
            180                 185                 190

Glu Asn Lys Pro Ile Arg Ser Ser Tyr Phe Thr Phe Gln Leu Gln Asn
        195                 200                 205

Ile Val Lys Pro Leu Pro Pro Val Tyr Leu Thr Phe Thr Arg Glu Ser
210                 215                 220

Ser Cys Glu Ile Lys Leu Lys Trp Ser Ile Pro Leu Gly Pro Ile Pro
225                 230                 235                 240

Ala Arg Cys Phe Asp Tyr Glu Ile Glu Ile Arg Glu Asp Asp Thr Thr
                245                 250                 255

Leu Val Thr Ala Thr Val Glu Asn Glu Thr Tyr Thr Leu Lys Thr Thr
            260                 265                 270

Asn Glu Thr Arg Gln Leu Cys Phe Val Val Arg Ser Lys Val Asn Ile
        275                 280                 285

Tyr Cys Ser Asp Asp Gly Ile Trp Ser Glu Trp Ser Asp Lys Gln Cys
290                 295                 300

Trp Glu Gly Glu Asp Leu Ser Lys Lys Thr Leu Leu Arg
305                 310                 315

<210> SEQ ID NO 19
<211> LENGTH: 964
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL13Ra1 ECD

<400> SEQUENCE: 19
gggcgggggc gccgcgccta cggaaactca gccacctgtg acaaatttga gtgtctctgt      60
tgaaaacctc tgcacagtaa tatggacatg gaatccaccc gagggagcca gctcaaattg     120
tagtctatgg tattttagtc attttggcga caaacaagat aagaaaatag ctccggaaac     180
tcgtcgttca atagaagtac ccctgaatga gaggatttgt ctgcaagtgg ggtcccagtg     240
tagcaccaat gagagtgaga agcctagcat tttggttgaa aaatgcatct cacccccaga     300
aggtgatcct gagtctgctg tgactgagct tcaatgcatt tggcacaacc tgagctacat     360
gaagtgttct tggctccctg aaggaatac cagtcccgac actaactata ctctctacta      420
ttggcacaga agcctggaaa aaattcatca atgtgaaaac atctttagag aaggccaata     480
ctttggttgt tcctttgatc tgaccaaagt gaaggattcc agttttgaac aacacagtgt     540

-continued

```
ccaaataatg gtcaaggata atgcaggaaa aattaaacca tccttcaata tagtgccttt    600
aacttcccgt gtgaaacctg atcctccaca tattaaaaac ctctccttcc acaatgatga    660
cctatatgtg caatgggaga atccacagaa ttttattagc agatgcctat tttatgaagt    720
agaagtcaat aacagccaaa ctgagacaca taatgttttc tacgtccaag aggctaaatg    780
tgagaatcca gaatttgaga gaaatgtgga gaatacatct tgtttcatgg tccctggtgt    840
tcttcctgat actttgaaca cagtcagaat aagagtcaaa acaaataagt tatgctatga    900
ggatgacaaa ctctggagta attggagcca agaaatgagt ataggtaaga agcgcaattc    960
caca                                                                 964
```

<210> SEQ ID NO 20
<211> LENGTH: 322
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: IL13Ra1 ECD

<400> SEQUENCE: 20

```
Gly Gly Gly Gly Ala Ala Pro Thr Glu Thr Gln Pro Pro Val Thr Asn
1               5                   10                  15

Leu Ser Val Ser Val Glu Asn Leu Cys Thr Val Ile Trp Thr Trp Asn
            20                  25                  30

Pro Pro Glu Gly Ala Ser Ser Asn Cys Ser Leu Trp Tyr Phe Ser His
        35                  40                  45

Phe Gly Asp Lys Gln Asp Lys Lys Ile Ala Pro Glu Thr Arg Arg Ser
    50                  55                  60

Ile Glu Val Pro Leu Asn Glu Arg Ile Cys Leu Gln Val Gly Ser Gln
65                  70                  75                  80

Cys Ser Thr Asn Glu Ser Glu Lys Pro Ser Ile Leu Val Glu Lys Cys
                85                  90                  95

Ile Ser Pro Pro Glu Gly Asp Pro Glu Ser Ala Val Thr Glu Leu Gln
            100                 105                 110

Cys Ile Trp His Asn Leu Ser Tyr Met Lys Cys Ser Trp Leu Pro Gly
        115                 120                 125

Arg Asn Thr Ser Pro Asp Thr Asn Tyr Thr Leu Tyr Tyr Trp His Arg
    130                 135                 140

Ser Leu Glu Lys Ile His Gln Cys Glu Asn Ile Phe Arg Glu Gly Gln
145                 150                 155                 160

Tyr Phe Gly Cys Ser Phe Asp Leu Thr Lys Val Lys Asp Ser Ser Phe
                165                 170                 175

Glu Gln His Ser Val Gln Ile Met Val Lys Asp Asn Ala Gly Lys Ile
            180                 185                 190

Lys Pro Ser Phe Asn Ile Val Pro Leu Thr Ser Arg Val Lys Pro Asp
        195                 200                 205

Pro Pro His Ile Lys Asn Leu Ser Phe His Asn Asp Asp Leu Tyr Val
    210                 215                 220

Gln Trp Glu Asn Pro Gln Asn Phe Ile Ser Arg Cys Leu Phe Tyr Glu
225                 230                 235                 240

Val Glu Val Asn Asn Ser Gln Thr Glu Thr His Asn Val Phe Tyr Val
                245                 250                 255

Gln Glu Ala Lys Cys Glu Asn Pro Glu Phe Glu Arg Asn Val Glu Asn
```

```
            260              265              270
Thr Ser Cys Phe Met Val Pro Gly Val Leu Pro Asp Thr Leu Asn Thr
        275              280              285

Val Arg Ile Arg Val Lys Thr Asn Lys Leu Cys Tyr Glu Asp Asp Lys
    290              295              300

Leu Trp Ser Asn Trp Ser Gln Glu Met Ser Ile Gly Lys Lys Arg Asn
305              310              315              320

Ser Thr

<210> SEQ ID NO 21
<211> LENGTH: 1638
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL13Ra2 ECD_huFc

<400> SEQUENCE: 21
gacaccgaga taaaagttaa ccctcctcag gattttgaga tagtggatcc cggatactta      60
ggttatctct atttgcaatg caacccccca ctgtctctgg atcatttta aggaatgcaca    120
gtggaatatg aactaaaata ccgaaacatt ggtagtgaaa catggaagac catcattact    180
aagaatctac attacaaaga tgggtttgat cttaacaagg cattgaagc gaagatacac    240
acgcttttac catggcaatg cacaaatgga tcagaagttc aaagttcctg gcagaaaact    300
acttattgga tatcaccaca aggaattcca gaaactaaag ttcaggatat ggattgcgta    360
tattacaatt ggcaatattt actctgttct tggaaacctg gcataggtgt acttcttgat    420
accaattaca acttgtttta ctggtatgag ggcttggatc atgcattaca gtgtgttgat    480
tacatcaagg ctgatggaca aaatatagga tgcagatttc cctatttgga ggcatcagac    540
tataaagatt tctatatttg tgttaatgga tcatcagaga acaagcctat cagatccagt    600
tatttcactt ttcagcttca aaatatagtt aaacctttgc cgccagtcta tcttactttt    660
actcgggaga gttcatgtga aattaagctg aaatggagca tacctttggg acctattcca    720
gcaaggtgtt ttgattatga aattgagatc agagaagatg atactacctt ggtgactgct    780
acagttgaaa atgaaacata cacttgaaa acaacaaatg aaacccgaca attatgcttt    840
gtagtaagaa gcaaagtgaa tatttattgc tcagatgacg gaatttggag tgagtggagt    900
gataaacaat gctgggaagg tgaagaccta tcgaagaaaa cttttgctacg tggatccgac    960
aaaactcaca catgcccacc gtgcccagca cctgaactcc tggggggacc gtcagtcttc   1020
ctcttccccc caaaacccaa ggacaccctc atgatctccc ggacccctga ggtcacatgc   1080
gtggtggtgg acgtgagcca cgaagaccct gaggtcaagt tcaactggta cgtggacggc   1140
gtggaggtgc ataatgccaa gacaaagccg cgggaggagc agtacaacag cacgtaccgt   1200
gtggtcagcg tcctcaccgt cctgcaccag gactggctga atggcaagga gtacaagtgc   1260
aaggtctcca acaaagccct cccagccccc atcgagaaaa ccatctccaa agccaaaggg   1320
cagccccgag aaccacaggt gtacaccctg cccccatccc gggatgagct gaccaagaac   1380
caggtcagcc tgacctgcct ggtcaaaggc ttctatccca gcgacatcgc cgtggagtgg   1440
gagagcaatg ggcagccgga gaacaactac aagaccacgc ctcccgtgct ggactccgac   1500
ggctccttct tcctctatag caagctcacc gtggacaaga gcaggtggca gcaggggaac   1560
gtcttctcat gctccgtgat gcatgaggct ctgcacaacc actacacgca gaagagcctc   1620
```
tccctgtctc cgggtaaa                                                   1638

<210> SEQ ID NO 22
<211> LENGTH: 546
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL13Ra2 ECD_huFc

<400> SEQUENCE: 22

```
Asp Thr Glu Ile Lys Val Asn Pro Pro Gln Asp Phe Glu Ile Val Asp
1               5                   10                  15

Pro Gly Tyr Leu Gly Tyr Leu Tyr Leu Gln Trp Gln Pro Pro Leu Ser
            20                  25                  30

Leu Asp His Phe Lys Glu Cys Thr Val Glu Tyr Glu Leu Lys Tyr Arg
        35                  40                  45

Asn Ile Gly Ser Glu Thr Trp Lys Thr Ile Ile Thr Lys Asn Leu His
    50                  55                  60

Tyr Lys Asp Gly Phe Asp Leu Asn Lys Gly Ile Glu Ala Lys Ile His
65                  70                  75                  80

Thr Leu Leu Pro Trp Gln Cys Thr Asn Gly Ser Glu Val Gln Ser Ser
                85                  90                  95

Trp Ala Glu Thr Thr Tyr Trp Ile Ser Pro Gln Gly Ile Pro Glu Thr
            100                 105                 110

Lys Val Gln Asp Met Asp Cys Val Tyr Tyr Asn Trp Gln Tyr Leu Leu
        115                 120                 125

Cys Ser Trp Lys Pro Gly Ile Gly Val Leu Leu Asp Thr Asn Tyr Asn
    130                 135                 140

Leu Phe Tyr Trp Tyr Glu Gly Leu Asp His Ala Leu Gln Cys Val Asp
145                 150                 155                 160

Tyr Ile Lys Ala Asp Gly Gln Asn Ile Gly Cys Arg Phe Pro Tyr Leu
                165                 170                 175

Glu Ala Ser Asp Tyr Lys Asp Phe Tyr Ile Cys Val Asn Gly Ser Ser
            180                 185                 190

Glu Asn Lys Pro Ile Arg Ser Ser Tyr Phe Thr Phe Gln Leu Gln Asn
        195                 200                 205

Ile Val Lys Pro Leu Pro Pro Val Tyr Leu Thr Phe Thr Arg Glu Ser
    210                 215                 220

Ser Cys Glu Ile Lys Leu Lys Trp Ser Ile Pro Leu Gly Pro Ile Pro
225                 230                 235                 240

Ala Arg Cys Phe Asp Tyr Glu Ile Glu Ile Arg Glu Asp Asp Thr Thr
                245                 250                 255

Leu Val Thr Ala Thr Val Glu Asn Glu Thr Tyr Thr Leu Lys Thr Thr
            260                 265                 270

Asn Glu Thr Arg Gln Leu Cys Phe Val Val Arg Ser Lys Val Asn Ile
        275                 280                 285

Tyr Cys Ser Asp Asp Gly Ile Trp Ser Glu Trp Ser Asp Lys Gln Cys
    290                 295                 300

Trp Glu Gly Glu Asp Leu Ser Lys Lys Thr Leu Leu Arg Gly Ser Asp
305                 310                 315                 320

Lys Thr His Thr Cys Pro Pro Cys Pro Ala Pro Glu Leu Leu Gly Gly
                325                 330                 335
```

```
Pro Ser Val Phe Leu Phe Pro Pro Lys Pro Lys Asp Thr Leu Met Ile
            340                 345                 350

Ser Arg Thr Pro Glu Val Thr Cys Val Val Val Asp Val Ser His Glu
        355                 360                 365

Asp Pro Glu Val Lys Phe Asn Trp Tyr Val Asp Gly Val Glu Val His
    370                 375                 380

Asn Ala Lys Thr Lys Pro Arg Glu Glu Gln Tyr Asn Ser Thr Tyr Arg
385                 390                 395                 400

Val Val Ser Val Leu Thr Val Leu His Gln Asp Trp Leu Asn Gly Lys
                405                 410                 415

Glu Tyr Lys Cys Lys Val Ser Asn Lys Ala Leu Pro Ala Pro Ile Glu
            420                 425                 430

Lys Thr Ile Ser Lys Ala Lys Gly Gln Pro Arg Glu Pro Gln Val Tyr
        435                 440                 445

Thr Leu Pro Pro Ser Arg Asp Glu Leu Thr Lys Asn Gln Val Ser Leu
    450                 455                 460

Thr Cys Leu Val Lys Gly Phe Tyr Pro Ser Asp Ile Ala Val Glu Trp
465                 470                 475                 480

Glu Ser Asn Gly Gln Pro Glu Asn Asn Tyr Lys Thr Thr Pro Pro Val
                485                 490                 495

Leu Asp Ser Asp Gly Ser Phe Phe Leu Tyr Ser Lys Leu Thr Val Asp
            500                 505                 510

Lys Ser Arg Trp Gln Gln Gly Asn Val Phe Ser Cys Ser Val Met His
        515                 520                 525

Glu Ala Leu His Asn His Tyr Thr Gln Lys Ser Leu Ser Leu Ser Pro
    530                 535                 540

Gly Lys
545

<210> SEQ ID NO 23
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL13Ra1 ECD_huFc

<400> SEQUENCE: 23
gggggcgggg gcgccgcgcc tacggaaact cagccacctg tgacaaattt gagtgtctct      60
gttgaaaacc tctgcacagt aatatggaca tggaatccac ccgagggagc cagctcaaat     120
tgtagtctat ggtattttag tcatttggc gacaaacaag ataagaaaat agctccggaa     180
actcgtcgtt caatagaagt accccctgaat gagaggattt gtctgcaagt ggggtcccag     240
tgtagcacca atgagagtga aagcctagc attttggttg aaaaatgcat ctcaccccca     300
gaaggtgatc ctgagtctgc tgtgactgag cttcaatgca tttggcacaa cctgagctac     360
atgaagtgtt cttggctccc tggaaggaat accagtcccg acactaacta tactctctac     420
tattggcaca gaagcctgga aaaaattcat caatgtgaaa acatctttag agaaggccaa     480
tactttggtt gttcctttga tctgaccaaa gtgaaggatt ccagtttga acaacacagt     540 gtccaaataa tggtcaagga taatgcagga aaaattaaac catccttcaa tatagtgcct     600
ttaacttccc gtgtgaaacc tgatcctcca catattaaaa acctctcctt ccacaatgat     660
gacctatatg tgcaatggga gaatccacag aattttatta gcagatgcct atttatgaa     720
```

```
gtagaagtca ataacagcca aactgagaca cataatgttt tctacgtcca agaggctaaa    780
tgtgagaatc cagaatttga gagaaatgtg gagaatacat cttgtttcat ggtccctggt    840
gttcttcctg atactttgaa cacagtcaga ataagagtca aaacaaataa gttatgctat    900
gaggatgaca aactctggag taattggagc caagaaatga gtataggtaa gaagcgcaat    960
tccacaggat ccgacaaaac tcacacatgc ccaccgtgcc cagcacctga actcctgggg   1020
ggaccgtcag tcttcctctt ccccccaaaa cccaaggaca ccctcatgat ctcccggacc   1080
cctgaggtca catgcgtggt ggtggacgtg agccacgaag accctgaggt caagttcaac   1140
tggtacgtgg acggcgtgga ggtgcataat gccaagacaa agccgcggga ggagcagtac   1200
aacagcacgt accgtgtggt cagcgtcctc accgtcctgc accaggactg gctgaatggc   1260
aaggagtaca agtgcaaggt ctccaacaaa gccctcccag cccccatcga aaaaccatc    1320 tccaaagcca agggcagcc ccgagaacca caggtgtaca ccctgccccc atcccgggat    1380
gagctgacca agaaccaggt cagcctgacc tgcctggtca aaggcttcta tcccagcgac   1440
atcgccgtgg agtgggagag caatgggcag ccggagaaca actacaagac cacgcctccc   1500
gtgctggact ccgacggctc cttcttcctc tatagcaagc tcaccgtgga caagagcagg   1560
tggcagcagg ggaacgtctt ctcatgctcc gtgatgcatg aggctctgca caaccactac   1620
acgcagaaga gcctctccct gtctccgggt aaa                                1653
```

```
<210> SEQ ID NO 24
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL13Ra1 ECD_huFc

<400> SEQUENCE: 24

Gly Gly Gly Gly Ala Ala Pro Thr Glu Thr Gln Pro Pro Val Thr Asn
1               5                   10                  15

Leu Ser Val Ser Val Glu Asn Leu Cys Thr Val Ile Trp Thr Trp Asn
            20                  25                  30

Pro Pro Glu Gly Ala Ser Ser Asn Cys Ser Leu Trp Tyr Phe Ser His
        35                  40                  45

Phe Gly Asp Lys Gln Asp Lys Lys Ile Ala Pro Glu Thr Arg Arg Ser
    50                  55                  60

Ile Glu Val Pro Leu Asn Glu Arg Ile Cys Leu Gln Val Gly Ser Gln
65                  70                  75                  80

Cys Ser Thr Asn Glu Ser Glu Lys Pro Ser Ile Leu Val Glu Lys Cys
                85                  90                  95

Ile Ser Pro Pro Glu Gly Asp Pro Glu Ser Ala Val Thr Glu Leu Gln
            100                 105                 110

Cys Ile Trp His Asn Leu Ser Tyr Met Lys Cys Ser Trp Leu Pro Gly
        115                 120                 125

Arg Asn Thr Ser Pro Asp Thr Asn Tyr Thr Leu Tyr Tyr Trp His Arg
    130                 135                 140

Ser Leu Glu Lys Ile His Gln Cys Glu Asn Ile Phe Arg Glu Gly Gln
145                 150                 155                 160

Tyr Phe Gly Cys Ser Phe Asp Leu Thr Lys Val Lys Asp Ser Ser Phe
                165                 170                 175

Glu Gln His Ser Val Gln Ile Met Val Lys Asp Asn Ala Gly Lys Ile
```

180                 185                 190
Lys Pro Ser Phe Asn Ile Val Pro Leu Thr Ser Arg Val Lys Pro Asp
            195                 200                 205

Pro Pro His Ile Lys Asn Leu Ser Phe His Asn Asp Asp Leu Tyr Val
        210                 215                 220

Gln Trp Glu Asn Pro Gln Asn Phe Ile Ser Arg Cys Leu Phe Tyr Glu
225                 230                 235                 240

Val Glu Val Asn Ser Gln Thr Glu Thr His Asn Val Phe Tyr Val
            245                 250                 255

Gln Glu Ala Lys Cys Glu Asn Pro Glu Phe Glu Arg Asn Val Glu Asn
            260                 265                 270

Thr Ser Cys Phe Met Val Pro Gly Val Leu Pro Asp Thr Leu Asn Thr
        275                 280                 285

Val Arg Ile Arg Val Lys Thr Asn Lys Leu Cys Tyr Glu Asp Asp Lys
        290                 295                 300

Leu Trp Ser Asn Trp Ser Gln Glu Met Ser Ile Gly Lys Lys Arg Asn
305                 310                 315                 320

Ser Thr Gly Ser Asp Lys Thr His Thr Cys Pro Pro Cys Pro Ala Pro
            325                 330                 335

Glu Leu Leu Gly Gly Pro Ser Val Phe Leu Phe Pro Pro Lys Pro Lys
            340                 345                 350

Asp Thr Leu Met Ile Ser Arg Thr Pro Glu Val Thr Cys Val Val Val
        355                 360                 365

Asp Val Ser His Glu Asp Pro Glu Val Lys Phe Asn Trp Tyr Val Asp
        370                 375                 380

Gly Val Glu Val His Asn Ala Lys Thr Lys Pro Arg Glu Glu Gln Tyr
385                 390                 395                 400

Asn Ser Thr Tyr Arg Val Val Ser Val Leu Thr Val Leu His Gln Asp
            405                 410                 415

Trp Leu Asn Gly Lys Glu Tyr Lys Cys Lys Val Ser Asn Lys Ala Leu
        420                 425                 430

Pro Ala Pro Ile Glu Lys Thr Ile Ser Lys Ala Lys Gly Gln Pro Arg
        435                 440                 445

Glu Pro Gln Val Tyr Thr Leu Pro Pro Ser Arg Asp Glu Leu Thr Lys
    450                 455                 460

Asn Gln Val Ser Leu Thr Cys Leu Val Lys Gly Phe Tyr Pro Ser Asp
465                 470                 475                 480

Ile Ala Val Glu Trp Glu Ser Asn Gly Gln Pro Glu Asn Asn Tyr Lys
            485                 490                 495

Thr Thr Pro Pro Val Leu Asp Ser Asp Gly Ser Phe Phe Leu Tyr Ser
        500                 505                 510

Lys Leu Thr Val Asp Lys Ser Arg Trp Gln Gln Gly Asn Val Phe Ser
        515                 520                 525

Cys Ser Val Met His Glu Ala Leu His Asn His Tyr Thr Gln Lys Ser
530                 535                 540

Leu Ser Leu Ser Pro Gly Lys
545                 550

<210> SEQ ID NO 25
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: 31C2(scFv)

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Thr Leu Ser Ala Ser Val Gly Asp Arg Val Thr Ile Thr Cys Arg
145                 150                 155                 160

Ala Ser Gln Ser Ile Ser Ser Trp Leu Ala Trp Tyr Gln Gln Lys Pro
                165                 170                 175

Gly Lys Ala Pro Lys Leu Leu Ile Tyr Asp Ala Ser Ser Leu Glu Ser
            180                 185                 190

Gly Val Pro Ser Arg Phe Ser Gly Ser Gly Ser Gly Thr Glu Phe Thr
        195                 200                 205

Leu Thr Ile Ser Ser Leu Gln Pro Asp Asp Phe Ala Thr Tyr Tyr Cys
    210                 215                 220

Gln Gln Tyr Asp Thr Tyr Pro Pro Ile Thr Phe Gly Gln Gly Thr Lys
225                 230                 235                 240

Val Glu Ile Lys Arg
            245

<210> SEQ ID NO 26
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 31C2(scFv)

<400> SEQUENCE: 26
gaggtgcaat tgctggagtc tgggggaggc ttggtacagc ctggggggtc cctgagactc      60
tcctgtgcag cctccggatt cacctttagc agttatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcagatga acagcctgag agccgaggac acggccgtat attactgtgc gaaagttcgt     300
tacggttggg gtgcaggtgc attcgactac tggggccaag gaaccctggt caccgtctcg     360
agtggtggag gcggttcagg cggaggtggt tctggcggtg gcggatcgga catccagatg     420

```
acccagtctc cttccaccct gtctgcatct gtaggagacc gtgtcaccat cacttgccgt    480
gccagtcaga gtattagtag ctggttggcc tggtatcagc agaaaccagg gaaagcccct    540
aagctcctga tctatgatgc ctccagtttg gaaagtgggg tcccatcacg tttcagcggc    600
agtggatccg ggacagaatt cactctcacc atcagcagct tgcagcctga tgattttgca    660
acttattact gccaacagta cgatacctac ccaccaatca cgtttggcca gggcaccaaa    720
gtcgagatca agcgt                                                     735
```

<210> SEQ ID NO 27
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 32H4(scFv)

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Phe Ser Gly Ser Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Thr Leu
    130                 135                 140

Ser Ala Ser Val Gly Asp Arg Val Thr Ile Thr Cys Arg Ala Ser Gln
145                 150                 155                 160

Ser Ile Ser Ser Trp Leu Ala Trp Tyr Gln Gln Lys Pro Gly Lys Ala
                165                 170                 175

Pro Lys Leu Leu Ile Tyr Asp Ala Ser Ser Leu Glu Ser Gly Val Pro
            180                 185                 190

Ser Arg Phe Ser Gly Ser Gly Ser Gly Thr Glu Phe Thr Leu Thr Ile
        195                 200                 205

Ser Ser Leu Gln Pro Asp Asp Phe Ala Thr Tyr Tyr Cys Gln Gln Arg
    210                 215                 220

Asn Arg Tyr Pro Pro Thr Phe Gly Gln Gly Thr Lys Val Glu Ile Lys
225                 230                 235                 240

Arg
```

<210> SEQ ID NO 28
<211> LENGTH: 723
<212> TYPE: DNA
<213> ORGANISM: Artificial Sequence
<220> FEATURE:

<223> OTHER INFORMATION: Description of Artificial Sequence: Synthetic
    polynucleotide
<220> FEATURE:
<223> OTHER INFORMATION: 32H4(scFv)

<400> SEQUENCE: 28

```
gaggtgcaat tgctggagtc tgggggaggc ttggtacagc ctgggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gcgtgttgca     300
ttctctggtt ctttcgacta ctggggccaa ggaaccctgg tcaccgtctc gagtggtgga     360
ggcggttcag gcggaggtgg ttctggcggt ggcggatcgg acatccagat gacccagtct     420
ccttccaccc tgtctgcatc tgtaggagac cgtgtcacca tcacttgccg tgccagtcag     480
agtattagta gctggttggc ctggtatcag cagaaaccag ggaaagcccc taagctcctg     540
atctatgatg cctccagttt ggaaagtggg gtcccatcac gtttcagcgg cagtggatcc     600
gggacagaat tcactctcac catcagcagc ttgcagcctg atgattttgc aacttattac     660
tgccaacaga gaaacagata cccaccaacg tttggccagg gcaccaaagt cgagatcaag     720
cgt                                                                   723
```

<210> SEQ ID NO 29
<211> LENGTH: 121
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: 2C7 VH

<400> SEQUENCE: 29

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Leu Pro
            20                  25                  30

Ala Met Ser Trp Val Arg Gln Ala Pro Gly Lys Gly Leu Glu Trp Val
        35                  40                  45

Ser Ala Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser
        115                 120
```

<210> SEQ ID NO 30
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:

<223> OTHER INFORMATION: 2C7 VH

<400> SEQUENCE: 30

```
gaggtgcaat tgctggagtc tggggaggc ttggtacagc ctgggggtc cctgagactc    60
tcctgtgcag cctccggatt cacctttaaa ctgccggcca tgagctgggt ccgccaggct   120
ccagggaagg ggctggagtg ggtctcagca attactggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaagttcgt   300
tacggttggg gtgcaggtgc attcgactac tggggccaag aaccctggt caccgtctcg    360
agt                                                                  363
```

<210> SEQ ID NO 31
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2D3 VH

<400> SEQUENCE: 31

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Arg Pro
            20                  25                  30

Ala Met Thr Trp Val Arg Gln Ala Pro Gly Lys Gly Leu Glu Trp Val
        35                  40                  45

Ser Ala Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Val Arg Tyr Gly Trp Gly Ala Gly Ala Phe Asp Tyr Trp Gly
            100                 105                 110

Gln Gly Thr Leu Val Thr Val Ser Ser
        115                 120
```

<210> SEQ ID NO 32
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 2D3 VH

<400> SEQUENCE: 32

```
gaggtgcaat tgctggagtc tggggaggc ttggtacagc ctgggggtc cctgagactc    60
tcctgtgcag cctccggatt cacctttcgc agacctgcca tgacatgggt ccgccaggct   120
ccagggaagg ggctggagtg ggtctcagca attacaggta gtggtggtag tacatactac   180
gcagactccg tgaagggccg gttcaccatc tccagagaca attccaagaa cacgctgtat   240
ctgcagatga acagcctgag agccgaggac acggccgtat attactgtgt gaaagttcgt   300
tacggttggg gtgcaggtgc attcgactac tggggccaag aaccctggt caccgtctcg    360
```

```
agt                                                                     363

<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1D11 VH

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Thr Ile
            20                  25                  30

Pro Met Ser Trp Val Arg Gln Ala Pro Gly Lys Gly Leu Glu Trp Val
        35                  40                  45

Ser Ser Ile Ser Gly Ser Ala Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser
        115                 120

<210> SEQ ID NO 34
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 1D11 VH

<400> SEQUENCE: 34
gaggtgcaat tgctggagtc tgggggaggc ttggtacagc ctggggggtc cctgagactc      60
tcctgtgcag cctccggatt cacctttgga acaattccca tgagctgggt ccgccaggct    120
ccagggaagg ggctggagtg ggtctcatcc attagtggta gtgctggtag cacatactac    180
gcagactccg tgaagggccg gttcaccatc tccagagaca attccaagaa cacgctgtat    240
ctgcagatga acagcctgag agccgaggac acggccgtat attactgtgc gaaagttcgt    300
tacggttggg gtgcaggtgc attcgactac tggggccaag aaccctggt caccgtctcg      360 agt                                                                     363

<210> SEQ ID NO 35
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1B11 VH

<400> SEQUENCE: 35
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asp
            20                  25                  30

Ala Leu Asn Trp Val Arg Gln Ala Pro Gly Lys Gly Leu Glu Trp Val
            35                  40                  45

Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser
            115                 120
```

<210> SEQ ID NO 36
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 1B11 VH

<400> SEQUENCE: 36

```
gaggtgcaat tgctggagtc tgggggaggc ttggtacagc ctggggggtc cctgagactc      60
tcctgtgcag cctccggatt cacctttagc agggatgctt tgaactgggt ccgccaggct     120
ccagggaagg ggctggagtg gtctcagct attagtggta gtggtggtag cacattttac     180
gcagactccg tgaagggccg gttcaccatc tccagagaca attccaagaa cacgctgtat     240
ctgcagatga acagcctgag agccgaggac acggccgtat attactgtgc gaaagttcgt     300
tacggttggg gtgcaggtgc attcgactac tggggccaag gaaccctggt caccgtctcg     360
agt                                                                   363
```

<210> SEQ ID NO 37
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 2A5 VH

<400> SEQUENCE: 37

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Asn Trp Val Arg Gln Ala Pro Gly Lys Gly Leu Glu Trp Val
            35                  40                  45

Ser Ala Ile Ser Ala Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser
        115                 120

<210> SEQ ID NO 38
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 2A5 VH

<400> SEQUENCE: 38
gaggtgcaat tgctggagtc tgggggaggc ttggtacagc ctgggggtc cctgagactc      60 tcctgtgcag cctccggatt cacctttagc aggtatgcca tgaactgggt ccgccaggct    120
ccagggaagg gctggagtg gtctcagct attagtgcta gtggtggtgg acatactac       180 gcagactccg tgaagggccg gttcaccatc tccagagaca attccaagaa cacgctgtat    240
ctgcagatga acagcctgag agccgaggac acggccgtat attactgtgc gaaagttcgt    300
tacggttggg gtgcaggtgc attcgactac tggggccaag aaccctggt caccgtctcg    360 agt                                                                   363

<210> SEQ ID NO 39
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2D4 VH

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Lys Tyr
            20                  25                  30

Ala Met Gly Trp Val Arg Gln Ala Pro Gly Lys Gly Leu Glu Trp Val
        35                  40                  45

Ser Gly Ile Ser Gly Ser Val Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser
        115                 120

<210> SEQ ID NO 40
<211> LENGTH: 363
<212> TYPE: DNA
<213> ORGANISM: Artificial Sequence
```

<220> FEATURE:
<223> OTHER INFORMATION: Description of Artificial Sequence: Synthetic
      polynucleotide
<220> FEATURE:
<223> OTHER INFORMATION: 2D4 VH

<400> SEQUENCE: 40
gaggtgcaat tgctggagtc tgggggaggc ttggtacagc ctgggggtc cctgagactc      60 tcctgtgcag cctccggatt cacctttcgc aagtatgcca tgggctgggt ccgccaggct    120
ccagggaagg ggctggagtg ggtctcaggt attagtggta gtgttggtag cacatactac    180
gcagactccg tgaagggccg gttcaccatc tccagagaca attccaagaa cacgctgtat    240
ctgcagatga acagcctgag agccgaggac acggccgtat attactgtgc gaaagttcgt    300
tacggttggg gtgcaggtgc attcgactac tggggccaag gaaccctggt caccgtctcg    360
agt                                                                  363

<210> SEQ ID NO 41
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1H7 VH

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Arg Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser
        115                 120

<210> SEQ ID NO 42
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 1H7 VH

<400> SEQUENCE: 42
gaggtgcaat tgctggagtc tgggggaggc ttggtacagc ctgggggtc cctgagactc      60 tcctgtgcag cctccggatt cacctttcgt cgctatgcca tgagctgggt ccgccaggct    120
ccagggaagg ggctggagtg ggtctcaggt attagcggga gtggtggtgg acatactac    180 gcagactccg tgaagggccg gttcaccatc tccagagaca attccaagaa cacgctgtat    240

```
ctgcagatga acagcctgag agccgaggac acggccgtat attactgtgc gaaagttcgt    300
tacggttggg gtgcaggtgc attcgactac tggggccaag aaccctggt caccgtctcg    360 agt                                                                  363
```

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1D8 VH

<400> SEQUENCE: 43

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Asn Trp Val Arg Gln Ala Pro Gly Lys Gly Leu Glu Trp Val
        35                  40                  45

Ser Ala Ile Asn Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser
        115                 120
```

<210> SEQ ID NO 44
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 1D8 VH

<400> SEQUENCE: 44

```
gaggtgcaat tgctggagtc tgggggaggc ttggtacagc ctgggggtc cctgagactc    60 tcctgtgcag cctccggatt cacctttagc agatacgcca tgaactgggt ccgccaggct    120
ccagggaagg gctggagtg gtctcagct attaatgcaa gtgaggtag cacatactac    180 gcagactccg tgaagggccg gttcaccatc tccagagaca attccaagaa cacgctgtat    240
ctgcagatga acagcctgag agccgaggac acggccgtat attactgtgc gaaagttcgt    300
tacggttggg gtgcaggtgc attcgactac tggggccaag aaccctggt caccgtctcg    360 agt                                                                  363
```

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: 2C7 HCDR1

<400> SEQUENCE: 45

Lys Leu Pro Ala Met Ser
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2D3 HCDR1

<400> SEQUENCE: 46

Arg Arg Pro Ala Met Thr
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1D11 HCDR1

<400> SEQUENCE: 47

Gly Thr Ile Pro Met Ser
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1B11 HCDR1

<400> SEQUENCE: 48

Ser Arg Asp Ala Leu Asn
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2A5&1D8 HCDR1

<400> SEQUENCE: 49

Ser Arg Tyr Ala Met Asn
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<223> OTHER INFORMATION: 2D4 HCDR1

<400> SEQUENCE: 50

Arg Lys Tyr Ala Met Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1H7 HCDR1

<400> SEQUENCE: 51

Arg Arg Tyr Ala Met Ser
1               5

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2C7&2D3 HCDR2

<400> SEQUENCE: 52

Ala Ile Thr Gly Ser Gly Gly Ser Thr Tyr Tyr Ala Asp Ser Val Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1D11 HCDR2

<400> SEQUENCE: 53

Ser Ile Ser Gly Ser Ala Gly Ser Thr Tyr Tyr Ala Asp Ser Val Lys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1B11 HCDR2

<400> SEQUENCE: 54

Ala Ile Ser Gly Ser Gly Gly Ser Thr Phe Tyr Ala Asp Ser Val Lys
1               5                   10                  15

Gly
```

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2A5 HCDR2

<400> SEQUENCE: 55

Ala Ile Ser Ala Ser Gly Gly Thr Tyr Tyr Ala Asp Ser Val Lys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2D4 HCDR2

<400> SEQUENCE: 56

Gly Ile Ser Gly Ser Val Gly Ser Thr Tyr Tyr Ala Asp Ser Val Lys
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1H7 HCDR2

<400> SEQUENCE: 57

Gly Ile Ser Gly Ser Gly Gly Gly Thr Tyr Tyr Ala Asp Ser Val Lys
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1D8 HCDR2

<400> SEQUENCE: 58

Ala Ile Asn Ala Ser Gly Gly Ser Thr Tyr Tyr Ala Asp Ser Val Lys
1               5                   10                  15

Gly

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic

```
                            polypeptide
<220> FEATURE:
<223> OTHER INFORMATION: 5G3 VH

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Leu Ser Trp Val Arg Gln Ala Pro Gly Lys Gly Leu Glu Trp Val
        35                  40                  45

Ser Ala Ile Arg Gly Ser Ala Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Phe Ser Gly Ser Phe Asp Tyr Trp Gly Gln Gly Thr
            100                 105                 110

Leu Val Thr Val Ser Ser
        115

<210> SEQ ID NO 60
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5G3 VH

<400> SEQUENCE: 60
gaggtgcaat tgctggagtc tgggggaggc ttggtacagc ctggggggtc cctgagactc      60
tcctgtgcag cctccggatt cacctttagc agttacgtcc tgagctgggt ccgccaggct    120
ccagggaagg gctggagtg gtctcagca attaggggta gtgctggtaa cacatactac      180
gcagactccg tgaagggccg gttcaccatc tccagagaca attccaagaa cacgctgtat    240
ctgcagatga acagcctgag agccgaggac acggccgtat attactgtgc gcgtgttgca    300
ttctctggtt ctttcgacta ctggggccaa ggaaccctgg tcaccgtctc gagt          354

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5D7 VH

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Arg Ser Ser Gly Gly Arg Thr Phe Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Ala Phe Ser Gly Ser Phe Asp Tyr Trp Gly Gln Gly Thr
        100                 105                 110

Leu Val Thr Val Ser Ser
        115

<210> SEQ ID NO 62
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5D7 VH

<400> SEQUENCE: 62
gaggtgcaat tgctggagtc tgggggaggc ttggtacagc ctgggggtc cctgagactc       60 tcctgtgcag cctccggatt cacctttagc aactatgcaa tgagctgggt ccgccaggct      120
ccagggaagg gctggagtg gtctcaggc attcgtagta gtggtggtcg cacattctac        180
gcagactccg tgaagggccg gttcaccatc tccagagaca attccaagaa cacgctgtat      240
ctgcagatga acagcctgag agccgaggac acggccgtat attactgtgc gcgtgttgca      300
ttctctggtt ctttcgacta ctggggccaa ggaaccctgg tcaccgtctc gagt            354

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 5G3 HCDR1

<400> SEQUENCE: 63

Ser Ser Tyr Val Leu Ser
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 5D7 HCDR1

<400> SEQUENCE: 64

Ser Asn Tyr Ala Met Ser
1               5

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: 5G3 HCDR2

<400> SEQUENCE: 65

Ala Ile Arg Gly Ser Ala Gly Asn Thr Tyr Tyr Ala Asp Ser Val Lys
1               5                   10                  15

Gly

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 5D7 HCDR2

<400> SEQUENCE: 66

Gly Ile Arg Ser Ser Gly Gly Arg Thr Phe Tyr Ala Asp Ser Val Lys
1               5                   10                  15

Gly

<210> SEQ ID NO 67
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2D4 scFv

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Lys Tyr
            20                  25                  30

Ala Met Gly Trp Val Arg Gln Ala Pro Gly Lys Gly Leu Glu Trp Val
        35                  40                  45

Ser Gly Ile Ser Gly Ser Val Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Tyr Gly Trp Gly Ala Gly Ala Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Thr Leu Ser Ala Ser Val Gly Asp Arg Val Thr Ile Thr Cys Arg
145                 150                 155                 160

Ala Ser Gln Ser Ile Ser Ser Trp Leu Ala Trp Tyr Gln Gln Lys Pro
                165                 170                 175

Gly Lys Ala Pro Lys Leu Leu Ile Tyr Asp Ala Ser Ser Leu Glu Ser
            180                 185                 190

Gly Val Pro Ser Arg Phe Ser Gly Ser Gly Ser Gly Thr Glu Phe Thr
        195                 200                 205

Leu Thr Ile Ser Ser Leu Gln Pro Asp Asp Phe Ala Thr Tyr Tyr Cys
    210                 215                 220

Gln Gln Tyr Asp Thr Tyr Pro Pro Ile Thr Phe Gly Gln Gly Thr Lys
225                 230                 235                 240

Val Glu Ile Lys Arg
            245

<210> SEQ ID NO 68
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CD8alpha signal peptide

<400> SEQUENCE: 68 atggcttac cagtgaccgc cttgctcctg ccgctggcct tgctgctcca cgccgccagg    60
ccg                                                                63

<210> SEQ ID NO 69
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CD8 hinge

<400> SEQUENCE: 69
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                   135

<210> SEQ ID NO 70
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CD28 transmembrane region

<400> SEQUENCE: 70
ttttgggtgc tggtggtggt tggtggagtc ctggcttgct atagcttgct agtaacagtg    60
gcctttatta ttttctgggt g                                              81

<210> SEQ ID NO 71
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CD28 intracellular domain

<400> SEQUENCE: 71
aggagtaaga ggagcaggct cctgcacagt gactacatga acatgactcc ccgccgcccc    60
gggccaaccc gcaagcatta ccagccctat gccccaccac gcgacttcgc agcctatcgc   120
tcc                                                                                        123

<210> SEQ ID NO 72
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CD3Z domain

<400> SEQUENCE: 72
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgcag agaaggaaga accctcagga aggcctgtac     180
aatgaactgc agaaagataa gatggcggag gcctacagtg agattgggat gaaaggcgag     240
cgccggaggg gcaaggggca cgatggcctt taccagggtc tcagtacagc caccaaggac     300
acctacgacg cccttcacat gcaggccctg ccccctcgc                            339

<210> SEQ ID NO 73
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CD8 transmembrane

<400> SEQUENCE: 73
atctacatct gggcgcccct tggccgggact tgtggggtcc ttctcctgtc actggttatc     60
acc                                                                    63

<210> SEQ ID NO 74
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CD137 intracellular signaling domain

<400> SEQUENCE: 74
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

<210> SEQ ID NO 75
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5G3 scFv

<400> SEQUENCE: 75

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Val Leu Ser Trp Val Arg Gln Ala Pro Gly Lys Gly Leu Glu Trp Val
            35                  40                  45

Ser Ala Ile Arg Gly Ser Ala Gly Asn Thr Tyr Tyr Ala Asp Ser Val
 50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Arg Val Ala Phe Ser Gly Ser Phe Asp Tyr Trp Gly Gln Gly Thr
            100                 105                 110

Leu Val Thr Val Ser Ser Gly Gly Gly Ser Gly Gly Gly Gly Ser
            115                 120                 125

Gly Gly Gly Gly Ser Asp Ile Gln Met Thr Gln Ser Pro Ser Thr Leu
            130                 135                 140

Ser Ala Ser Val Gly Asp Arg Val Thr Ile Thr Cys Arg Ala Ser Gln
145                 150                 155                 160

Ser Ile Ser Ser Trp Leu Ala Trp Tyr Gln Gln Lys Pro Gly Lys Ala
            165                 170                 175

Pro Lys Leu Leu Ile Tyr Asp Ala Ser Ser Leu Glu Ser Gly Val Pro
            180                 185                 190

Ser Arg Phe Ser Gly Ser Gly Ser Gly Thr Glu Phe Thr Leu Thr Ile
            195                 200                 205

Ser Ser Leu Gln Pro Asp Asp Phe Ala Thr Tyr Tyr Cys Gln Gln Arg
            210                 215                 220

Asn Arg Tyr Pro Pro Thr Phe Gly Gln Gly Thr Lys Val Glu Ile Lys
225                 230                 235                 240

Arg

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Gly Gly Ser Gly Gly Gly Gly Ser Gly Gly Gly Gly Ser
1               5                   10                  15

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
caggaaacag ctatgaccat gattac                                          26

<210> SEQ ID NO 78
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
```

<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (56)..(57)
<223> OTHER INFORMATION: a, c, t, g, unknown or other
<220> FEATURE:
<221> NAME/KEY: modified_base
<222> LOCATION: (59)..(60)
<223> OTHER INFORMATION: a, c, t, g, unknown or other

<400> SEQUENCE: 78
tgagacccac tccagcccct tccctggagc ctggcggacc camnmnnmn nmnnmnnmnn    60 a                                                                   61

<210> SEQ ID NO 79
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(19)
<223> OTHER INFORMATION: a, c, t, g, unknown or other
<220> FEATURE:
<221> NAME/KEY: modified_base
<222> LOCATION: (24)..(25)
<223> OTHER INFORMATION: a, c, t, g, unknown or other
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: modified_base
<222> LOCATION: (33)..(34)
<223> OTHER INFORMATION: a, c, t, g, unknown or other
<220> FEATURE:
<221> NAME/KEY: modified_base
<222> LOCATION: (39)..(40)
<223> OTHER INFORMATION: a, c, t, g, unknown or other
<220> FEATURE:
<221> NAME/KEY: modified_base
<222> LOCATION: (45)..(46)
<223> OTHER INFORMATION: a, c, t, g, unknown or other

<400> SEQUENCE: 79
ggctggagtg ggtctcannk attnnknnkn nknnkggtnn kacannktac gcagactccg    60
tgaa                                                                64

<210> SEQ ID NO 80
<211> LENGTH: 30
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 80
gacgttagta aatgaattt ctgtatgagg                                         30

<210> SEQ ID NO 81
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other

<400> SEQUENCE: 81
ccctggtttc tgctgatacc amnncaamnn mnmnnmnnm nnctgactgg cacggcaagt        60
ga                                                                     62

<210> SEQ ID NO 82
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (42)..(43)
<223> OTHER INFORMATION: a, c, t, g, unknown or other
<220> FEATURE:
<221> NAME/KEY: modified_base
<222> LOCATION: (45)..(46)
<223> OTHER INFORMATION: a, c, t, g, unknown or other
<220> FEATURE:
<221> NAME/KEY: modified_base
<222> LOCATION: (48)..(49)
<223> OTHER INFORMATION: a, c, t, g, unknown or other
<220> FEATURE:
<221> NAME/KEY: modified_base
<222> LOCATION: (51)..(52)
<223> OTHER INFORMATION: a, c, t, g, unknown or other
<220> FEATURE:
<221> NAME/KEY: modified_base
<222> LOCATION: (54)..(55)
<223> OTHER INFORMATION: a, c, t, g, unknown or other

<400> SEQUENCE: 82
ggtatcagca gaaaccaggg aaagcccta agctcctgat cnnknnknnk nnknnkttgg        60
``` aaa 63

```
<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 31C2&32H4 HCDR1

<400> SEQUENCE: 83

Ser Tyr Ala Met Ser
1               5
```